(12) United States Patent  
Krishnan

(10) Patent No.: US 11,660,419 B2  
(45) Date of Patent: May 30, 2023

(54) SYSTEMS, DEVICES, AND METHODS FOR GENERATING AND MANIPULATING OBJECTS IN A VIRTUAL REALITY OR MULTI-SENSORY ENVIRONMENT TO MAINTAIN A POSITIVE STATE OF A USER

(71) Applicant: PSYBER, Inc., Chicago, IL (US)

(72) Inventor: Prahlad Krishnan, Chicago, IL (US)

(73) Assignee: Psyber, Inc., Chicago, IL (US)

( * ) Notice: Subject to any disclaimer, the term of this patent is extended or adjusted under 35 U.S.C. 154(b) by 0 days.

(21) Appl. No.: 17/866,430

(22) Filed: Jul. 15, 2022

(65) Prior Publication Data

US 2023/0012960 A1 Jan. 19, 2023

Related U.S. Application Data

(60) Provisional application No. 63/245,625, filed on Sep. 17, 2021, provisional application No. 63/222,873, (Continued)

(51) Int. Cl.
*A61M 21/02* (2006.01)
*A61B 5/0535* (2021.01)
(Continued)

(52) U.S. Cl.
CPC .......... *A61M 21/02* (2013.01); *A61B 5/02055* (2013.01); *A61B 5/02405* (2013.01);
(Continued)

(58) Field of Classification Search
CPC ..... A61B 5/0006; A61B 5/165; A61B 5/0042; A61B 5/316; A61B 5/375; A61B 2505/09;
(Continued)

(56) References Cited

U.S. PATENT DOCUMENTS 10,856,032 B2 12/2020 Aimone et al.
10,893,822 B2 1/2021 Hendler et al.
(Continued)

FOREIGN PATENT DOCUMENTS

WO WO-2018195455 A1 10/2018
WO WO-2019161050 A1 8/2019

OTHER PUBLICATIONS

Haijen et al., "Predicting Responses to Psychedelics: A Prospective Study," Frontiers in Pharmacology, Nov. 2, 2018, 9:897, 20 pages.
(Continued)

*Primary Examiner* — Christine H Matthews
*Assistant Examiner* — Joshua Daryl D Lannu
(74) *Attorney, Agent, or Firm* — Cooley LLP

(57) ABSTRACT

Systems, devices, and methods described herein relate to multi-sensory presentation devices, including virtual reality (VR) devices, visual display devices, sound devices, haptic devices, and other forms of presentation devices, that are configured to present sensory elements, including visual and/or audio scenes, to a user. In some embodiments, one or more sensors including electroencephalography (EEG) sensors and a photoplethysmography (PPG) sensors, e.g., included in a brain-computer interface, can measure physiological data of a user to monitor a state of the user during the presentation of the visual and/or audio scenes. Such systems, devices, and methods can adapt one or more visual and/or audio scenes based on user physiological data, e.g., to control or manage the state of the user.

30 Claims, 19 Drawing Sheets
(11 of 19 Drawing Sheet(s) Filed in Color)

Related U.S. Application Data filed on Jul. 16, 2021, provisional application No. 63/225,152, filed on Jul. 23, 2021.

(51) Int. Cl.

| | | |
|---|---|---|
| *A61B 5/291* | (2021.01) | |
| *A61B 5/369* | (2021.01) | |
| *A61B 5/375* | (2021.01) | |
| *A61B 5/378* | (2021.01) | |
| *G16H 20/70* | (2018.01) | |
| *G16H 40/60* | (2018.01) | |
| *G06F 3/01* | (2006.01) | |
| *G16H 20/10* | (2018.01) | |
| *G16H 40/67* | (2018.01) | |
| *A61B 5/377* | (2021.01) | |
| *A61B 5/024* | (2006.01) | |
| *A61B 5/0205* | (2006.01) | |
| *A61M 21/00* | (2006.01) | |

(52) U.S. Cl.
CPC .......... *A61B 5/02416* (2013.01); *A61B 5/377* (2021.01); *G06F 3/015* (2013.01); *G16H 20/10* (2018.01); *G16H 20/70* (2018.01); *G16H 40/67* (2018.01); *A61M 2021/005* (2013.01); *A61M 2021/0016* (2013.01); *A61M 2021/0022* (2013.01); *A61M 2021/0027* (2013.01)

(58) Field of Classification Search
CPC ..... A61B 5/7405; A61B 5/742; A61B 5/7425; A61B 5/743; A61B 5/744; A61B 5/7455; A61M 2021/0022; A61M 2021/0044; A61M 21/02; A61M 2230/10; A61M 2021/0027; A61M 2021/0016; A61M 21/00; A61M 2205/05; A61M 2205/3303; G16H 20/30; G16H 20/10; G16H 20/70; A61H 2201/5043; A61H 2201/5048; A61H 2230/00; A61H 23/00
See application file for complete search history.

(56) References Cited

U.S. PATENT DOCUMENTS

| | | | |
|---|---|---|---|
| 10,959,640 | B2 | 3/2021 | Kawato et al. |
| 10,974,020 | B2 | 4/2021 | Rabin et al. |
| 2002/0103429 | A1 | 8/2002 | Decharms |
| 2012/0190460 | A1 | 7/2012 | Sessions |
| 2014/0257073 | A1* | 9/2014 | Machon ................. A61B 5/291 600/383 |
| 2015/0351655 | A1 | 12/2015 | Coleman |
| 2016/0005320 | A1* | 1/2016 | deCharms ............ A61B 8/0808 434/236 |
| 2016/0077547 | A1* | 3/2016 | Aimone ................ A61B 5/1114 345/8 |
| 2017/0249855 | A1* | 8/2017 | Gazzaley ............... A61B 5/375 |
| 2019/0269328 | A1* | 9/2019 | Porges ..................... A61B 5/11 |
| 2020/0234814 | A1* | 7/2020 | Theory ................ G16H 50/20 |
| 2020/0302825 | A1 | 9/2020 | Sachs et al. |

OTHER PUBLICATIONS

SAS and CHOPRA, "MeditAid: a wearable adaptive neurofeedback-based system for training mindfulness state," Personal and Ubiquitous Computing, Sep. 4, 2015, 19, 1169-1182.

Blake, Development of a bluetooth 4.0 PPG sensor for use in Heart Rate Variability analysis, IEEE International Conference on Consumer Electronics (ICCE), Jan. 9, 2015, pp. 301-304.

European Patent Office, International Search Report and Written Opinion for PCT/US2022/037351, dated Oct. 26, 2022, 21 pages.

\* cited by examiner

1100

1100

1100

1100

1200

1202

1300

1302

1304

1306

1308

1400

1402

1404

1406

SYSTEMS, DEVICES, AND METHODS FOR GENERATING AND MANIPULATING OBJECTS IN A VIRTUAL REALITY OR MULTI-SENSORY ENVIRONMENT TO MAINTAIN A POSITIVE STATE OF A USER

CROSS-REFERENCE TO RELATED APPLICATIONS

This application claims priority to U.S. Provisional Application No. 63/222,873, filed Jul. 16, 2021, U.S. Provisional Application No. 63/225,152, filed on Jul. 23, 2021, and U.S. Provisional Application No. 63/245,625, filed Sep. 17, 2021, the entire disclosures of each of which is incorporated herein by reference in their entirety.

TECHNICAL FIELD

The present disclosure relates to systems, devices, and methods for generating and manipulating objects in a virtual reality or multi-sensory environment, and in particular, relates to the field of data processing and artificial intelligence, e.g., for treating a mental and/or physical condition. More particularly, the embodiments described herein relate to data processing and machine learning methods and apparatuses for generating multi-sensory environments and providing adaptive digital therapy, e.g., in conjunction with drug treatment, and for providing patient monitoring and feedback associated with the adaptive digital therapy to ensure suitable mindsets or states of a user.

BACKGROUND

Drug treatments have been used to treat many different types of medical conditions and disorders. Some known drug treatments can oftentimes take weeks or months to achieve their full effects, and in some instances may require continued use or lead to drug dependencies or other complications. Psychotherapy and other types of human interactions can be useful for treating disorders, e.g., for improving an effectiveness of a drug treatment, mitigating/reducing the complications associated with a drug treatment or medical procedure, or generally improving an individual's well-being. But such interactions may be limited by the availability of trained professionals and vary in effectiveness depending on skills, time availability of the trained professional and patient, and/or specific techniques used by trained professionals. Thus, a need exists for improved systems and methods for treating medical conditions and disorders, as well as improving the safety profile and/or response to various medical procedures. Additionally, as psychedelics and other types of compounds are being developed as treatments for neuropsychiatric disorders, designing the right set and setting are important considerations. Set and setting are factors relevant to the experience, safety, and outcomes that occur when people use psychedelic drugs. Set refers to temperament, groundwork, expectation of the person having the experience and setting refers to the physical, social and cultural environment in which the experience takes place.

SUMMARY

Systems, devices, and methods described herein relate to multi-sensory presentation devices, including virtual reality (VR) devices, visual display devices, sound devices, haptic devices, and other forms of presentation devices, that are configured to present sensory elements, including visual and/or audio scenes, to a user.

In some embodiments, an apparatus can include a virtual reality (VR) device configured to present at least one of a visual, olfactory, gustatory, auditory, or haptic signal to a user; a set of sensors configured to measure user data, the set of sensors including at least an electroencephalography (EEG) sensor and/or a photoplethysmography (PPG) sensor; a memory; and a processor operatively coupled to the virtual reality device, the set of sensors, and the memory. The processor is configured to: present, using the VR device, a scene including a first set of objects to the user, the first set of objects including visual, olfactory, gustatory, auditory, or haptic elements; instruct a user to engage in an activity for increasing focus and/or relaxation; after the user has been instructed to engage in the activity, iteratively perform until a score indicative of a state of the user satisfies a metric: measuring, using the set of sensors, the user data including at least EEG data and/or heart rate variability (HRV) data; determining, using a model trained to measure the state of the user, and based on the user data, the score of the user; and in response to the score of the user being above a threshold, modifying, using the VR device, the presentation of the first set of objects such that the first set of objects form or follow a pattern or presenting, using the VR device, an additional object; and in response to the score of the user satisfying the metric, present, using the VR device, a second set of objects to the user.

In some embodiments, an apparatus can include a virtual reality (VR) device configured to present at least one of a visual, olfactory, gustatory, auditory, or haptic signal to a user; one or more electroencephalography (EEG) sensors configured to measure EEG data of the user; a memory; and a processor operatively coupled to the virtual reality device, the one or more EEG sensors, and the memory. The processor is configured to: present, using the VR device, a scene including a first set of objects to the user, the first set of objects including visual, olfactory, gustatory, auditory, or haptic elements; instruct a user to engage in an activity for increasing focus and/or relaxation; after the user has been instructed to engage in the activity, iteratively perform until a score indicative of a state of the user satisfies a metric: measuring, using the one or more EEG sensors, the EEG data; determining, using a model trained to measure the state of the user, and based on the EEG data, the score of the user; and in response to the score of the user being above a threshold, modifying, using the VR device, the presentation of the first set of objects such that the first set of objects form or follow a pattern or presenting, using the VR device, an additional object; and in response to the score of the user satisfying the metric, present, using the VR device, a second set of objects to the user.

In some embodiments, a method can include presenting, using a virtual reality (VR) device, a scene including a first set of objects to the user, the first set of objects including visual, olfactory, gustatory, auditory, or haptic elements; instructing a user to engage in an activity for increasing focus and/or relaxation; after the user has been instructed to engage in the activity, iteratively performing until a score indicative of a state of the user satisfies a metric: measuring, using a set of sensors including an electroencephalography (EEG) sensor and/or a photoplethysmography (PPG) sensor, the user data including at least EEG data and/or heart rate variability (HRV) data; determining, using a model trained to measure the state of the user, and based on the user data, the score of the user; and in response to the score of the user being above a threshold, modifying, using the VR device, the presentation of the first set of objects such that the first set of objects form or follow a pattern or presenting, using the VR device, an additional object; and in response to the score of the user satisfying the metric, presenting, using the VR device, a second set of objects to the user.

In some embodiments, an apparatus can include: a multi-sensory presentation device configured to present at least one of a visual, olfactory, gustatory, auditory, or haptic signal to a user; a set of sensors configured to measure user data, the set of sensors including at least an electroencephalography (EEG) sensor and/or a photoplethysmography (PPG) sensor; a memory; and a processor operatively coupled to the memory, the multi-sensory presentation device, and the set of sensors. The processor configured is to: present, using the multi-sensory presentation device and after the user has received a drug treatment, a scene to the user, the scene including a first set of visual, olfactory, gustatory, auditory, or haptic elements; while the scene is being presented, iteratively perform: measuring, using the set of sensors, user data including at least EEG data and/or heart rate variability (HRV) data; determining, using a model trained to measure a state of the user, and based on the user data, a score of the user indicative of a state of the user; in response to the score being lower than a threshold, modifying, based on the score of the user, the scene to include a second set of visual, olfactory, gustatory, auditory, or haptic elements different from the first set of visual, olfactory, gustatory, auditory, or haptic elements; and in response to the score being greater than the threshold for a set period of time, modifying the scene to include a third set of visual, olfactory, gustatory, auditory, or haptic elements different from the first and second sets of visual, olfactory, gustatory, auditory, or haptic elements; and continue to present the scene to the user until a predetermined period of time has elapsed from the user receiving the drug treatment.

In some embodiments, an apparatus can include a multi-sensory presentation device configured to present at least one of a visual, olfactory, gustatory, auditory, or haptic signal to a user; one or more electroencephalography (EEG) sensors configured to measure EEG data of the user; a memory; and a processor operatively coupled to the memory, the multi-sensory presentation device, and the one or more EEG sensors. The processor is configured to: present, using the multi-sensory presentation device and after the user has received a drug treatment, a scene to the user, the scene including a first set of visual, olfactory, gustatory, auditory, or haptic elements; while the scene is being presented, iteratively perform: measuring, using the one or more EEG sensors, the EEG data; determining, using a model trained to measure a state of the user, and based on the EEG data, a score of the user indicative of a state of the user; in response to the score being lower than a threshold, modifying, based on the score of the user, the scene to include a second set of visual, olfactory, gustatory, auditory, or haptic elements different from the first set of visual, olfactory, gustatory, auditory, or haptic elements; and in response to the score being greater than the threshold for a set period of time, modifying the scene to include a third set of visual, olfactory, gustatory, auditory, or haptic elements different from the first and second sets of visual, olfactory, gustatory, auditory, or haptic elements; and continue to present the scene to the user until a predetermined period of time has elapsed from the user receiving the drug treatment.

In some embodiments, a method can include: presenting, using a multi-sensory presentation device and after the user has received a drug treatment, a scene to the user, the scene including a first set of visual, olfactory, gustatory, auditory, or haptic elements; while the scene is being presented, iteratively performing: measuring, using a set of sensors including an electroencephalography (EEG) sensor and/or a photoplethysmography (PPG) sensor, user data including at least EEG data and/or heart rate variability (HRV) data; determining, using a model trained to measure a state of the user, and based on the user data, a score of the user indicative of a state of the user; in response to the score being lower than a threshold, modifying, based on the score of the user, the scene to include a second set of visual, olfactory, gustatory, auditory, or haptic elements different from the first set of visual, olfactory, gustatory, auditory, or haptic elements; and in response to the score being greater than the threshold for a set period of time, modifying the scene to include a third set of visual, olfactory, gustatory, auditory, or haptic elements different from the first and second sets of visual, olfactory, gustatory, auditory, or haptic elements; and continuing to present the scene to the user until a predetermined period of time has elapsed from the user receiving the drug treatment.

In some embodiments, a method can include receiving, at a compute device, user data from sensors associated with a user during a presentation of content or interaction with content such as a digital therapy. The method can further include executing a machine learning model to determine an indication of state associated with the digital therapy based on the user data, the indication of state indicating a measure of progression within the digital therapy and/or toward an optimal mental state. The method can further include determining a modification to digital therapy based on the indication of state. The method can also include using that said state to monitor and adjust the setting. It can also include more specifically in the context of using psychedelics maintaining the right set and setting using adaptive digital therapy to achieve positive long-term well-being.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
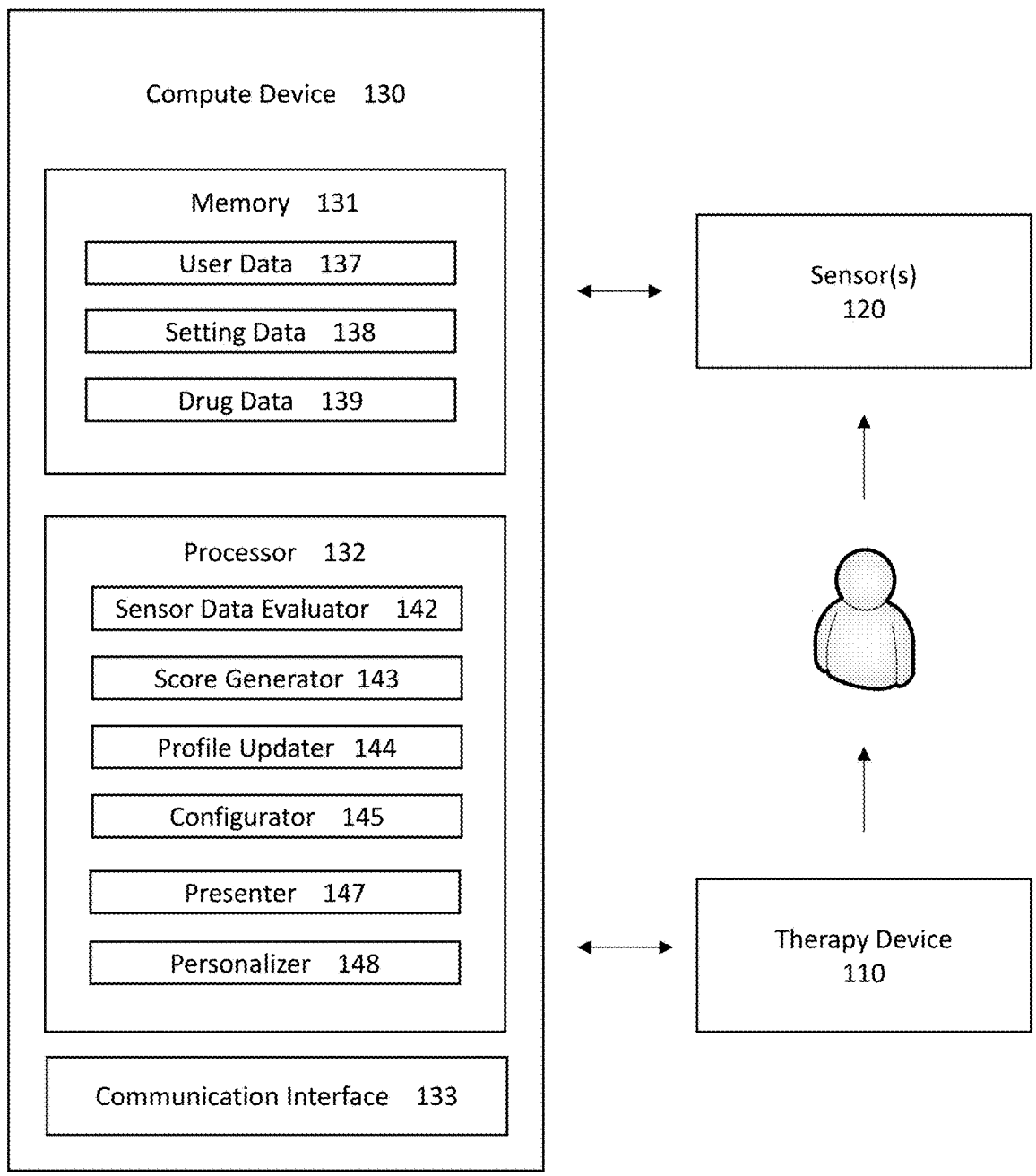
FIG. 1 is a schematic block diagram of a therapy system, according to an embodiment.

Described herein are one or more systems and methods relating to feedback-based digital therapies or interventions, e.g., to be used to prepare for and/or with drug treatments or medical procedures (e.g., imaging sessions, surgical procedures, etc.), and/or for improving wellbeing. For example, one or more system and methods described herein can be used prior to or with a psychedelic therapy or treatment, e.g., to treat a mental health disorder, depression, anxiety, substance abuse disorder, etc. In some embodiments, one or more systems and methods described herein relate to providing adaptive digital therapy in conjunction with drug treatment and providing a user (e.g., patient) monitoring and feedback associated with such therapies and/or treatment to adapt and ensure a suitable mindset and setting for such treatment.

A set of a user prior to and after receiving a drug treatment can be a useful variable. The set can relate to a user's mindset. A user with a positive set can feel well prepared, in a good mood, and ready and open toward an upcoming experience and have low levels of anxiety before drug intake. Users with positive sets are more likely to have less challenging experiences, and oftentimes may have peak experiences or a positive acute experience. On the other hand, a user with a negative set, such as a user with emotional excitability, anxiety, and/or apprehension, may be more likely to have a challenging experience. Therefore, training the user to have a suitable set prior to and/or after receiving a drug therapy or treatment can increase safety and/or efficacy of receiving the treatment. Such can also be the case with other types of procedures, e.g., medical procedures such as imaging sessions (e.g., with computed tomography (CT), magnetic resonance imaging (MRI), etc.), surgical procedures, medical exams, etc. One or more systems and methods described herein can be used to induce a predefined set (e.g., state) and setting for receiving a drug treatment (e.g., a psychedelic drug), including, but not limited to, for example, Psilocybin, Ketamine, Esketamine, R-Ketamine, RL-007 (e.g., for schizophrenia), Ibogaine, Deuterated Etifoxine, N-Acetylcysteine, methylenedioxymethyl amphetamine (MDMA), N-methyl-1-(3,4-methyl-enedioxyphenyl)propan-2-amine), methylenedioxy-methyl-amfetamine, 3,4-methylenedioxymethamphetamine, 3,4-Methylenedioxyamphetamine (MDA), Salvinorin A, Deuterated Mitragynine, Noribogaine, Dimethyltryptamine (DMT), N,N-DMT, D-Cycloserine, or other drug treatments with acute effects on a central nervous system.

The one or more therapy systems and methods described herein can provide real-time feedback and adaptive training on the user's progress towards a specific cognitive, emotional and physiological change, helping to increase their interoceptive awareness. As the user observes progress within a session and/or over multiple sessions, the user's perceived locus of control in self-regulating physiological activity and emotion can shift inwards and the user's self-efficacy can increase. A repeated use of one or more therapy systems and methods described herein can change the user's mindset, enable a better ability to self-regulate emotion, improve the user's ability to physiologically react to and recover from stressful situations, and become internalized, that overall can result in lower levels of trait anxiety and improve optimal mental states.

In some embodiments described herein, set and setting are involved in determining acute effects after receiving a drug treatment, such as, for example, the effects of a psychedelic, and/or long-term emotional and mental benefits of a drug treatment. For example, in addition to an individual's personal traits, the actual experience upon immediate onset of a psychedelic can be predictive of improved well-being at, for example, 2 and 4-week follow-ups. The acute experience is, in part, determined by an individual's set and setting. In some instances, acute experiences can be positively correlated to longer-term well-being. Specifically, higher ratings of peak experiences, described as experiencing disorientation in space and time, feelings of being free of inner conflict, feelings of awe, amazement and humility, and a sense of oneness with the universe, can have a long-term positive effect on the change in well-being after a psychedelic experience. Experiences described as challenging, characterized by anxiety, psychological struggle, fear, panic and/or paranoia, can negatively influence well-being and impact a safety profile of a drug or drug treatment session.

As noted above, with a positive set, a user can feel well prepared, relaxed, in a good mood, ready and open towards the upcoming experience and have had low levels of anxiety right before drug intake, and is associated with less challenging experiences and predictive of peak experiences. A user that can have peak experiences is often less hostile, tense, and anxious prior to dosing. Positive prior expectations can increase the likelihood of a positive acute experience. The individuals with positive prior expectations are more willing to confront anxiety and less frightened by the prospect of self-confrontation. On the other hand, a negative set can be characterized by emotional excitability, anxiety and apprehension. Therefore, a negative set can be predictive of challenging experiences. A user with higher levels of apprehension and anticipatory anxiety prior to dosing is more likely to have acute anxiety and/or experience psychological discomfort during a psychedelic experience. In addition, comfort in a setting and comfort with the people present during the psychedelic experience can be predictive of higher well-being scores. Sensor data collected and processed in substantially real-time and during a presentation of content or digital therapy, as described herein, can be used to determine and adapt a set and/or a setting before and/or during a psychedelic treatment, and therefore, lead to improved and safer acute experience and/or improved long-term well-being outcome. Optimal sets or mental states, before and/or during a psychedelic experience and/or prior to dosing, can include, but is not limited to, relaxation, low emotional excitability, and/or focus.

The one or more systems and methods described herein can utilize a closed-loop control system that can have multiple input and multiple output (MIMO) to induce and/or maintain a target mental state/optimal set for psychedelic treatment using brain-computer interface (BCI). In addition, in some instances, the one or more systems and methods described herein can analyze user data obtained using a multimodal sensor(s) that measure one or more aspects of human physiology and biochemistry input including, but not limited to, heart rate, heart rate variability, galvanic skin response, respiratory rate, eye movements, facial expressions, glucose, and/or pupillometry, to evaluate one or more outputs including, but not limited to, visual, olfactory, gustatory, auditory, haptic systems, and/or the like, to promote the right set and setting for responding to psychedelics and other drugs treatments with acute effects on the central nervous system.

Therefore, in some embodiments, the one or more systems and methods described herein can induce and/or maintain an optimal or improved set and setting, e.g., for experiencing psychedelic treatment, in preparation for a medical procedure, etc. The method can include performing an adaptive setting including auditory, visual, olfactory, gustatory and/or haptic experience feature systems. The method can further include obtaining, using a system, sensor data of a user (e.g., a patient) during the acute psychedelic experience. The method can further include determining, using a system, whether the sensor data includes information indicative of desired and/or optimal set functions (i.e., relaxed, focused, unagitated, positive affect, and/or the like) used for controlling the adaptive setting via changes to or maintaining the current state of the auditory, visual, olfactory, gustatory, haptic systems, and/or the like, to induce and/or maintain the desired and/or optimal set when it is determined that the sensor data includes the information indicative of desired and/or optimal set functions. The method can further include calculating an assessment/score of the user with regard to an improved or optimal set that controls the adaptive setting in the form of changes to or maintaining the current state of the auditory, visual, olfactory, gustatory and/or haptic systems. The method can further include adapting the adaptive setting output to each individual based on past calculated scores and past responses to various states of the adaptive setting. The method can further include personalizing the assessment/score to the needs and unique conditions of each user.

Moreover, the one or more systems and methods described herein can improve the safety profile and potentially improve/extend an efficacy and/or sustainability of response from various psychedelic treatments. The one or more systems and methods described herein can improve cognitive and emotional safety and well-being throughout a psychedelic experience by actively monitoring a patient's mental state and addressing factors that may cause a negative acute psychedelic experience. Specifically, the one or more systems and methods described herein can assist a user in entering and maintaining a state such as, for example, relaxed, focused, unagitated, positive affect, or reduced emotional excitability, and can provide the user with positive and comfortable environments that help to induce and maintain this mental state/set.

FIG. 1 is a block diagram that illustrates a therapy system 100, according to an embodiment. The therapy system 100 includes a therapy device 110, sensor(s) 120, and a compute device 130 that collectively can adaptively present multi-sensory elements, e.g., that are part of a digital therapy or content (e.g., a digital exercise, digital settings, etc.), to a user. The multi-sensory elements can include, for example, one or more visual, olfactory, gustatory, auditory, or haptic signals or elements. In some implementations, the therapy device 110, the sensor(s) 120, and the compute device 130 can communicate with one another via a network (not shown). The network can be any type of network (e.g., a local area network (LAN), a wide area network (WAN), a virtual network, a telecommunications network) implemented as a wired network and/or wireless network and used to operatively couple the devices. In some implementations, the therapy device 110, the sensor(s) 120, and the compute device 130 can communicate using one or more direct (e.g., not using an intermediary device such as, for example, a router) electromagnetic communications (e.g., one or more Bluetooth™ communication channels between the therapy device 110, the sensor(s) 120, and the compute device 130).

The therapy device 110 and the compute device 130, each can be or include, but is not limited to, for example, a cellular telephone (e.g., smartphone), a tablet computer, a laptop computer, a desktop computer, a portable media player, an audio device, a wearable digital device (e.g., digital glasses, wristband, wristwatch, brooch, armbands, virtual reality/augmented reality headset, a tactile vest), a projector or other display device, an audio device such as headphones, and/or a scent simulation device, etc. In some implementations, one or more of the devices in the therapy system 100 (e.g., the therapy device 110, the sensor 120, and the compute device 130) can include a user interface (e.g., a graphical user interface (GUI), a mouse, a keyboard, a touchpad, a virtual reality headset, an augmented headset, haptic interface, and/or a microphone) that enables a user to control the operation of the devices connected thereto as described in more detail herein. While not shown in FIG. 1, in some embodiments the therapy device 110 can be part of the compute device 130. In some embodiments, the therapy device 110 can be implemented as a virtual reality (VR) device or a multi-sensory device. The therapy device 110 can be configured to generate and present one or more visual, olfactory, gustatory, auditory, or haptic signals or elements. In some embodiments, the therapy device 110 can include one or more of: a projector or display, a scent delivery device or system, a tactile device (e.g., a tactile vest, armband, headband, headset, etc.), or an audio device (e.g., headphones, speakers, etc.).

The sensor(s) 120 can include any suitable component that captures information about a user, an environment of the user, objects in the environment around the user and/or the compute device 130. The sensor(s) 120 can be or include multi-modal sensor(s). In some embodiments, the sensor(s) 120 can include a brain-computer interface (BCI), an electroencephalography (EEG) device, a photoplethysmography (PPG) sensor, or other physiological sensors, behavioral sensors, or environmental sensors. The sensor(s) 120 can include, but is not limited to, for example, an electrode that is attached to the head of a user (e.g., a patient). The sensor(s) 120 can measure, but is not limited to, for example, EEG, electrooculography, electromyography (EMG), pulse oximetry, electrocardiogram (EKG), respiratory rate, eye movements, pupillometry, glucose, heart rate, heart rate variability (HRV), PPG, blood pressure, blood pressure variability, baroreflex sensitivity, electrodermal activity (EDA), galvanic skin response (GSR), and/or body temperature.

In some implementations, the sensor(s) 120 can include, but is not limited to, for example, image capture devices (e.g., cameras), ambient light sensors, audio devices (e.g., microphones), light sensors (e.g., photodetectors), proprioceptive sensors, position sensors, tactile sensors, force or torque sensors, temperature sensors, pressure sensors, motion sensors, sound detectors, gyroscopes, accelerometers, blood oxygen sensors, metabolic sensors, glucose monitoring sensors, or combinations thereof. The sensor(s) 120 can measure, for example, one or more of motion data, mobile device data (e.g., digital exhaust, metadata, device use data), wearable device data, geolocation data, sound data, camera data, therapy/training session data, medical record data, input data, environmental data, application usage data, attention data, arousal data, valence data, activity data, sleep data, nutrition data, menstrual cycle data, cardiac data, heart rate data, heart rate variability data, social functioning data, and/or facial expression data. While not shown in FIG. 1, in some embodiments the sensor(s) 120 can be part of (e.g., integrated into) the compute device 130 and/or the therapy device 110.

The compute device 130 can include a memory 131, a processor 132, and a communication interface. The memory 131 can store data (e.g., user data 137, setting data 138, the drug data 139) and/or a set of codes. The processor 132 can be operatively coupled to the memory 131, and can process the data and execute the set of codes. The compute device 130 can further include one or more input portions (not shown) that receive at least a portion of the data 137 from the sensor(s) 120. The one or more input portions can be/include, but are not limited to, for example, an antenna that receives electromagnetic waves (e.g., Bluetooth™ signals and/or WiFi™ signals), and/or an input port (e.g., USB port).

The memory 131 can be, but is not limited to, for example, a memory buffer, a random access memory (RAM), a read-only memory (ROM), a hard drive, a flash drive, a secure digital (SD) memory card, a compact disk (CD), and/or a universal flash storage (UFS) device. The memory 131 can store, for example, data (e.g., user data 137, setting data 138, drug data 139, etc.) and one or more codes that includes instructions to cause the processor 132 to perform one or more processes or functions (e.g., the score generator 143, the profile updater 144, the personalizer 148, etc.).

The memory 131 can store data including user data 137, setting data 138, and drug data 139. The user data 137 can include, but is not limited to, sensor data (e.g., EEG data, respiratory rate data, etc.) of the user received from the sensor 120, biographic data of the user, demographic data of the user, and/or user profile data provided by the user and/or a therapist. In some implementations, the user data 137, the setting data 138, and drug data 139 can be collected during a pre-treatment session (e.g., before a psychedelic treatment) and/or during a treatment session or in-treatment session (e.g., during a psychedelic treatment).

In some instances, the memory 131 can also store user data from past therapy sessions (e.g., to collect data for training a machine learning model). For example, the user data from past therapy sessions can include, but is not limited to, past performance data, past clinical response data, past difficulty level data, past session length data, past raw sensor data, past setting response, and/or past exercise and/or experience score data.

The drug data can include medications of the user including, but not limited to, for example, a psychedelic drug, including, but not limited to, for example, Psilocybin, Ketamine, Esketamine, R-Ketamine, RL-007 (e.g., for schizophrenia), Ibogaine, Deuterated Etifoxine, N-Acetylcysteine, methylenedioxy-methylamphetamine (MDMA), N-methyl-1-(3,4-methylenedioxyphenyl)propan-2-amine), methylenedioxy-methylamfetamine, 3,4-methylenedioxymethamphetamine, 3,4-Methylenedioxyamphetamine (MDA), Salvinorin A, Deuterated Mitragynine, Noribogaine, Dimethyltryptamine (DMT), N,N-DMT, D-Cycloserine, psychedelics, antidepressants, fluoxetine, sertraline, paroxetine, citalopram, venlafaxine, benzodiazepines, valproate, lithium carbamazepine, tiagabine, buspirone, barbiturates, diltiazem, or other drugs with acute central nervous system effects. The drug data can further include medication dosage data of the user and/or drug consumption timeline data of the user. The setting data can include, but is not limited to, multi-sensory setting data provided by the user, multi-sensory setting data provided by a therapist, and/or setting data from a digital therapy or intervention.

The communication interface 133 of the compute device 130 can be a hardware component of the compute device 130 to facilitate data communication between the compute device 130 and the therapy device 110 and/or the sensor(s) 120. The communication interface 133 is operatively coupled to and used by the processor 104 and/or the memory 102. In some embodiments, the communication interface 133 can also facilitate data communication between the compute device 130 and an external device (e.g., a server; not shown). The communication interface 133 can be, for example, a network interface card (NIC), a Wi-Fi® transceiver, a Bluetooth® transceiver, an optical communication module, and/or any other suitable wired and/or wireless communication interface. For example, the communication interface 133 can facilitate receiving or transmitting the user data 137, the setting data 138, the drug data 139, a machine learning model(s), and/or the like, from/to the server (not shown).

The processor 132 can be, for example, a hardware based integrated circuit (IC) or any other suitable processing device configured to run or execute the one or more codes. For example, the processor 132 can include, but is not limited to, a general-purpose processor, a central processing unit (CPU), an accelerated processing unit (APU), an application specific integrated circuit (ASIC), a graphics processing unit (GPU), and/or a deep learning processor. In some instances, the processor 132 can be operatively coupled to the memory 131 through a system bus (for example, address bus, data bus, and/or control bus, not shown). The processor 132 includes a sensor data evaluator 142, a score generator 143, a profile updater 144, a configurator 145, a presenter 147, and a personalizer 148 that can be or include software stored in the memory 131 and executed by the processor 132. For example, code to cause the score generator 143 to determine a measure associated with a state of a user can be stored in the memory 131 and executed by the processor 132. Alternatively, the sensor data evaluator 142, the score generator 143, the profile updater 144, the configurator 145, the presenter 147, and the personalizer 148 can include hardware-based devices. For example, a process to cause the presenter 147 to show a progress of meditation, attention, and/or relaxation states of the user can be implemented on an individual integrated circuit chip.

As shown in FIG. 1, the compute device 130 can be or include a local compute device (e.g., a desktop computer, a laptop, a mobile phone, a chip/processing unit, or a tablet) that is connected (e.g., using a wire(s)) and/or is operatively coupled (e.g., via electromagnetic waves) to the therapy device 110 and the sensor(s) 120. Although shown as separate devices, in some embodiments, the compute device 130, the therapy device 110, and/or the sensor(s) 120 can be implemented in an integrated device can collectively perform functions of the compute device 130, the therapy device 110, and/or the sensor(s) 120. For example, in some embodiments, the integrated device can be/include a headset (e.g., a virtual reality headset or an artificial reality headset) that can present a digital therapy during a pre-treatment session and/or during an in-treatment session, sense data from the user during the pre-treatment session and/or during the in-treatment session, and process the data to adaptively adjust/improve digital therapy, as described in further details herein.

In some embodiments the electronic circuitry, function, modules, models, and/or codes of the compute device 130 can be implemented on a server (e.g., a storage database, a cloud computing server). The server can be/include one or more compute devices particularly suitable for data storage, data processing, and/or data communication. For example, the server can include a network of electronic memories, a network of magnetic memories, a server(s), a blade server(s), a storage area network(s), a network attached storage(s), deep learning computing servers, deep learning storage servers, and/or the like. The server can include a memory, a processor, and/or a communication interface that are structurally and/or functionally similar to the memory 131, the processor 132, and/or the communication interface 133, as shown and described with respect to the compute device 130. In one example, the user data, the setting data, and/or the drug data can be stored on a database server. In another example, a machine learning model of the score generator 143 can be trained and/or executed by one or more graphical processing units of a computing server (not shown in FIG. 1).

The sensor data evaluator 142 can evaluate or determine (e.g., determine a measure of data sufficiency) whether user data 137 received from the sensor 120 and stored in the memory 131 includes sufficient information for determining a relaxation state (e.g., based on EEG data and/or HRV data), an attention state (e.g., based on EEG signals from the frontal/prefrontal regions), a meditation state (e.g., based on EEG data and/or HRV data), or other suitable state of the user, e.g., for assessing whether the user is prepared for receiving a treatment (e.g., a psychedelic). Similarly stated, the sensor data evaluator 142 can be used as a filter to determine whether the user data 137 provided by the sensor 120 and/or stored in the memory 131 is suitable (e.g., has a signal-to-noise ratio (SNR) above a predetermined threshold) for determining an indication of state (e.g., including the relaxation state, the attention state, the meditation state, or another state of the user).

In some instances, for example, the sensor 120 can provide electroencephalography (EEG) data to the compute device 130 and/or store the EEG data in the memory 131. The sensor data evaluator 142 can perform a substantially real-time impedance measurement(s) and determine whether specific impedance levels meet previously determined criteria (e.g., threshold impedance values being below 1 mΩ, 1 Ω, 10 Ω, 100 Ω, 1 KΩ, 10 KΩ20 KΩ, or 1 MG). For example, a noise to EEG signals can be caused by, but is not limited to, muscle movements, blinking, sweat, unintentional electrostatics, that can interfere with the EEG signals and making the EEG data less accurate. In some implementations, the sensor data evaluator can determine if a signal-to-noise (SNR) ratio of the EEG data is not suitable for further processing. When the sensor data evaluator 142 determines that the user data provided by the sensor 120 and/or stored in the memory 131 is not suitable and/or sufficient for determining an indication of state, the processor 132 can generate a notice to the user and/or a therapist, which can, for example, instruct the user to correct or address the unsuitability of the data and/or propose a remedial action (e.g., to adjust a position of a sensor on the body of the user). On the other hand, when the sensor data evaluator 142 determines that the user data 137 provided by the sensor 120 and/or stored in the memory 131 is suitable and/or sufficient for determining an indication of state, the user data 137 can be passed on to the score generator 143.

In some implementations, the sensor data can include heart rate variability (HRV) data and/or breathing data. The HRV data can be collected, for example, using a photoplethysmography (PPG) sensor built into a BCI interface. The sensor data evaluator 142 can evaluate the HRV data and/or the breathing data, and the score generator 143 can generate the score based on the HRV data and/or the breathing data. A feedback based on the HRV data can generate a balance between the sympathetic nervous system (SNS) and the parasympathetic nervous system (PNS), whose imbalance (e.g., hyperarousal of the SNS, disrupted the PNS function) is associated with higher levels of anxiety. HRV reflects the relationship between the PNS and the SNS and can be sensitive to changes in emotional state, especially with regard to valence. As such, HRV biofeedback can be used to assist the user with self-regulating the user's emotion(s) by incentivizing the user to enhance cardiac coherence and create autonomic balance.

In some implementations, the sensor data can include EEG data combined with the HRV data. The sensor data evaluator 142 can evaluate the EEG data and the HRV data, and the score generator 143 can generate the score based on the EEG data and the HRV data. In an embodiment, the EEG data and the HRV data can be used by the score generator 143 to generate a score, as further described in the sections below.

In some implementations, the sensor data can include blood glucose data combined with HRV data as measured by various sensors. The sensor data evaluator 142 can evaluate the blood glucose data and the HRV data, and the score generator 143 can generate the score based on the blood glucose data and the HRV data. In an embodiment, the blood glucose data and the HRV data can be used by the score generator 143 to generate a score, as further described in the sections below.

In some implementations, the sensor data can include EEG data combined with respiratory rate data. The sensor data evaluator 142 can evaluate the EEG data and the respiratory rate data, and the score generator 143 can generate the score based on the EEG data and the respiratory rate data. In an embodiment, the EEG data and the respiratory rate data can be used by the score generator 143 to generate a score, as further described in the sections below.

In some implementations, the sensor data can include galvanic skin response data combined with HR variability data. The sensor data evaluator 142 can evaluate the galvanic skin response data and the HR variability data, and the score generator 143 can generate the score based on the galvanic skin response data and the HR variability data. In an embodiment, the galvanic skin response data and the HR variability data can be used by the score generator 143 to generate a score, as further described in the sections below.

In some implementations, the sensor data can include EEG data, HRV data, GSR data, glucose data, pupillometry data, or combination thereof. The sensor data evaluator 142 can evaluate the EEG data, the HRV data, the GSR data, the glucose data, and/or the pupillometry data, and the score generator 143 can generate the score based on the EEG data, the HRV data, the GSR data, the glucose data, the pupillometry data, or combination thereof. In an embodiment, the EEG data, HRV data, GSR data, glucose data, pupillometry data, or combination thereof can be used by the score generator 143 to generate a score, as further described in the sections below.

The score generator 143 can be executed to receive the user data 137, the setting data 138 and/or drug data 139 and to generate using that data the indication of a state of the user (e.g., indicative of a relaxation state of the user, an attention state of the user, a meditation state of the user, a state of user related to the user's central nervous system (CNS), valence, and/or any other appropriate mental state of the user for psychedelics). In some implementations, the indication of state can be used to determine a measure of progression of the user, indicating whether the user is progressing through multi-sensory experience or exercise (e.g., a meditation program, a gameplay, an adaptive settings system, a digital therapy, a relaxation therapy/training, an attention therapy/ training, and/or a meditation therapy/training including one or more sensory elements such as visual, audio, tactile, etc.) or other digital content and/or programming. The measure of progression can be defined as a measure of whether a user is progressing towards the goal in any given moment and how well they are progressing in that moment. For example, in some instances, a multi-sensory experience or exercise can include at least one end-goal (e.g., a pattern/shape) and the user can actively try to achieve that end-goal within the multi-sensory experience or exercise itself (e.g., turn scattered particles into the pattern/shape). In some implementations, the indication of state can be used to determine a measure of completeness of the user. The measure of completeness can be defined as a measure of percentage completed in a level or session of the multi-sensory experience or exercise. The measure of progression can be, for example, equivalent to a measure of whether a user is progressing towards the goal at a given period of time and/or how well they are progressing in that moment. In some implementations, the indication of state can be used to determine a measure of response to the multi-sensory experience or exercise (e.g., one or more digital settings) or, in other words, a measure of progression toward optimal mental state or set in response to the multi-sensory experience or exercise. For example, in some instances, the multi-sensory experience or exercise has no beginning or end-goal, and/or the user can be passive participant. In other words, in some instances, there is no indication of progression within the multi-sensory experience or exercise. Therefore, progress in this context can be a measure of mental state response to a digital setting and not a measure of how far a gameplay, content, or exercise has progressed.

In one example, a multi-sensory experience and/or exercise can include a gameplay. The gameplay can have one or more levels or checkpoints. Each level of the gameplay can initially have a difficulty assigned to that level, which can be, for example, represented by a preset threshold score. A level of difficulty/threshold score within the level can potentially change based on the adaptive difficulty system, but otherwise it can stay substantially the same for the entirety of that level of difficulty/threshold score. The threshold score can be used to determine the minimum score a user needs to achieve in order to be progressing towards an end state/goal in the level of difficulty. The higher the user score is above the threshold, the faster the user can progress in the level of difficulty and/or towards the end state/goal. If the user falls below the threshold, the user can regress away from the end state/goal and/or the level of difficulty, or can make slower progress towards the end goal. In another example, the profile updater 144 can receive user data (e.g., collected from the sensor(s) 120) and can update a subject profile based on a mental state response(s) of the user to various digital settings presented to user. In other words, the profile updater 144 can update a subject's profile based on user data indicating a set of one or more settings that induce or maintain an optimal mental state or set for the subject. In some embodiments, a threshold score can be assigned to different settings (e.g., digital therapy, sensory objects or elements, etc.), with the threshold score indicating when it may be appropriate to change or maintain one or more of the settings. The threshold score can be related or specific to the subject. For example, a first subject's score can be different (lower or higher) from a second subject's score to indicate that a setting works. In other words, the threshold score can be lower for the first subject to accommodate for a lower score indicating positive outcome of the setting versus the same score not indicating a positive outcome in the second subject. The configurator 145 can then adapt a possible setting(s) that can be presented to the user based on the user's updated user profile or threshold score(s). In yet another example, a threshold score can be adapted for each user for refining an adaptive setting (e.g., to determine to change or maintain a current digital setting).

In some implementations, each level of difficulty can have a beginning state and end state/goal (e.g., defined by the visuals and audio). The score generator 143 can generate a set of scores for the user at preset intervals (e.g., every 100 ms). When a score from the set of scores, e.g., generated for a certain period of time, is above the threshold, the user is progressing towards the end state/goal (e.g., at a rate based on how far the user is above the threshold). When the score (e.g., generated for a particular period of time) is below the threshold, the user is regressing or progressing more slowly towards the beginning state (e.g., at a rate based on how far the user is below the threshold). To get to the end state/goal, the set of scores of the user should be averaging above a preset threshold value for an associated period of time. For example, the period of time can be determined based on how much the set of scores of the user is averaging above the threshold score, with higher scores having shorter times to completion (e.g., higher scores being associated with shorter periods of time).

In some instances, the score generator 143 can be adapted to calculate a measure (e.g., score) indicative of a meditation state, an attention state, a relaxation state, or other mental or physiological state of the user, e.g., using a probabilistic model (e.g., a supervised learning model, an unsupervised learning model, an operant learning model). In some implementations, the score generator 143 can calculate an evaluation of the meditation state, the attention state, and/or the relaxation state of the user in response to a performance of the user (e.g., during a digital therapy) or in response to a digital setting presented to the user. The score generator 143 can be operatively coupled to the profile updater 144.

In some instances, the score generated by the score generator 143 can be a score between 0 and 100 representing a mental state, with 0 representing intense psychological discomfort and 100 being completely comfortable and at-ease. Alternatively, any numerical and/or other type of scale can be used, e.g., a numerical scale from −100 to 100, a color or gradient based scale, etc. In some embodiments, the score generator can include multiple probabilistic models, each bespoke to or associated with a specific psychedelic compound or drug treatment.

In some instances, the score generator 143 can implement a machine learning model and can include a set of model parameters (e.g., nodes, weights, biases, etc.) that can be used to determine an indication of state associated with the digital therapy based on the user data 137, the setting data 138, and/or the drug data 139. The indication of state can be indicative of a relaxation state, an attention state, a meditation state, or other mental state of the user. In one example, the score generator 143 can generate a score between 0 and 100 with 0 indicating a completely unfocused user and 100 indicating a completely focused user. In another example, the indication of state generated by the machine learning model can be an array of numbers including a first number indicative of a relaxation state, a second number indicative of an attention state, and a third number indicative of a meditation state. In yet another example, the indication of state generated by the machine learning model can be an overall indication of state that represents an average or a weighted average of the relaxation state, the attention state and the meditation state. While relaxation, attention, and meditation states are described herein with respect to the examples, it can be appreciated that other types of mental states and/or any number of mental states can be used with the systems, devices, and methods described herein. And while numerical scores are described herein, it can be appreciated that numerical scores and/or other types of scores (e.g., words, colors, etc.) can be used.

In some instances, the score generator 143 can be a supervised machine learning model configured to receive a set of past user data (e.g., a set of past sensor data), a set of past setting data, a set of past drug data and a set of determined indications of state. A subset of user data from the set of past user data, a subset of setting data from the set of past setting data, and/or subset of drug data from the set of past drug data can be associated with a determined indication of state from the set of determined indications of state to produce labeled data. The labeled data can be used to train the set of model parameters (e.g., to identify the set of model parameters and/or determine weights associated with model parameters).

The score generator 143 can include, but is not limited to, a supervised machine learning model, a deep learning model, a boosted decision tree method, an ensemble of decision trees, an extreme gradient boosting (XGBoost) model, a random forest, a support vector machine (SVM), a feed-forward machine learning model, a recurrent neural network (RNN), a convolutional neural network (CNN), a graph neural network (GNN), an adversarial network model, an instance-based training model, a transformer neural network, and/or an ensemble of machine learning models. The set of model parameters of the score generator 143 can include a set of weights, a set of biases, and/or a set of activation functions that, once trained, can be executed to generate an indication of state from the user data 137, the setting data 138, and/or the drug data 139.

In one example, the score generator 143 can be a deep learning model that includes an input layer, an output layer, and multiple hidden layers (e.g., 5 layers, 10 layers, 20 layers, 50 layers, 100 layers, 200 layers, etc.). The multiple hidden layers can include normalization layers, fully connected layers, activation layers, convolutional layers, temporal convolutional layer, spatial convolutional layers, recurrent layers, and/or any other layers that are suitable for representing a correlation between the indication of state and the user data 137, the setting data 138, and/or the drug data 139.

In one example, the score generator 143 can be an XGBoost model that includes, but is not limited to, a set of hyper-parameters such as, for example, a number of boost rounds that defines the number of boosting rounds or trees in the XGBoost model, and/or maximum depth that defines a maximum number of permitted nodes from a root of a tree of the XGBoost model to a leaf of the tree. The XGBoost model can include, but is not limited to, a set of trees, a set of nodes, a set of weights, and/or a set of biases.

In some implementations, the score generator 143 (e.g., a deep learning model or an XGBoost model) can be configured to iteratively receive a subset of user data from the set of past user data, a subset of setting data from the set of past setting data, and/or a subset of drug data from the set of past drug data described above and generate an output. Each subset of user data from the set of past user data, each subset of setting data from the set of past setting data, and/or each subset of drug data from the set of past drug data is associated with a determined indication of state from the set of determined indications of state. The output and the determined indications of state can be compared using an objective function (also referred to as cost function) to generate a training loss value.

The objective function can include, but is not limited to, for example, a mean square error objective function, a mean absolute error objective function, a mean absolute percentage error objective function, a logcosh objective function, and/or a categorical crossentropy objective function. The set of model parameters of the score generator 143 can be modified or optimized using an optimization method (e.g., a gradient descent method, a stochastic gradient descent method, the Adagrad method, the Adam method, and/or the Adadelta method) in multiple iterations. The objective function can be executed at each iteration from the multiple iterations until the training loss value converges to a predetermined training threshold (e.g., 80%, 85%, 90%, 95%, 99%, etc.). In some instances, the predetermined training threshold can be manually determined/set. In some instances, the predetermined training threshold can be automatically set based on a training time for the score generator 143.

Once trained, the score generator 143 can be executed to generate the indication of state from the user data 137, the setting data 138, and/or the drug data 139 within an accuracy margin defined by the predetermined training threshold. In some implementations, the compute device 130 can optionally include an auditor (not shown) that can verify the indication of state for the user data 137, the setting data 138, and/or the drug data 139 to generate (e.g., by prompting a physician or a therapist to determine a state from the user data 137, the setting data 138, and/or the drug data 139) a truth-value state and an accuracy score of the score generator 143. The score generator 143 can be further trained using the accuracy score, the user data 137, the setting data 138, and/or the drug data 139.

Once trained, the score generator 143 can generate the indication of state from the user data 137, the setting data 138, and/or the drug data 139. In some instances, for example, the score generator 143 can generate an indication of state of a user in a fraction of the time it normally would take by, for example, a therapist to determine a score based on the user data 137, the setting data 138, and/or the drug data 139. In some instances, a therapist can generally spend, for example, 1 minute, 2 minutes, or 5 minutes, to generate the indication of state based on the user data 137, the setting data 138, and/or the drug data 139. In contrast, the score generator 143 can spend, for example, 100 milliseconds, 1 second, or 2 seconds to generate the indication of state based on the user data 137, the setting data 138, and/or the drug data 139. Therefore, the score generator 143 can be used to generate a set of indications of state from setting data, user data, and/or drug data quickly to substantially improve determination of state of users (e.g., 10 times faster, 100 times faster, 1000 times faster, 1,000,000 times faster, or 1,000,000,000 times faster). In some instances, the score generator 143 can generate an indication of state of a user that more accurately or objectively reflects a state of the user than a determination of state made by a therapist based on the user data 137, the setting data 138, and/or the drug data 139. This can be due to, for example, personal biases of a therapist, inexperience of a therapist, or other factors. The score generator 143 can be configured to account for such biases and provide scores indicative of a user's state that are objective measures.

The profile updater 144 can receive the indication of state of the user (e.g., indicative of a relaxation state, an attention state, a meditation state, or other mental state of the user) from the score generator 143. In response to receiving the indication of state of the user, the profile updater 144 can update a user profile of the user (e.g., stored in the memory 131) to generate an updated user profile. The profile updater 144 can be operatively coupled to the configurator 145 that can set a difficulty level of the multi-sensory experience or exercise (e.g., during a digital therapy and/or intervention) or update a setting selection, based on the user's performance during the multi-sensory experience or exercise and/or in response to the updated user profile of the user. Alternatively, in some instances, the configurator 145 can be manually set by a professional (e.g., a therapist or a physician) to set the difficulty level of the multi-sensory experience or exercise based on the indication of state. The configurator 145 can set a difficulty of the multi-sensory experience or exercise for each user based on previous assessments of relaxation, attention, meditation and/or other states as determined by the sensor data evaluator 142. In some embodiments, setting the difficulty level can include establishing a higher threshold that a score of the user must reach and maintain, e.g., to successfully advance pass a checkpoint or level.

Figure 3:
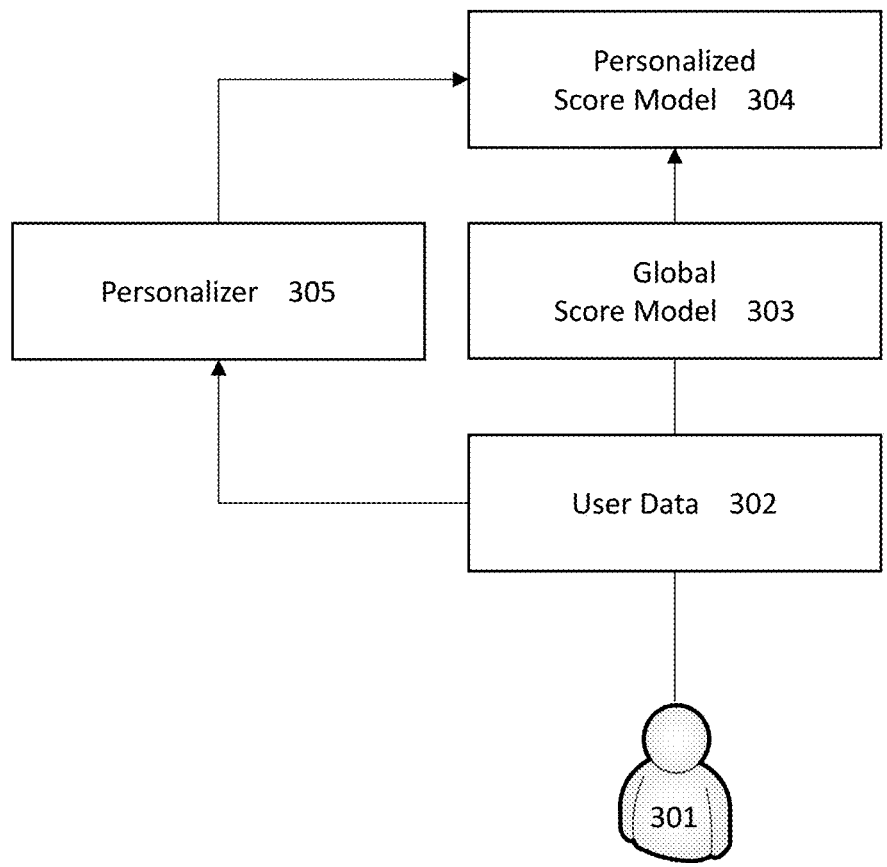
FIG. 3 is a flow chart illustrating the flow of data between components of a therapy system to produce a personalized classifier, according to an embodiment.

The personalizer 148 can receive, for example, the user data 137 (e.g., bio-signals), the setting data 138 (e.g., an indication of a music preference), and/or the drug data 139 (e.g., an indication drug consumption amount) of the user during a multi-sensory experience or exercise and the machine learning model of the score generator 143 (also referred to as the "global classifier" or the "classifier") to produce a user-specific score model (e.g., a user-specific classifier, as further described with reference to FIG. 3). For example, the user data 137, the setting data 138, and/or the drug data 139 of the user during a multi-sensory experience or exercise can be evaluated, e.g., by a compute device or a professional (e.g., a therapist or a physician), over a time period (e.g., five minutes, ten minutes, twenty minutes, five hours, ten hours, twenty hours, one day two days, or one week, two weeks, etc.) to produce truth-value indications of state of the user. The truth-value indications of state of the user, the user data, the setting data, the drug data, and/or past score data can be used to retrain the machine learning model of the score generator 143 and produce the user-specific score model. Doing so can provide a further personalized training method for the user in accordance to the condition and unique signals of the user. The personalizer 148 can control and adapt the compute device 130 to the specific needs and/or unique conditions of each individual user.

In some instances, the compute device 130 can be configured to track a progress of the user and/or an adherence of the user to one or more multi-sensory experience or exercise sessions and/or goals. In some instances, the compute device 130 can collect metadata (e.g., timestamps of events and/or collected data) during the one or more digital therapy sessions. For example, a timestamped set of data of the user during therapy exercise conducted during a time (e.g., a week, 2 weeks, a month, 2 months, etc.) can be plotted to show a trend of the progress of the user and/or adherence of the user to the one or more multi-sensory experience or exercise sessions.

In some implementations, the processor 132 can optionally execute a difficulty model (not shown) that can adaptively advance, regress, or change the multi-sensory experience or exercise including, but not limited to, a relaxation therapy/training exercise, an attention therapy/training exercise, a meditation therapy/training exercise, and/or any other suitable experiences or exercises administered by the therapy device 110, based on a performance of the user. In some instances, for example, when the score generator 143 determines, during a multi-sensory experience or exercise, that the user data 137 (e.g., sensor data), the setting data 138, and/or drug data 139 of a user are indicative of meeting a criterion (e.g., progressing towards the goal or moving away from the goal), the difficulty model can advance, regress, or change the multi-sensory experience or exercise for the user. In one example, the difficulty model can change a threshold score to advance or regress in a gameplay of the multi-sensory experience or exercise based on the indication of state (also referred to as the "score") of the user, calculated by the score generator 143. In some implementations, the processor 132 can optionally execute a setting selection model (not shown) that can adaptively select a setting(s) and subsequently update, via the profile updater 144, a subject profile based on a mental state response(s) of the user to various digital settings presented to user.

The presenter 147 of the compute device 130 can be operatively coupled to an auditory interface, a visual interface, an olfactory interface, a gustatory interface, and/or a haptic interface. In some embodiments, the presenter 147 can be operatively coupled to the therapy device 110, which can include an auditory interface, a visual interface, an olfactory interface, a gustatory interface, and/or a haptic interface. In some implementations, the presenter 147 can be configured to present, using the therapy device 110 and/or other sensory element presenting device, a scene including one or more objects to a user. The one or more objects can be, for example, one or more visual, olfactory, gustatory, auditory, or haptic signals or elements. In some implementations, the presenter 147 can show a progress of meditation, attention, and/or relaxation states of the user (e.g., by providing feedback). For example, the presenter 147 can be coupled to a virtual reality interface, an augmented reality interface, a visual display interface, a projection system interface, a speaker/headphones interface, or a haptic interface that show/convey a progression of the user to the user. In addition, or alternatively, in some implementations, the presenter can provide a guidance to the user, such as to feed-forward, e.g., to display arrow(s) or other instructions to drive or advance a state of a gameplay (or other experience or exercise) toward an end-goal. In some implementations, however, the presenter 147 can be configured to be silent (e.g., about feedback or feedforward to the user) so that the therapy system can adapt to the user in a way that changes the user's mental state whether the user is actively aware of the user's mental state or not.

The therapy device 110 (also referred to as the "training device") can include, but is not limited to, a virtual reality or VR device (e.g., Oculus VR™, HoloLens™, Muse™ 2016 brain-computer interface (BCI) device, HP Reverb G2™, etc.), an augmented device, a projection system (e.g., including a projector and a screen), a display device (e.g., a television screen), a display system (e.g., aggregated monitors connected and managed by a controller), an auditory device (e.g., a speaker and/or a headphone), an auditory system (e.g., an immersive audio and/or binaural sound system including multiple speakers and controlled by a controller), a haptic device, a olfactory virtual reality device(s), a light system(s), a strobe light(s), a tactile vest, a scent delivery system, and/or a haptic system (e.g., multiple haptic devices for various part of the body of the user). In use, the therapy device 110 can be modified to adapt to an appropriate setting(s), e.g., advance to next exercise difficulty (for sequential difficulty levels), and/or adapt to an appropriate exercise difficulty (for non-sequential difficulty levels) based on data collected by the sensor 120 and/or instruction generated by the compute device 130 based on that data. In some instances, a difficulty of the exercise of the therapy device 110 can stay the same but advance, for example, within a single-level or portion of the meditation game. The advancement through the same difficulty level can be reflected, for example, in a visual change toward a positive direction, a visual change of color, a visual change of scenery, an auditory change of a music, and/or a change in a vibration. In some embodiments, a multi-sensory experience or exercise may not include any levels. For example, a user may advance through different portions or checkpoints of an exercise, e.g., depending on a user's ability to focus and/or relax. In some embodiments, a multi-sensory experience or exercise may last for a predetermined period of time and conclude after that predetermined period of time, regardless of whether a user has advanced or progressed during the experience or exercise.

The therapy device 110 can be operated by the user and can be operatively coupled to the compute device 130 to receive data and/or instruction from the compute device 130. For example, in some instances, the therapy device 110 can receive signals (e.g., radio frequency (RF) signals, optical signals, and/or electrical signals) from the compute device 130 (e.g., from the score generator 143, the configurator 145, and/or the presenter 147). The signal from the compute device 130 can indicate whether the user data (received from the sensor 120) include the information indicative of attention, relaxation, or another mental state. The therapy device 110 can be modified/configured not to operate when the signal from the compute device 130 indicates that the user is not participating and/or ready for a therapy session (e.g., if sensor data does not contain necessary information to make a determination of the user's mental state). In another example, the therapy device 110 can receive signals from the compute device 130. The signal from the compute device 130 can also indicate at least one score in an exercise level or a progression in that exercise level.

In use, the therapy system 100 can be used in a pre-drug or procedure session and/or a in-drug or procedure session. For example, the therapy system 100 can be used for a psychedelic treatment before and/or during (e.g., for inducing and maintaining a desired or optimal set for a user) administration of a psychedelic drug. The therapy system 100 can run content such as an exercise and/or experience (e.g., including a set of visual content, a set of audio content, a set of haptic signals, a set of olfactory content, or a set of gustatory content) using the therapy device 110. The sensor(s) 120 can acquire sensor data during the exercise and/or experience and using, for example, a set of electrodes to head of the user that measure physiological activities and/or behavioral activities including, but are not limited to, EEG, electrooculography, heart rate, heart rate variability, galvanic skin response, respiratory rate, pulse oximetry, EKG, eye movements, facial expressions, glucose, pupillometry, and/or the like. The sensor data evaluator 142 of the compute device 130 can receive the sensor data from the sensor(s) 120 and determine whether the sensor data includes information indicative of optimal set functions used for developing the optimal or a suitable set for a psychedelic experience. For example, the sensor data evaluator 142 can measure impedance of the set of electrodes connected to the head of the user and determine whether the measured impedance values are within a threshold interval.

In some implementations, the processor 130 can further include a notifier (not shown) that can generate a notification (e.g., a message and/or a signal in response to receiving sensor data from the sensor(s) 120). In some instances, for example, the notifier (not shown) can send a signal to cause the compute device 130, the sensor(s) 120, and/or the therapy device 110 to show a red light (e.g., using a light emitting diode or displayed on the therapy device 110) to prompt user to fix a probe (e.g., an EEG probe) in response sensor data evaluator 142 indicating the sensor data provided by the sensor(s) 120 is not suitable (e.g., has an impedance outside a predetermined impedance interval) for determining a state of the user. In some instances, for example, the notifier (not shown) can send a signal to cause the compute device 130 and/or the therapy device 110 to show a message (e.g., generated by the processor 132) to provide specific guidance to the user about adjusting and/or changing a configuration of the sensor(s). For example, the notifier can send a message to the therapy device 110 directing the user to sit and/or stand at a certain distance (e.g., a meter) from the sensor(s) 120 to reduce noise in the sensor data.

The score generator 143 can receive the sensor data to determine (e.g., using a specialized machine learning model for a specific psychedelic compound and/or its expected effects on treatment response) an indication of state of the user (e.g., a score) representing an assessment of the user's response to the psychedelic treatment and/or a current state of an adaptive setting (e.g., a set of parameters of the multi-sensory experience or exercise that can be adjusted/tuned and/or a difficulty level) of the multi-sensory experience or exercise. Therefore, in some instances, the score generator 143 can determine whether a current state of the adaptive setting is successful in inducing or maintaining an optimal set. In some implementations, the therapy device 110 can include a feedback system indicator to display, to the user, an indication of the user's mental state in response to the current state of the adaptive setting. The feedback system indicator could be in a visual format, auditory format, olfactory format, gustatory format, and/or haptic format. In some implementations, the therapy system 100 can include a feedback component(s) (e.g., models implemented in the compute device 130) that could be auditory, visual, gustatory, olfactory and/or haptic to reflect back to individuals' their current calculated score. In some implementations, the therapy system 100 can include a feedforward reward response component(s) (e.g., models implemented in the compute device 130) to guide and drive individuals towards the target mental state. In some implementations, the score generator 143 can, in addition to the sensor data, be trained based on setting data 138 (e.g., music preference), drug data 139 (e.g., drug dosage), and user data 137 (e.g., medical data received from a third-party compute device) other than the sensor data.

The compute device 130 can be configured to adaptively change or maintain the current state of the presented sensory environment (e.g., a scene and/or objects within a scene) based on the estimated score. In some implementations, the compute device 130 can further include an adaptive setting model that determines whether or not a sufficient score, as determined by the score generator 143, is achieved for the current state of the adaptive setting of the multi-sensory experience or exercise. When the user maintains a satisfactory score, as determined by the score generator 143, the setting of the multi-sensory experience or exercise can either remain the same or change in a way that is conducive to maintaining the satisfactory score. When the user does not maintain a satisfactory score, as determined by the score generator 143, the adaptive setting can be changed via changes to the multi-sensory experience or exercise (e.g., including a change(s) made to the set of visual content, the set of audio content, the set of haptic signals, the set of olfactory content, or the set of gustatory content). In some instances, the adaptive setting model can guide or actively induce/maintain optimal set in the user during a digital therapy or other presented content towards a target mental state.

In some implementations, the personalizer 148 can modify/adjust the score generator 143 to the specific needs and unique conditions of each individual. For example, the score generator 143 can include a personalized machine learning model that can be developed on data specific to the user (e.g., sensor generated during a pre-treatment session(s) and/or in-treatment session(s)). For example, in some instances, the personalizer 148 can be modified to take in the bio-signals of a user during a psychedelic experience and use this user data to train a user-specific machine learning model from the existing score generator 143.

The profile updater 144 can then receive an indication of state of the user (e.g., the score) from the score generator 143 and in response to various states of the adaptive setting. and update a user profile of the user to generate an updated user profile. The updated user profile can be stored in the memory 131. In some instances, the profile updater 144 can use the indication of state of the user to categorize the user. For example, in some instances, the profile updater 144 can search an attention score(s) or other score(s) of the user (e.g., collected previously during a training exercise) and then assign the user to a specific competency group based on the attention score(s) or other score(s). In some instances, the profile updater 144 can update the subject's profile based on a setting(s) that induces or maintains an optimal set(s) for the subject.

The configurator 145 can then update adaptive setting of the training exercise in response to the updated user profile generated by the profile updater 144. In some instances, the configurator 145 can be manually set by a professional (e.g., a physician) to modify the adaptive setting based on the score, as determined by the score generator 143. Doing so can provide a personalized adaptive setting system for the user in accordance to conditions and/or preferences of the user.

In some implementations, the user data, the setting data, and/or the drug data can be preprocessed before being processed by the compute device 130, as described herein. Preprocessing the user data, the setting data, and/or the drug data can include, but is not limited to, denoising, filtering, feature identification, feature extraction, removal of artifacts (e.g., from muscle movements, blinking, jaw clenching, etc.), and/or removal of outliers. For example, in some instances, the compute device 130 can preprocess the user data, the setting data, and/or the drug data to a numerical and fixed-size embedding for easier processing by the score generator. In another example, the sensor(s) 120 can be configured to generate a preprocessed data before sending the sensor data to the compute device 130. For example, in some instances, the sensor(s) 120 can be configured to concatenate a time record for each datum recorded by the sensor(s) 120 to generate timestamped data. the time-stamped data can be then sent to the compute device 130 for further processing (e.g., for generating a score using score generator 130).

In some instances, when the score generator 143 of the compute device 130 generates an indication of state of the user, the compute device 130 can determine a modification to the presented exercise or content based on the indication of state of the user. In one example, the modification can include, but is not limited to, stopping the exercise or content, moving to a next level of the exercise or content, moving to a previous level of the exercise or content, and/or adjusting a parameter (e.g., a volume level, or a display color) of the exercise or content. In another example, the modification can include a change in the setting(s) or a modification to the setting(s).

Although in some embodiments the therapy device 110, the sensor 120, and the compute device 130 are shown and described as singular devices, in some embodiments, the therapy system 100 can include multiple therapy devices, multiple sensors, and/or multiple compute devices. For example, in some instances, the multiple sensors can include multiple types of sensor (e.g., photo-electric sensors, cameras, acoustic sensors, heart-beat sensors, accelerometers, humidity sensors, and/or environmental sensors) that collect data associated with various aspects of a user and/or an environment of the user.

In some instances, for example, the therapy system 100 can increase the user's sense of immersion in the adaptive setting using multiple sensors and multiple therapy devices that surround the user. Increasing the user's sense of immersion can lead to more significant and profound changes in mental state and the overall psychedelic experience of the user. Therefore, the therapy system can achieve a higher level of influence and control over the overall psychedelic experience.

Although the therapy device 110 and the compute device 130 are shown as separate devices, in some embodiments, the compute device 130 and the therapy device can be a combined device that can perform functions of both the compute device 130 and the therapy device 110.

In some instances, once the therapy system 100 and/or a physician determines a target mental state(s) for an optimal set and/or an optimal setting, a metaphor(s) can be used to induce the target mental state(s) and influence behavioral outcomes. The metaphor(s) can capture a relationship between a concrete experience and cognition. In an example, the therapy system 100 can play a high tone in response to a correct behavior and played a low tone in response to an incorrect behavior from a first group. For a second group, a low tone can be played in response to a correct behavior and a high tone in response to an incorrect behavior. In some instances, individuals in the first group, on average, can adopt correct behavior better than the second group. This is because intuitively humans tend to view a higher tone in contrast with a lower tone as the more positively reinforcing sound. Therefore, there are sensory experiences that the user can inherently link with prior experience. In the above example, the metaphor is the link between high/low sounds and the idea of correctness/wrongness. Given the above, a setting can encapsulate an appropriate metaphor that the user can associate with the correct mental state.

In another example, an experience of meditation is often described as one of stillness. Specifically, that the experience of meditation is one in which a practitioner goes from being inundated with perceptions, thoughts, and stimuli to one of consistency, stillness and oneness. As such, an appropriate metaphor employed to intuitively convey a sense of an increasingly meditative state (a possible example of an optimal mental state), can convey a sense of moving towards stillness and away from overstimulation.

In some embodiments, the compute device 130 processes can exclude one or more of the processes shown in FIG. 1. In other words, one or more processes executed by the processor 132 can be optional. For example, the compute device 130 processes can exclude the profile updater 144, the configurator 145, and the personalizer 148. As a result, the compute device 130 generates a score that is an estimated measure of progression of the multi-sensory experience or exercise using a global classifier model. Additionally or alternatively, the compute device 130 does not automatically update the user profile or configure a difficulty level of a multi-sensory experience or exercise.

In some embodiments, the therapy system 100 can be modular to keep the therapy system 100 flexible in providing a wide variety of potential settings from an auditory, visual, olfactory, gustatory and haptic perspective, the whole system can be modularized. Specifically, the therapy system 100 can allows new components to be easily added in or other components to be easily removed. Modularization of the therapy system can have a number of benefits including, but not limited to (A) improving or modifying core game mechanics to drive better outcomes, (B) improving or modifying score generator to target a wider variety of mental states or improve accuracy for existing mental states, (C) enabling the implementation or modification of settings in addition to adding new perceptual technologies, or (D) improving optimizer and configurator as new insights are gained. In one example, a head-tracked parallax visual displays can be considered, instead of a 3D-projection mapping. In another example, the processes of the compute device 130 can be implemented at a first compute device and a second compute device separate from the first compute device and that is operatively coupled to the first compute device. For example, the first compute device can include the sensor data evaluator 142 and the second compute device, that is separate from and operatively coupled to the first compute device, can include the personalizer 148.

In some embodiments, the therapy system 100 can include or implement one or more software applications, e.g., associated with one or more of the therapy device 110, the compute device 130, and/or a therapist or healthcare individual. For example, the therapy system 100 can implement, via the therapy device 110 and/or compute device 130, a virtual reality (VR) meditation application, a VR game application, a therapist web application, and/or a BCI application. The BCI application can be configured to host or implement a classifier (e.g., score generator 143), which can be configured to determine a state of a user (e.g., attention or focus, relaxation, etc.) based on user data (e.g., EEG data, HRV data, etc.). The VR meditation application can be configured to receive data from an EEG device (or other sensor(s)) and send the data for processing (e.g., by sensor data evaluator 142). The VR game application can be configured to render one or more scenes, objects, and/or other elements including visual, audio, haptic, gustatory, and/or tactile signals. The therapist web application can be configured to allow a healthcare professional or therapist to initiate, manage, and/or track a session including a multi-sensory experience or exercise.

Figure 2:
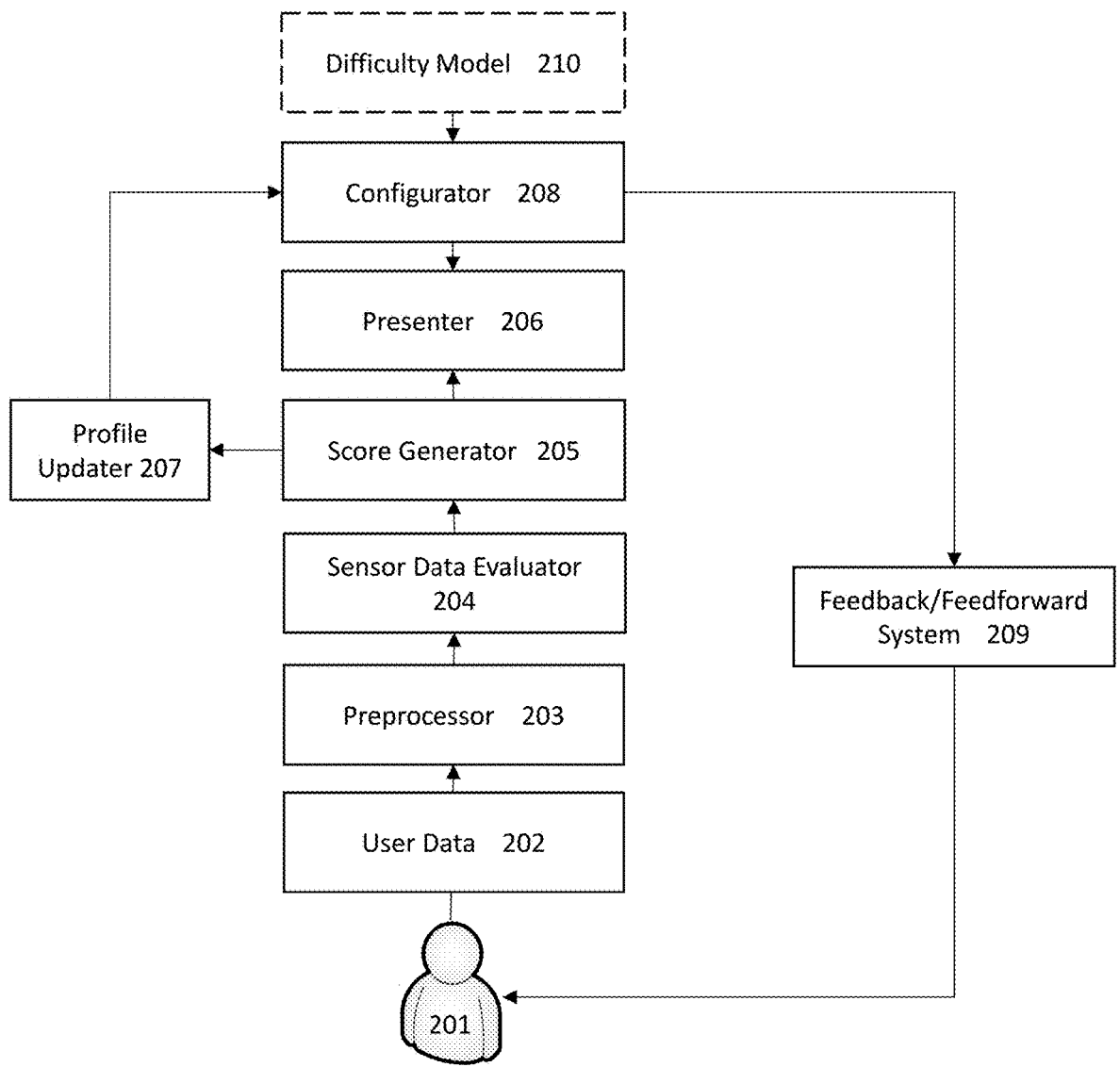
FIG. 2 is a flow chart illustrating the flow of data between components of a therapy system, according to an embodiment.

FIG. 2 is a flow chart illustrating the flow of data between components of a therapy system, according to an embodiment. The components of the therapy system, as depicted in FIG. 2, can be structurally and/or functionally similar to one or more component(s) of the therapy system 100 described above with reference to FIG. 1. For example, user data can be acquired via input devices, such as therapy device 110 and/or sensor 120.

The flow of data and/or functions associated with the therapy system 100 can include presenting multi-sensory experience or exercise such as a digital therapy (e.g., a set of visual content, a set of audio content, a set of haptic signals, a set of olfactory content, or a set of gustatory content) to a user 201 before and/or during administration of a drug including, but not limited to, for example, a psychedelic drug, including, but not limited to, for example, Psilocybin, Ketamine, Esketamine, R-Ketamine, RL-007 (e.g., for schizophrenia), Ibogaine, Deuterated Etifoxine, N-Acetylcysteine, methylenedioxy-methylamphetamine (MDMA), N-methyl-1-(3,4-methylenedioxyphenyl)propan-2-amine), methylenedioxy-methylamfetamine, 3,4-methylenedioxymethamphetamine, 3,4-Methylenedioxyamphetamine (MDA), Salvinorin A, Deuterated Mitragynine, Noribogaine, Dimethyltryptamine (DMT), N,N-DMT, D-Cycloserine, psychedelics, antidepressants, fluoxetine, sertraline, paroxetine, citalopram, venlafaxine, benzodiazepines, valproate, lithium carbamazepine, tiagabine, buspirone, barbiturates, diltiazem, or other drugs with acute central nervous system effects. The therapy system can collect data including user data, setting data, and/or drug data from the user during the presentation of the multi-sensory experience or exercise. The user data can include sensor data 202 (e.g., EEG data, heart rate variability (HRV) data, heart rate data, and/or galvanic skin response (GSR) data) that can be collected from the user using one or more sensors (e.g., the sensor(s) 120 shown and described in FIG. 1) and during the presentation of the multi-sensory experience or exercise.

Figure 6:
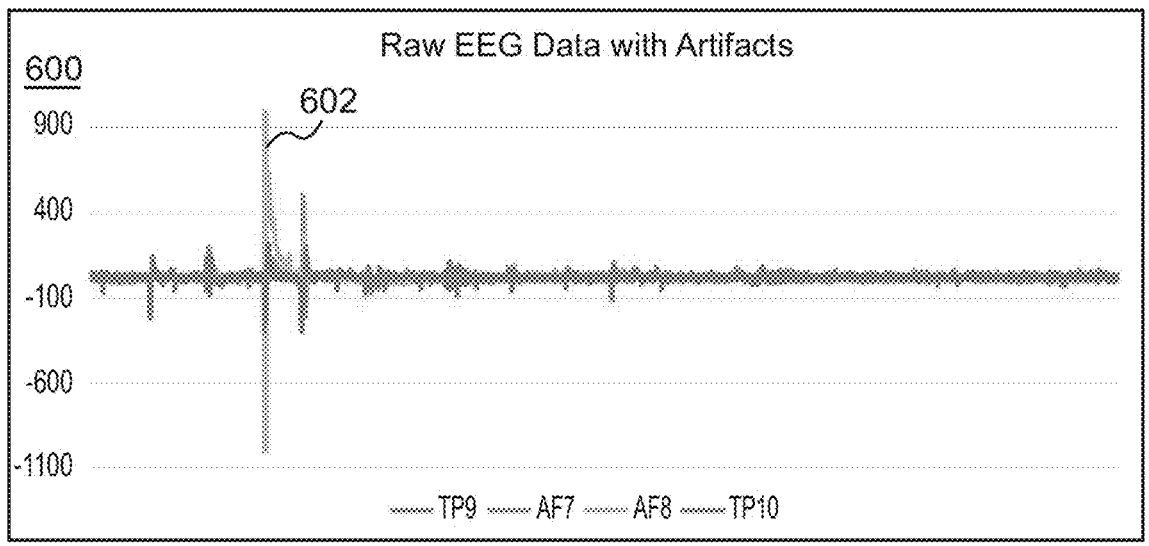
FIG. 6 is a graph of raw electroencephalography (EEG) data including artifacts.
Figure 7:
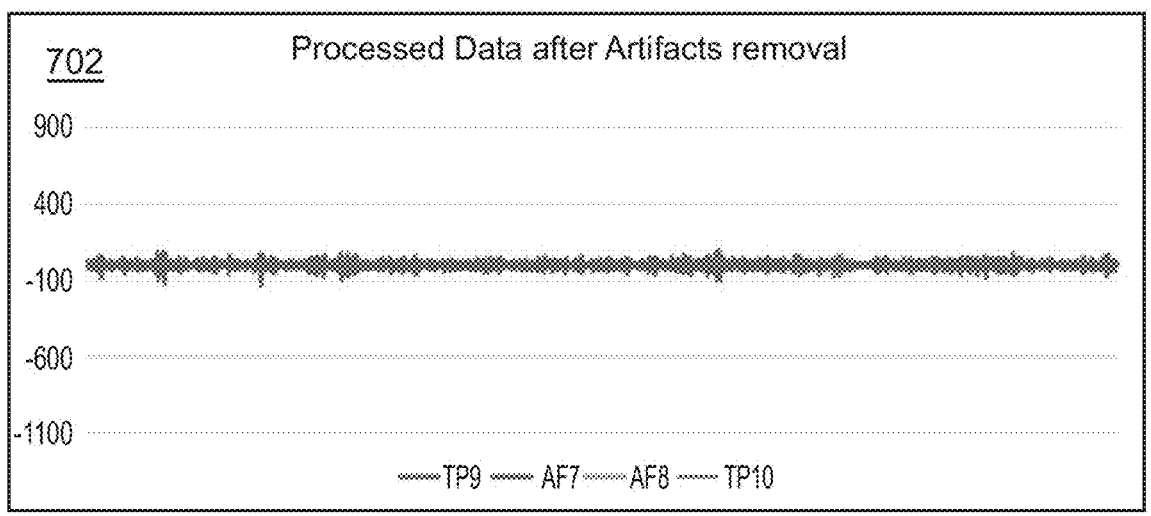
FIG. 7 is a graph of EEG data after preprocessing to remove the artifacts, according to an embodiment.

The user data, the setting data, and/or the drug data can be preprocessed and/or filtered using a preprocessor 203 before further processing and/or analysis by the therapy system. For example, in some instances, the preprocessor 203 can normalize each datum from the user data, the setting data, and/or the drug data to a numerical and fixed-size embedding for easier processing by a machine learning model (e.g., score generator 205) of the therapy system. FIG. 6 depicts an example of raw EEG data 600 from a user that includes artifacts. The artifacts (e.g., artifact 602) in the EEG data can interfere with proper analysis of the EEG data and therefore determination of a score indicative of a state of the user. Examples of artifacts can include noise and/or error in measuring user data. Accordingly, preprocessing can be performed, e.g., via preprocessor 203, to remove the artifacts. FIG. 7 depicts an example of the EEG data 702 after the artifacts have been removed via preprocessing. The preprocessing can include, but is not limited to, denoising, filtering, identification and/or removal of outliers.

Figure 8:
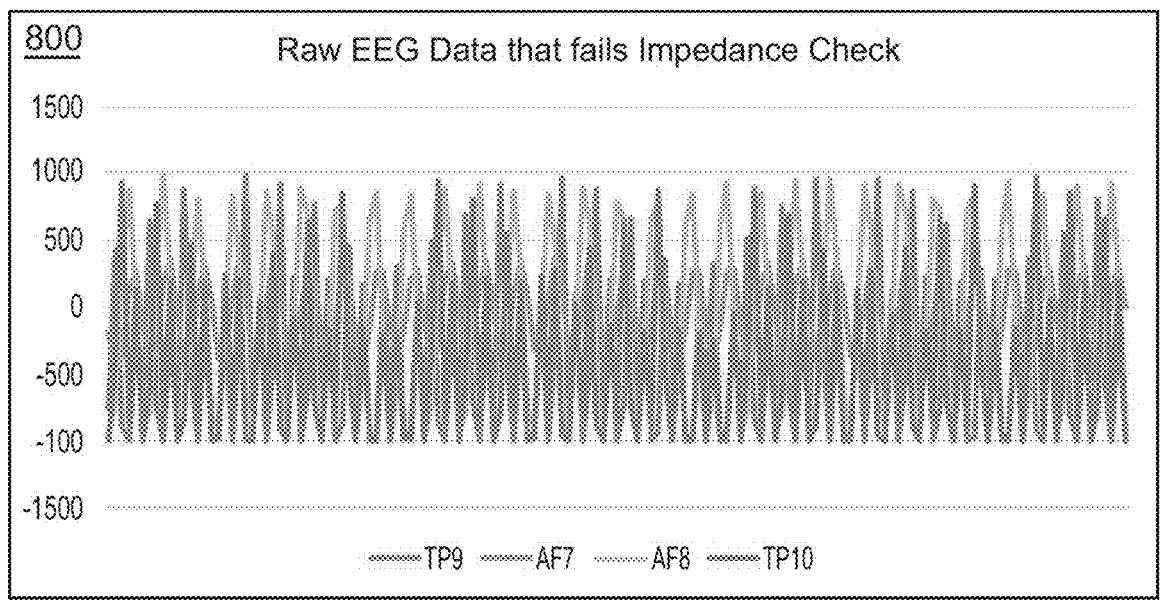
FIG. 8 is a graph of EEG data that fails an impedance check, according to embodiments.

Referring back to FIG. 2, the preprocessed and/or filtered data is sent to a sensor data evaluator 204 (similar to the sensor data evaluator 142 as described with respect to FIG. 1) to check states of data collection and then to a score generator 205 (similar to the score generator 143 as described with respect to FIG. 1) to generate an indication of state of the user. The sensor data evaluator 204 can be adapted to determine whether the preprocessed and/or filtered data meets certain predetermined criteria necessary for determining a relaxation state, an attention state, a meditation state, and/or other mental state, as described above with respect to FIG. 1. For example, as depicted in FIG. 8, EEG data 800 can be determined to not meet certain criteria, e.g., by the sensor data evaluator 204. In particular, the sensor data evaluator can determine that the EEG data 800 contains a degree of noise that make the data unsuitable for determining a user's state.

The sensor data evaluator 204 can send the preprocessed and/or filtered data approved by the sensor data evaluator 204 to the score generator 205. The score generator 205 can include a probabilistic model (e.g., the machine learning model of the score generator 143 described above with respect to FIG. 1) to determine an indication of state of the user and/or whether a portion of the exercise is successfully completed.

A presenter or feedback indicator 206 (e.g., similar to the presenter 147 shown and described with respect to FIG. 1) can be provided to illustrate to the user his or her progress in completing a portion of the multi-sensory experience or exercise. In some instances, the presenter or feedback indicator 206 can be provided to illustrate to the user his or her progress in mental state. This indicator can be provided as, for example, a visual, auditory, olfactory, gustatory, and/or haptic signal that can be presented to the user via feedback/feedforward system 209 of the therapy device (e.g., the therapy device 110 as shown and described with respect to FIG. 1). In some implementations, the presenter 206 can be configured to be silent (e.g., about feedback or feedforward to the user) so that the therapy system can adapt to the user in a way that changes the user's mental state whether the user is actively aware of the user's mental state or not.

The score generator 205 can be coupled to a profile updater 207, as described above with respect to FIG. 1. For example, the profile updater 207 is adapted to receive the generated indication of state of the user (including an indication of meditation state, an indication of attention state, an indication of relaxation state, and/or an indication of another mental state) determined by the score generator 205, and update a user profile of the user consequently in response to the indication of state. The profile updater 207 is operatively coupled to a configurator 208 that can automatically set a difficulty level of a multi-sensory exercise (e.g., a feedback-based meditation) or optimize setting selection/generation of one or more settings in response to the updated user profile as determined by the profile updater 207. Alternatively, in some instances, the configurator 208 can be manually operated by a professional to modify the difficulty level of the multi-sensory exercise or variables related to the selection/generation of settings.

Optionally, when being implemented with a multi-sensory exercise (e.g., prior to a drug treatment or session such as a psychedelic experience), a difficulty model 210 (also referred to as the "adaptive difficulty model") can be optionally coupled to the configurator 208 to advance, regress, or change a digital therapy exercise such as, for example, a relaxation therapy/training exercise, an attention therapy/training exercise, and/or a meditation therapy/training exercise, based on a performance of the user. In one example, when the score generator 205 determines, using user data 137 (e.g., sensor data), and optionally the setting data 138 and/or drug data 139, that the user is performing an exercise with a first difficulty level during a time interval shorter than a predetermined time interval, the difficulty model 210 can advance a gameplay of the exercise with the first difficulty level for the user to a second difficulty level higher than the first difficulty level. In another example, the difficulty model can regress or change the gameplay of the exercise based on the indication of state of the user (e.g., a score below a predetermined threshold) and/or a duration (e.g., the first 5 minutes or the first 10 minutes) of the gameplay, calculated by the score generator 143. Therefore, the difficulty model 210 can, for example, classify the user in a competency group from a set of competency groups (e.g., beginner, intermediate, advanced, etc.). A user in a lower/higher competency segment has lower/higher preset thresholds for completing difficulty levels, thus making it easier/more difficult to complete a difficulty level based on the user's level of competency. In some instances, the threshold score(s) are not explicitly shown to players so that the user is not be aware of what competency group they fall into and therefore there is no risk in making the user feel negative about competency.

In some embodiments, the configurator 208 can be configured to change or maintain one or more settings (e.g., of a digital therapy session) based on user data, e.g., collected by the sensor(s). The configurator 208 can be configured to change or maintain the setting(s) based on whether one or more of the settings induce or effect a certain state in the user, e.g., induce or increase an optimal state of the user. In some embodiments, the configurator 208 can be configured to change a setting in response to determining that a setting is not conducive to achieving an optimal state of the user. For example, the configurator 208 can be configured to change a visual setting, an audio setting, an olfactory setting, a tactile setting, etc. With visual settings or elements, the configurator 208 can be configured to change a position, color, shape, or other configuration of the visual setting or element. With audio elements, the configuration 208 can be configured to change an intensity, frequency, tone, volume, melody, rhythm, chords, or other characteristic of the audio setting or element. In some embodiments, the configurator 208 can be configured to maintain one or more settings while changing one or more other settings. In some embodiments, the configurator 208 can be configured to change settings based on whether a mental state or response of the user to a digital setting has reached a threshold score or value, e.g., indicative of achieving a desirable degree of a certain mental state. In some embodiments, the configurator 208 can be configured to change or maintain the digital settings during a drug session (e.g., a session for receiving a drug treatment such as a psychedelic).

In some implementations, the therapy system can further include a personalizer that can be configured to take in the bio-signals of the user during a multi-sensory experience and/or exercise session and use this user data to develop a personalized score model from an existing global score model (e.g., a pre-trained machine learning model). This can further provide a personalized training method for the user in accordance with the condition and unique signals of the user.

FIG. 3 is a flow chart illustrating the flow of data between components of a therapy system to produce a personalized classifier, according to an embodiment. The components of the therapy system, as depicted in FIG. 3, can be structurally and/or functionally similar to one or more component(s) described above with reference to FIG. 1. The flow of data and/or functions associated with the therapy system can include presenting a multi-sensory experience or exercise (e.g., such as a digital therapy) to a user 301 (e.g., before administration of a drug such as ibogaine or during administration of a drug such as ibogaine). The therapy system can collect user data including sensor data 302 (e.g., EEG data, heart rate variability (HRV) data, etc.) that can be collected from the user using one or more sensors (e.g., the sensor(s) 120 shown and described in FIG. 1).

Past user data can be collected during a first time period (e.g., a week, a month, or a year) from multiple users and be used to train a global score model 303. In some instances, the global score model 303 can be similar to the machine learning model of the score generator 143. For example, the global score model can include a deep neural network that is trained on the past user data. The global score model 303 can be executed to receive the user data not among the past user data and generate a first indication of state of the user with a first accuracy. In some instances, the first indication of state of the user can determine a progression of a user through a multi-sensory exercise (e.g., when a relaxation level, an attention level, and a meditation level of the user indicates 90% of portion or level of an exercise is complete).

A personalizer 305 can collect first user data associated with a specific user (or group of users sharing similar characteristics) during a second time period (e.g., after the first time period and training the global machine learning model). The personalizer 305 can then train a personalized score model 304 (also referred to as the "user-specific machine learning model") that is tailored to determining a state of the user. The personalized score model 304 can be executed to receive second user data (e.g., not among the first user data or the past use data) and generate a second indication of state of the user with a second accuracy larger than the first accuracy of the first indication of state of the user. For example, the first accuracy can indicate that the first indication of state of the user is about 70 percent accurate and the second accuracy can indicate that the second indication of state of the user is about 90 percent accurate which is larger than the first accuracy.

In some implementations, the personalized score model 304 can have the same or substantially similar model structure (e.g., neural network structure such as, for example, same number of layers, nodes, etc., but with different hyperparameter values) as the global score model 303. For example, in some instances, the global score model 303 can include a first neural network model with n dense layers, m temporal convolutional layers, o spatial convolutional layers, and p drop out layers, and use rectified linear unit (ReLU) activation functions, that are trained using past user data to generate a trained global score model. The personalized score model 304 can also include a second neural network model with n dense layers, m temporal convolutional layers, o spatial convolutional layers, and p drop out layers, and use rectified linear unit (ReLU) activation functions, that uses hyperparameters (e.g., weights, biases, etc.) from the trained global score model and the first user data to train the personalized score model 304. As a result, a trained personalized score model is produced that is structurally similar to the trained global score model but trained on additional data (e.g., associated with a specific user or group of users) and with different hyperparameters (e.g., weights, biases, etc.).

In some implementations, the personalized score model 304 can have a different model structure (e.g., neural network structure (e.g., layers, nodes, etc.)) as the global score model 303. Returning to the above example, in some instances, the global score model 303 can include a neural network model with n dense layers, m temporal convolutional layers, o spatial convolutional layers, and p drop out layers, and use rectified linear unit (ReLU) activation functions, that are trained using past user data to generate a trained global score model. The personalized score model 304 can instead include a decision tree that is trained on the first user data to produce the trained personalized score model. As a result, the personalized score model 304 is structurally different from the global score model 303. Alternatively, in some implementations, the personalized score model 304 can have a similar structure as the global score model 303 but be configured to normalize an output from the global score model 303 based on the first user data to produce personalized scores for the user.

Figure 4:
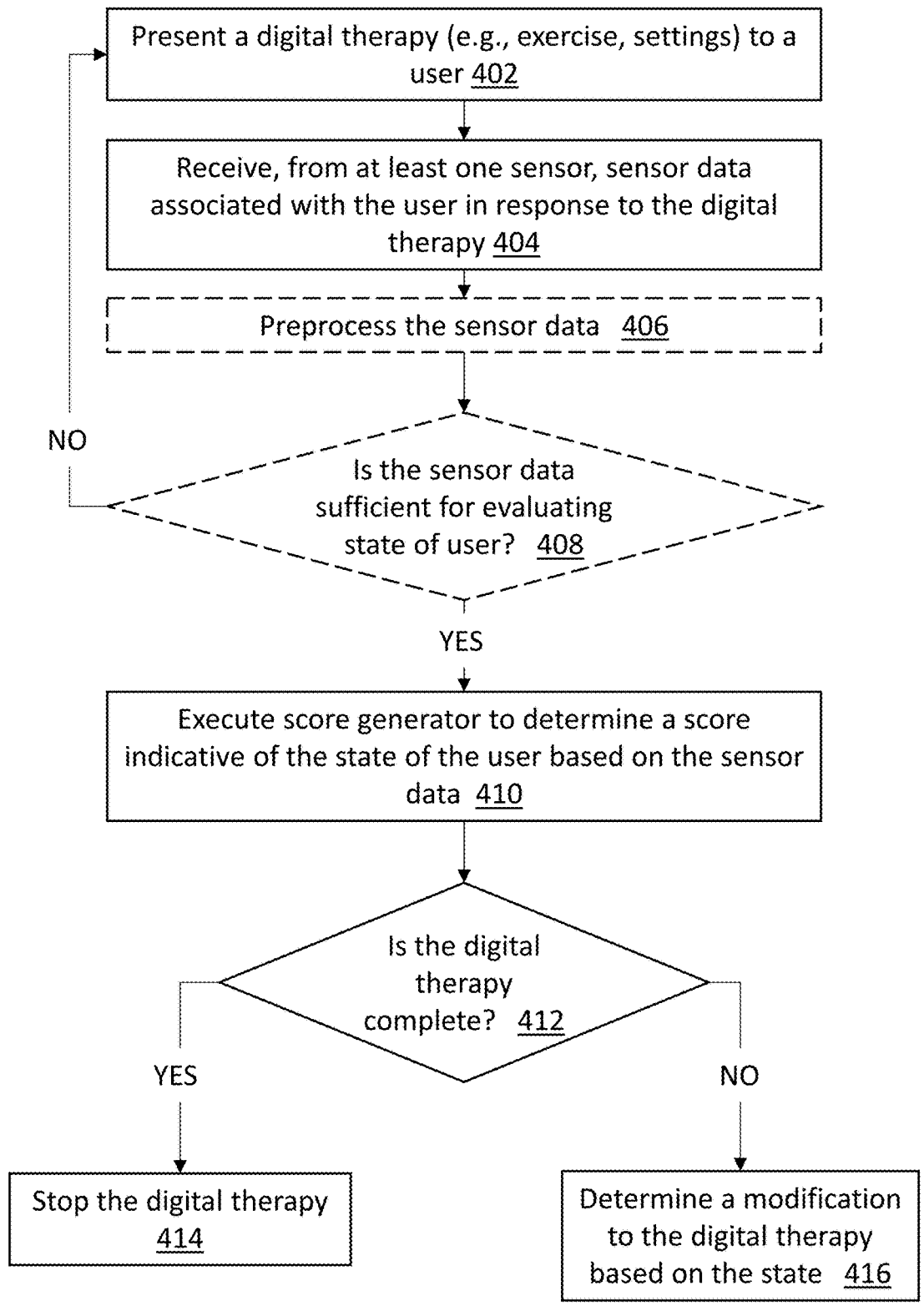
FIG. 4 is a flow chart illustrating a method of adaptive digital therapy for use with a drug treatment, according to an embodiment.

FIG. 4 is a flow chart illustrating a method 400 of an adaptive digital therapy for use with a drug treatment, according to an embodiment. In some embodiments, the method 400 can be performed by a therapy system that is structurally and/or functionally similar to the therapy system 100 as shown and described with respect to FIG. 1, and/or include elements that are similar to those described with respect to FIGS. 2 and 3. At 402, a digital therapy is presented to a user (e.g., before or during an acute experience and/or administering the drug). The digital therapy can be presented to a user via a therapy device similar to the therapy device 110 as shown and described with respect to FIG. 1. At 404, sensor data associated with the user is received in response to the digital therapy and from at least one sensor. The at least one sensor can be configured to measure, for example, electroencephalography (EEG), electrooculography, pulse oximetry, electrocardiogram (EKG), respiratory rate, eye movements, pupillometry, glucose, and/or galvanic skin response.

At 406, the sensor data can be optionally preprocessed. For example, in some instances, the therapy system can normalize the sensor data to a common scale, and/or a common format, for a streamline processing of the sensor data. At 408, it can be optionally determined whether the sensor data (the sensor data as received from the sensor or the preprocessed sensor data) is sufficient for evaluating a state of the user. For example, in some instances, the therapy system can determine whether an absolute value of the sensor data has an amplitude above a predetermined amplitude threshold, has a signal-to-noise ratio (SNR) above a predetermined SNR ratio, and/or is measured over a time interval longer than a predetermined threshold. In some instances, when the sensor data is indicated as insufficient for evaluating a state of the user, the therapy system can continue presenting the digital therapy to the user. In some instances, when the sensor data has been indicated as insufficient for evaluating a state of the user, the therapy system can pause the digital therapy until a correction(s) are made. When the sensor data is sufficient for evaluating a state of the user, the therapy system can then execute a score generator (e.g., similar to the score generator 143 as shown and described with respect to FIG. 1).

At 410, the score generator (e.g., a machine learning model) is executed to determine a score indicative of the state of the user based on the sensor data. The score generator can receive the sensor data (or the preprocessed sensor data) and perform, for example, a set of arithmetic operations and/or logical operations, determined by a set of parameter of the score generator, on the sensor data to determine the score. In some instances, the score generator can also generate a confidence score for the score generated. At 412, the indication of state of the user can be assessed (e.g., be compared to a predetermined threshold value) to determine whether the digital therapy is complete or progressing. In some instances, the indication of the state of the user together with the confidence score for the indication of state of the user can be used to determine whether the digital therapy is complete. In some implementations, the indication of state can be assessed to determine a measure of progression toward optimal mental state in response to the digital therapy. For example, in some instances, the digital therapy can have no indication of progression within the digital therapy. Therefore, progress in this context can be a measure of mental state response to a digital setting.

In some instances, when a percentage value of a difference between a numerical value representing the indication of state of the user and the predetermined threshold value is less than a preset limit such as, for example, 5%, 4%, 3%, 2%, or 1%, the therapy exercise can be deemed complete and the digital therapy can be stopped (at 414). In another example, when the percentage value of the difference is above the preset limit, the digital therapy can continue with a modification to the digital therapy based on the state (at 416). In yet another example, while the percentage value of the difference between the numerical value representing the indication of state of the user and the predetermined threshold value is less than 5%, the confidence score of the indication of state can be low (e.g., 50%, 40%, 30%, 20%, or 10% confidence on the estimated score) and therefore the digital therapy can continue. In some instances, when the confidence level of the indication of state of the user is low, the therapy system can notify an administrator, a therapist, and/or a physician, for example, to manually determine a state of the digital therapy or confirm safety of the user under the digital therapy.

At 416, a modification to the digital therapy can be determined based on the indication of the state of the user. As a result, a signal indicating the modification in a presentation of the digital therapy can be sent to the therapy device. The modification can include, but is not limited to, stopping the digital therapy, moving to a next level of digital therapy, moving to a previous level of digital therapy, and/or adjusting a parameter (e.g., a volume level or a display color) of the digital therapy.

Figure 9A:
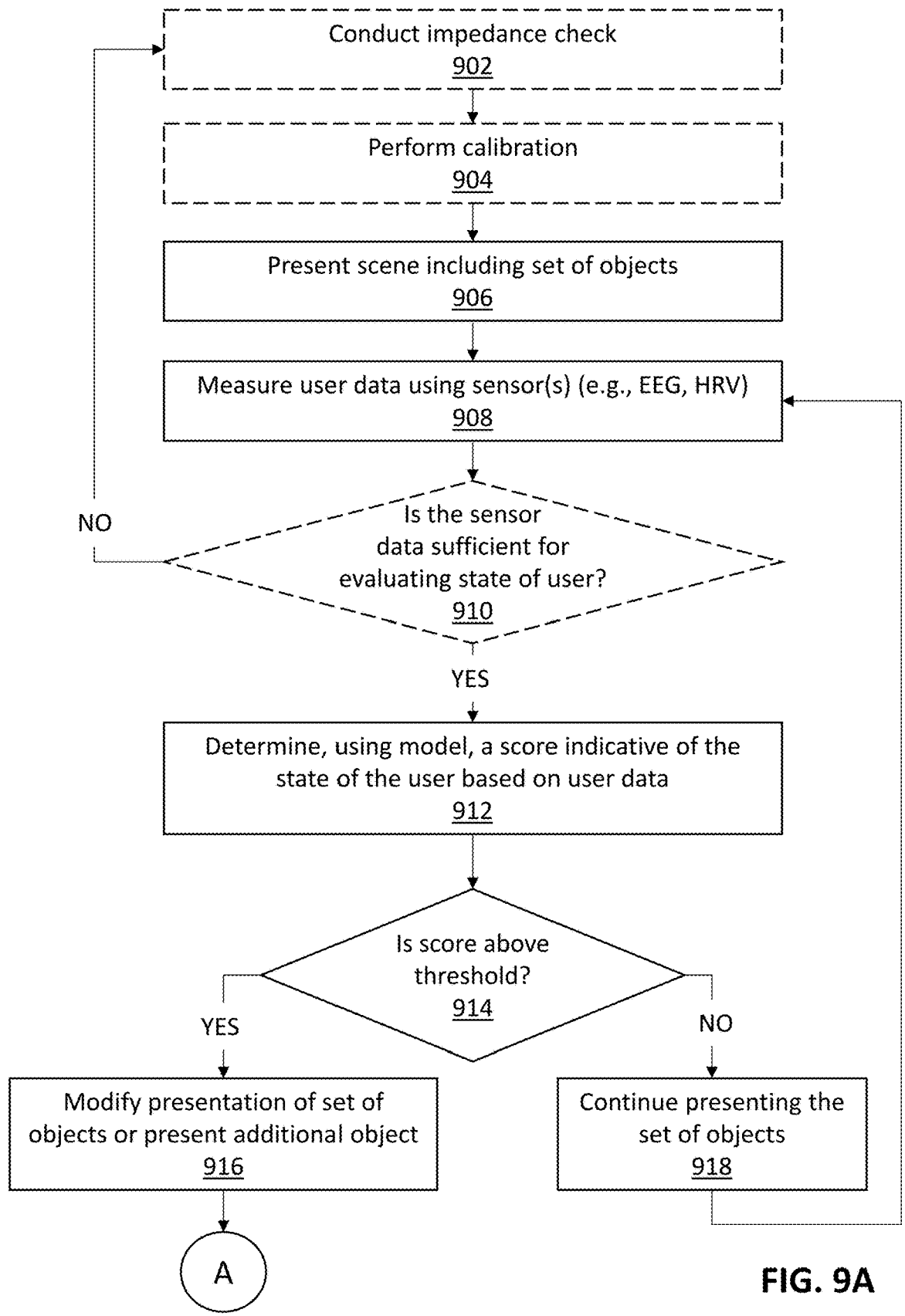
FIGS. 9A and 9B depict a method of implementing a feedback-based meditation program, according to embodiments.
Figure 9B:
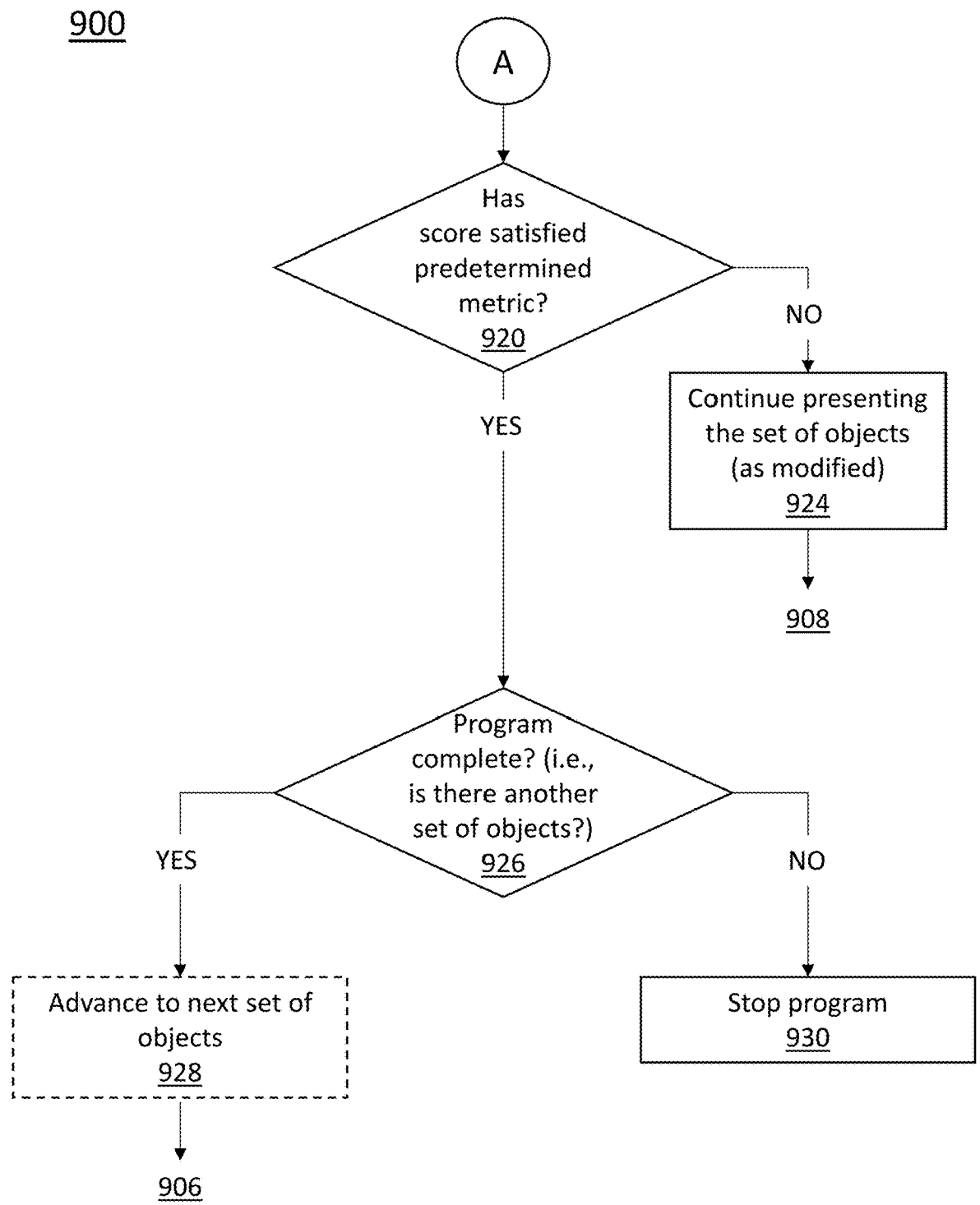

FIGS. 9A and 9B are flow charts illustrating a method or process 900 of implementing a feedback-based meditation program (e.g., a multi-sensory exercise or digital therapy), according to embodiments. In some embodiments, the method 400 can be performed by a therapy system that is structurally and/or functionally similar to the therapy system 100, as shown and described with respect to FIG. 1, and/or include elements that are similar to those described with respect to FIGS. 2 and 3.

In some embodiments, a feedback-based meditation program can be performed, e.g., via a gameplay. A specific example of a gameplay for preparing a user to have an optimal set or suitable mindset for receiving a psychedelic is described below under the heading "Example 1." The feedback-based meditation program can be performed, for example, prior to a user receiving a drug treatment, undergoing a medical procedure or medical exam, and/or experiencing a condition or setting without a drug (e.g., pain, anxiety, etc.).

In an example embodiment, a user can visit a clinic, e.g., for receiving a drug treatment or therapy. The user can undergo a pre-treatment session involving a feedback-based meditation program. In some embodiments, the user may be instructed to wear a BCI device, EEG device, and/or a PPG device. The BCI device, EEG device, and/or PPG device can be an example of a sensor 120. At 902, an impedance check can optionally be performed, e.g., to confirm that the BCI device or EEG device has been properly placed on the user. For example, one or more electrodes of the BCI device or EEG device can be activated to measure signals across those electrodes. The signals measured by those electrodes can be sent to a compute device (e.g., compute device 130), which can process the signals to determine whether their values fall within a predefined range that is indicative of proper placement of the BCI device or EEG device. In some embodiments, if the value of any signal falls outside of the predefined range, then the compute device can be configured to alert a healthcare professional or therapist that a particular electrode has not been properly positioned, e.g., by controlling the BCI device or EEG device (or sending an instruction to the BCI device or EEG device that causes the BCI device or EEG device) to light up the particular electrodes that have not been properly placed or to light up those electrodes in a different color from the remaining properly positioned electrodes. For example, the electrodes that have been properly positioned can be indicated with a green light, and the electrodes that have not been properly positioned can be indicated with a red light. In some embodiments, a display on a compute device (e.g., the compute device 130 or a separate compute device associated with a healthcare professional or therapist) can be configured to indicate which electrodes have not been properly positioned. The healthcare professional or therapist can then adjust the BCI device or the EEG device until the electrodes are properly positioned on the user's head.

At 904, a calibration can optionally be performed. For example, the user can be assigned a pre-game calibration task, which can enable the BCI device or EEG device to be calibrated or set to the specific user's brain activities. In some embodiments, data collected during the calibration can be used to uniquely adapt a model to be a user-specific model, as described above with reference to FIG. 3. In an example, the calibration can involve audio guidance (e.g., through a calm and relaxing voice) to assist the user in entering a state of relaxation. In some embodiments, the audio script can be based on induction techniques employed in hypnosis, such as, for example, the staircase method. In some embodiments, the user can be given a looping or repeating animation that the user can be asked to focus on. As the user proceeds through the induction process, the user's EEG data and other data can be collected and used to update the global classifier. The calibration phase can continue and be repeated before beginning a gameplay.

Figure 11A:
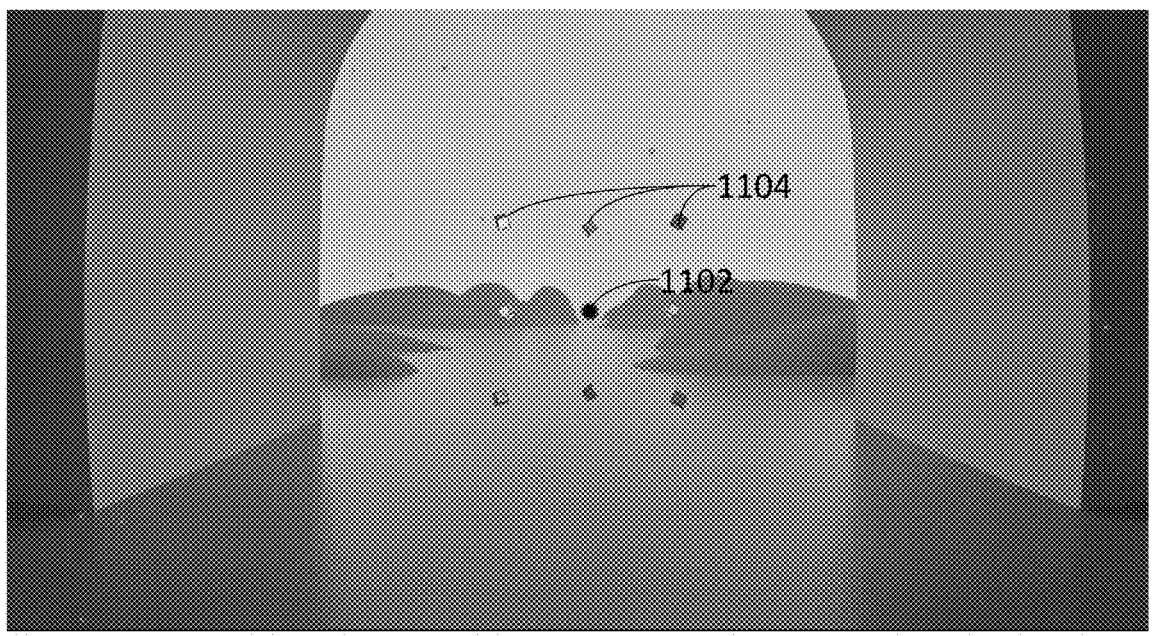
FIGS. 11A-11E depict different stages or points in an example scene used in a feedback-based meditation program, according to embodiments.

The gameplay or feedback-based meditation program can then initiate. At 906, a scene including a first set of objects can be presented. The user can be seated in a dark space, while one or more sensory elements (e.g., visual, audio, haptic, tactile, gustatory) can be presented to the user. For example, a combination of sound and visual elements can be presented. In some embodiments, the scene can be one of the example scenes depicted in FIGS. 11A-14D. For illustrative purposes, 906-930 are described with reference to a first example scene 1100, as depicted in FIGS. 11A-11E. FIGS. 11A-11E depict the scene 1100 as the user progresses through the gameplay. In FIG. 11A, the scene can begin with a first set of objects 1102, 1104. The user can be instructed to focus or relax. With respect to the scene 1100, the user can be instructed to focus on a black circle or dot 1102 (e.g., an object) in the center of the scene. While a black dot 1102 is provided with resect to the scene 1100, it can be appreciated that in other embodiments, different objects (e.g., a visual element, an audio element, a haptic element, a gustatory element, or a tactile element) can be presented to the user for the user to focus on. In some embodiments, the user may be generally instructed to focus or relax, e.g., by focusing on the user's breathing or another activity, by focusing on the user's body or self, etc. As such, in some embodiments, no object (e.g., no black dot 1102 or other object) may be provided to a user to focus and/or relax.

While the scene is being presented and the user is focusing on the black dot 1102, the BCI device or EEG device (and/or other sensors, e.g., sensor(s) 120) can be configured to measure user data, including, for example, EEG data, HRV data, etc., at 908. The user data can be sent from the BCI device or EEG device to a compute device (e.g., compute device 130), and the compute device can process the user data. At 910, the compute device can determine whether the sensor data is sufficient for evaluating a state of the user, e.g., as described above with respect to FIGS. 6-8.

If the data is not sufficient for evaluating the state of the user, then the process can return to 902. If the data is sufficient for evaluating the state of the user, then at 912, the compute device, e.g., implementing a score generator (e.g., score generator 143), can use a model to determine a score that is indicative of the state of the user based on the user data. In particular, the compute device can input the user data into the model, which can generate an output that is or is indicative of the score of the user. The model, as described with respect to FIG. 3 above, can be a classifier such as, for example, a global score model 303 or a personalized score model 304. The score can be based on or indicative of a measure of focus and relaxation of the user, e.g., as determined based on the user's EEG data, HRV data, and/or other data.

Figure 11B:
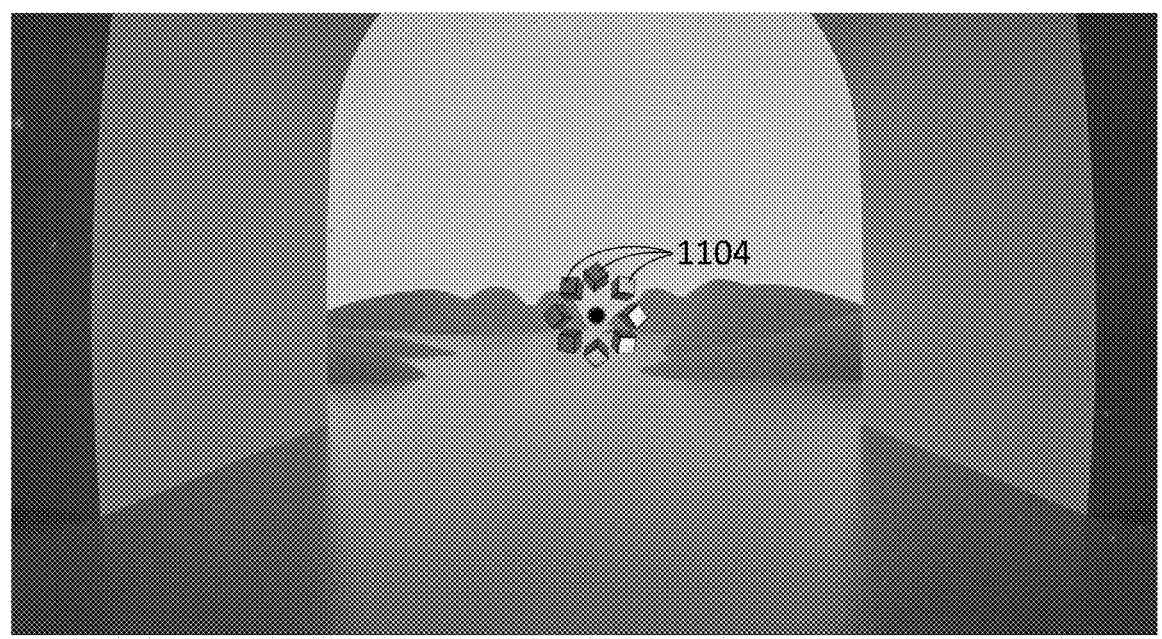

While the scene 1100 is being presented, the compute device can repeatedly or periodically at intervals (e.g., between about 1 microsecond to about 10 seconds, including all subranges and values therebetween, including, for example, each 1 second), continue to collect user data, at 908, and determine a score of the user, at 912, e.g., to monitor the state of the user. In particular, after determining each score, the compute device can determine whether the score is above a threshold, at 914. When the user's score is above the threshold, the presentation of the first set of objects can be modified, at 916. For example, the first set of objects 1104 can move toward forming a pattern, such as, for example, a ring. FIG. 11B depicts the first set of objects 1104 forming a first ring. Alternatively or additionally, an additional object (e.g., an audio element such as a sound) can be presented, at 916. For example, as the objects move toward forming the ring in FIG. 11B, a sound can play to indicate to the user that he is progressing toward a first checkpoint (e.g., forming a first ring).

The process can then continue to 920, where the compute device can determine whether the score has satisfied a predetermined metric. In some embodiments, the score can satisfy the predetermined metric, e.g., by being above the threshold for a certain period of time. In other embodiments, the score can satisfy the predetermined metric by being a certain amount or percentage above the threshold. In some embodiments, other metrics can be used to evaluate when the score of the user, and therefore the state of the user, has progressed sufficiently, e.g., to reach a first checkpoint. When the score has not satisfied the predetermined metric, then the first set of objects 1104 can continue to be presented, at 924. If the presentation of the objects has been modified, e.g., at 916, then the objects can be presented according to their modified presentation. The process can then return to 908, e.g., as additional user data is collected for generating another score.

Figure 11C:
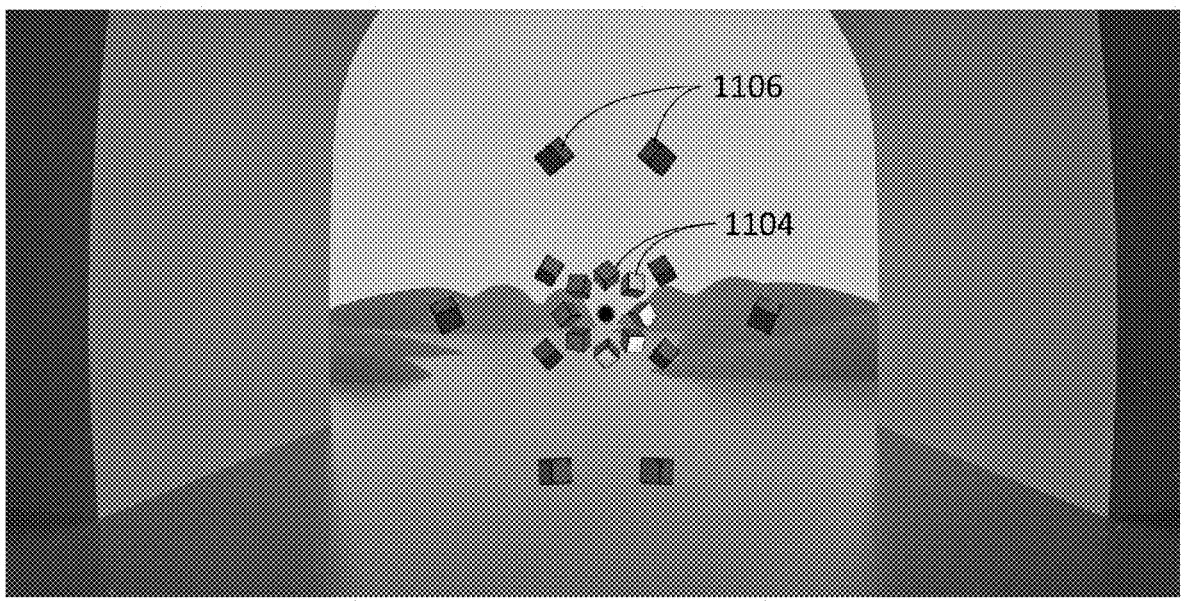
Figure 11D:
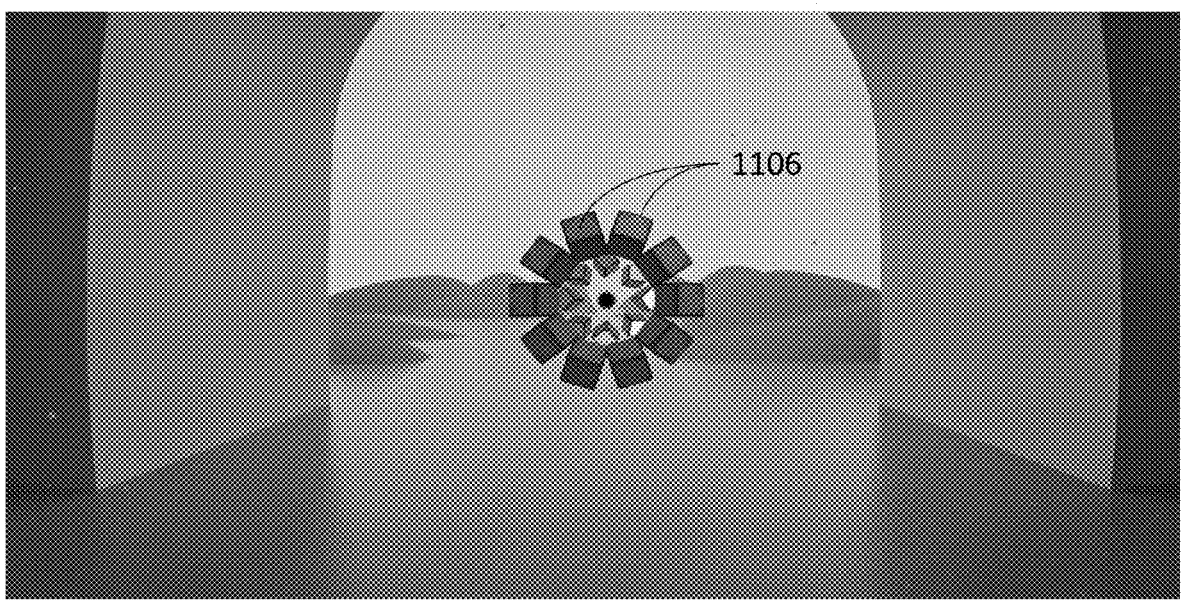

When the score has satisfied the predetermined metric, then at 926, the compute device can determine whether the feedback-based meditation program is complete. In some embodiments, the program can complete after a predetermined period of time (e.g., between about 5 minutes and about 20 minutes, including all subranges and values therebetween, including, for example, 10 minutes). In some embodiments, the program can complete after the user has progressed through a plurality of checkpoints (e.g., formed a sufficient number of rings in the example of FIGS. 11A-11E). When the program is complete, then it can stop, at 930. Alternatively, when the program is not complete, then the program can optionally advance onto a subsequent set of objects, at 928. For example, with respect to the scene 1100, when the score has satisfied the predetermined metric, then the user has reached a first checkpoint and the first set of objects 1104 may have formed a first ring as depicted in FIG. 11B. A second set of objects 1106, as depicted in FIG. 11C, can then form. The process can then repeat with the second set of objects 1106 until a second checkpoint is reached and a second ring is formed, as depicted in FIG. 11D.

Figure 11E:
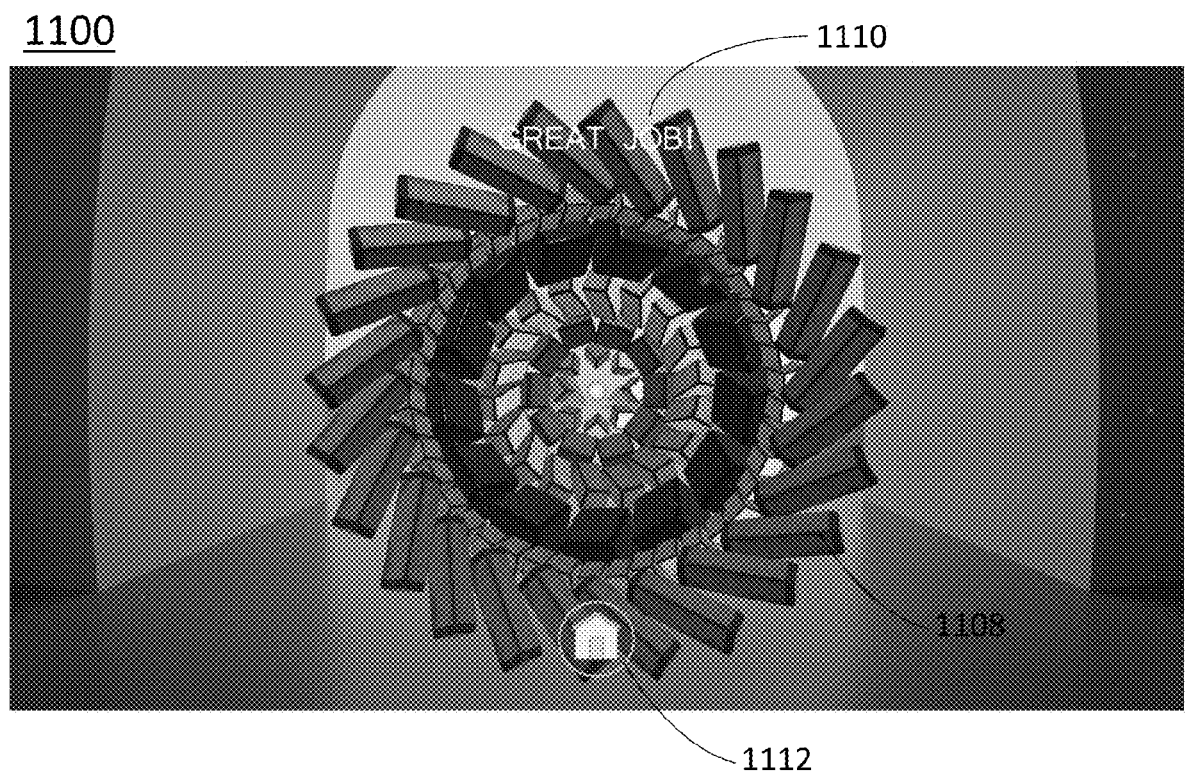

This process can continue, e.g., through a series of checkpoints where subsequent sets of objects are presented after preceding sets of objects form a pattern, until a certain number of rings have been formed, as depicted in FIG. 11E. In the example shown, this is six rings, but it can be appreciated that any number of rings can be formed. When the last checkpoint has been reached (e.g., a last set of objects 1108 has formed a ring as shown in FIG. 11E), then the process can end, at 930. In some embodiments, the scene at the end of the gameplay can include an additional object to the user. For example, the scene 1100 includes an additional visual element "GREAT JOB!" 1110. In some embodiments, the scene at the end of the gameplay can also include an icon or other user interface element that the healthcare professional or therapist can select to return to a home interface. From that home interface, the healthcare professional or therapist can then re-initiate the feedback-based meditation program, e.g., with the same user or a different user.

Referring back to 914, when the user's score is below the threshold (or sustained below the threshold), the first set of objects can continue to be presented, at 918, but in some embodiments, the presentation of the first set of objects can change. For example, the first set of objects may move toward more chaotic motion and not form any pattern. Alternatively, the first set of objects can scatter or lose its pattern. The process can continue looping or return back to 908, where additional user data is measured and then used to determine an updated score for the user. In some embodiments, the first set of objects can fade away, e.g., when a user's score remains below a threshold for a predetermined period of time.

While not depicted, it can be appreciated that the healthcare professional or therapist can halt or stop the method 900 at any stage. For example, if the healthcare professional determines that there is a safety risk or that the user is not progressing as intended, then the healthcare professional can halt the gameplay. In some embodiments, the healthcare professional can restart the gameplay with the user or the healthcare professional can select a different feedback-based meditation program with a different scene to present to the user.

When the user has completed the gameplay (or multiple gameplays), the user can be ready for receiving a drug treatment and/or a procedure. In particular, the gameplay (or multiple gameplays) can enable the user to be in a focused or relaxed state, e.g., with a suitable set for receiving the drug treatment or the procedure. For a drug treatment, e.g., involving a psychedelic, the process can continue to the method 1000 depicted in FIG. 10.

Referring now to FIGS. 12A-14D, three other examples of scenes that can be implemented as part of a feedback-based meditation program (e.g., the feedback-based meditation program described with reference to FIGS. 9A and 9B) are depicted.

Figure 12A:
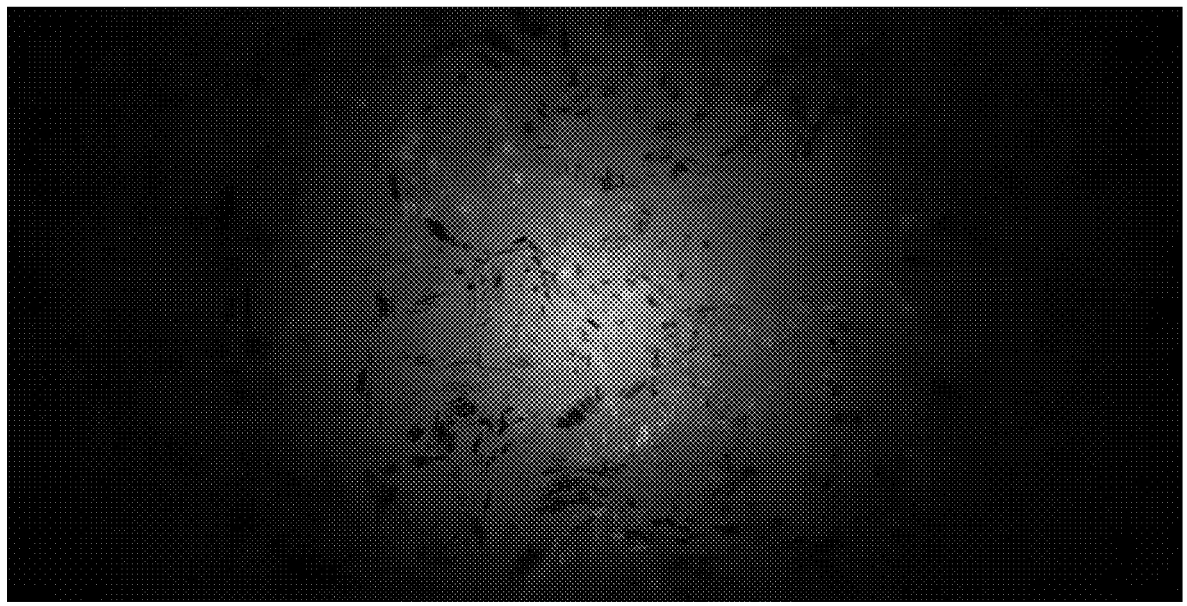
FIGS. 12A-12B depict different stages or points in another example scene used in a feedback-based meditation program, according to embodiments.
Figure 12B:
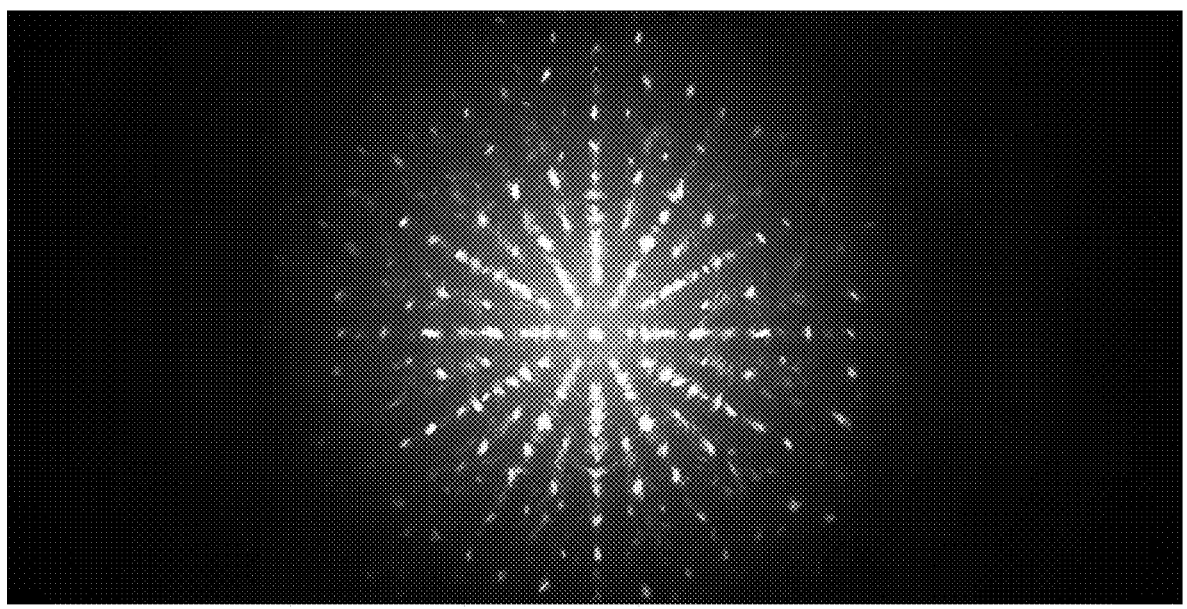

FIGS. 12A-12B depict an example scene that starts at 1200 and progresses to 1202. The scene can have objects such as particles. When the scene is initially presented (e.g., at 906 of the method 900), the particles can be randomly placed or scattered. The user can be instructed to focus or relax, e.g., to focus on his breathing, his body, or an object. One or more sensors (e.g., a BCI device, EEG device, PPG device, etc.) can be configured to collect user data after the user has been instructed to focus or relax (e.g., at 908 of the method 900). A score indicative of the state of the user (e.g., a measure of focus and/or relaxation of the user) can then be generated using a model that processes the user data (e.g., at 912 of the method 900). When the user's score is above a certain threshold, the presentation of the particles can be modified, e.g., the parties can move toward a specific pattern formation, as depicted in FIG. 12B. Additionally or alternatively, an additional object can be presented, e.g., a sound that indicates to the user that his state is optimal (or approaching optimal). When the user's score is below the threshold, then the particles can continue to be presented, e.g., in a randomly placed manner or chaotic pattern-less state. In some embodiments, once a pattern has been formed and maintained for a preset amount of time (e.g., once the user's score has satisfied a predetermined metric by, for example, remaining above a threshold for a set period of time), then the user's continuing performance above the threshold can generate a new object (e.g., a new sound) and/or move the particles toward a new pattern formation. This process can continue, e.g., through a series of checkpoints where additional patterns are formed (e.g., 906-926), until a certain number of patterns have been formed. For example, the scene can continue until the user forms four patterns. The gameplay can then end (e.g., at 930 of the method 900).

Figure 13A:
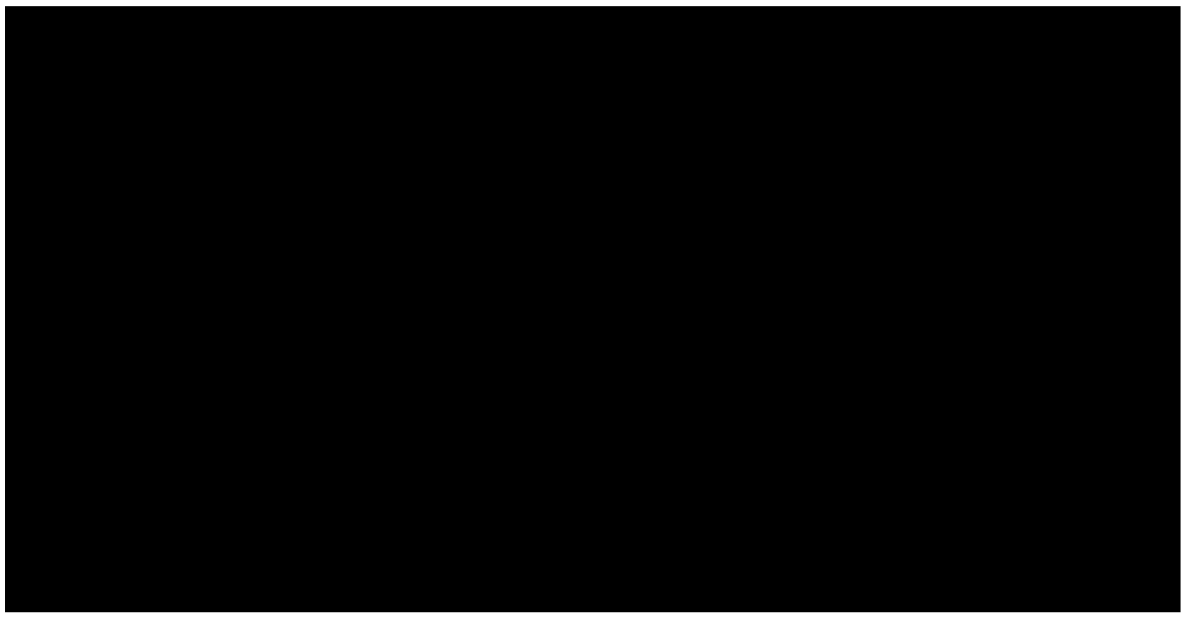
FIGS. 13A-13E depict different stages or points in another example scene used in a feedback-based meditation program, according to embodiments.
Figure 13B:
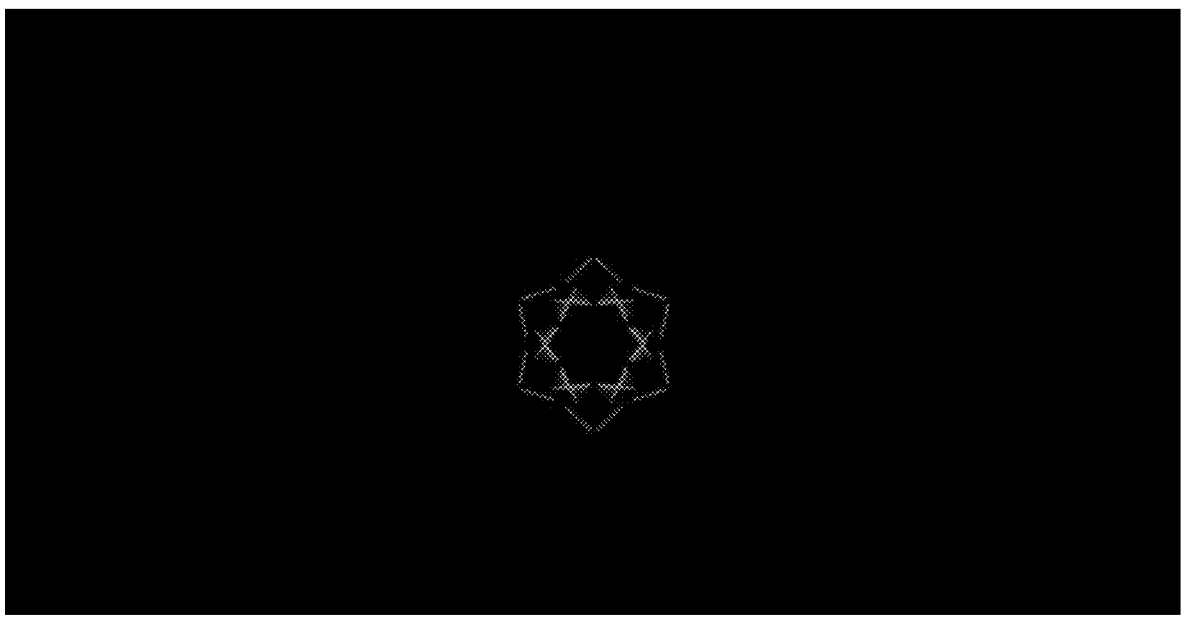
Figure 13C:
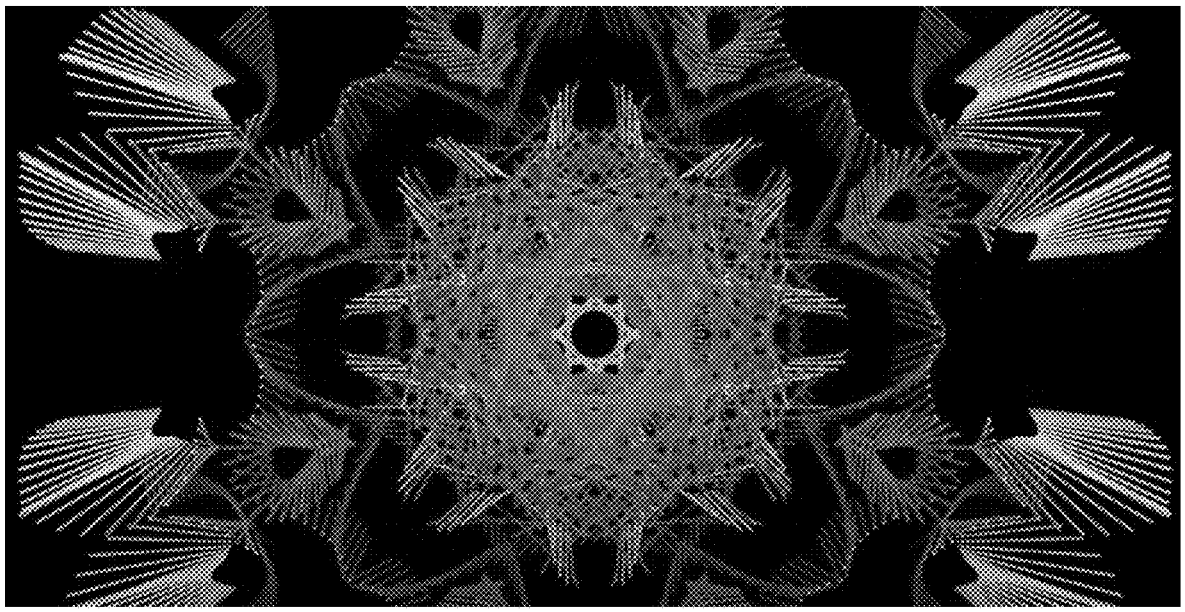
Figure 13D:
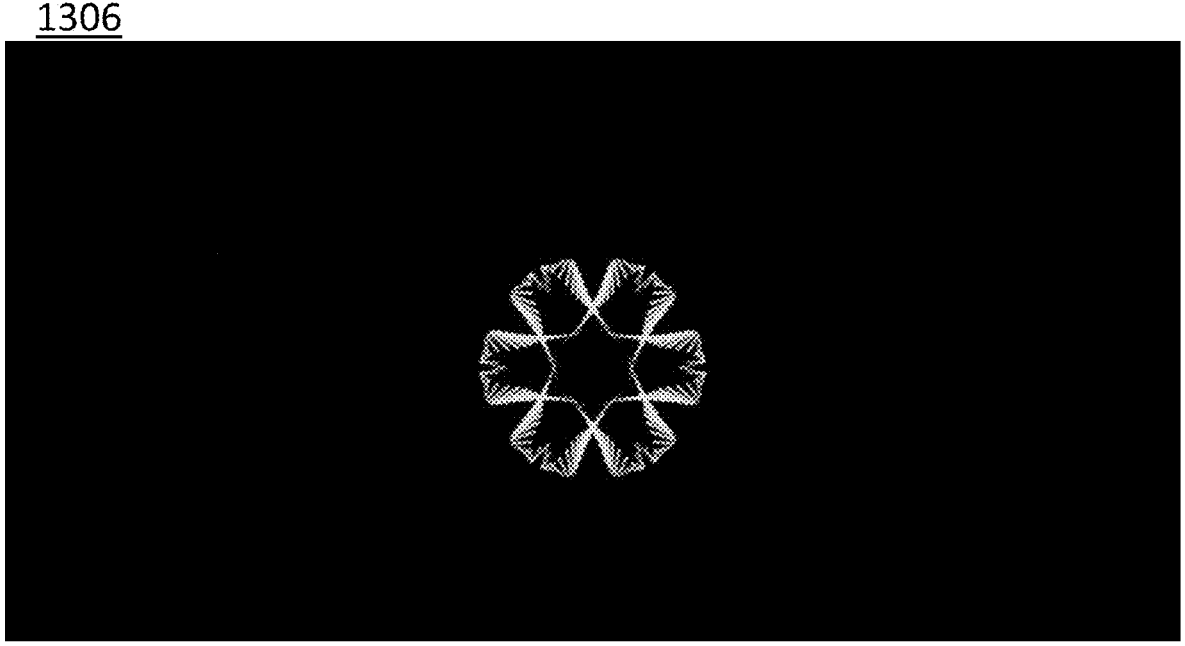
Figure 13E:
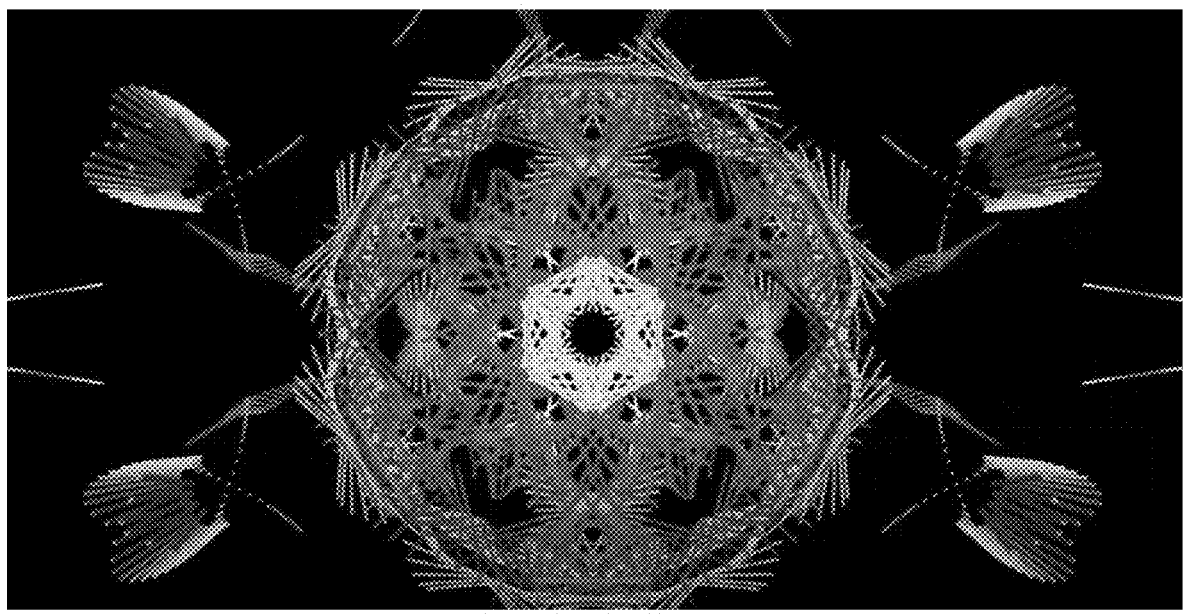

FIGS. 13A-13E depict another example scene that starts at 1300 and progresses through to 1302, 1304, 1306, and 1308 according to embodiments. The scene can start out in darkness, as depicted in FIG. 13A. The user can be instructed to focus or relax, e.g., to focus on his breathing, his body, or an object. One or more sensors (e.g., a BCI device, EEG device, PPG device, etc.) can be configured to collect user data after the user has been instructed to focus or relax (e.g., at 908 of the method 900). A score indicative of the state of the user (e.g., a measure of focus and/or relaxation) can then be generated using a model that processes the user data (e.g., at 912 of the method 900). When the user's score is above a certain threshold, geometric shapes (e.g., objects) can be generated starting near a center of the scene and expanding outwards, as depicted in FIGS. 13B and 13C. In the embodiment depicted, the geometric shapes can form mandala-like pattern, but it can be appreciated that other patterns and/or designs can be formed. In some embodiments, once a pattern has been fully formed and maintained for a preset amount of time (e.g., once the user's score has satisfied a predetermined metric by, for example, remaining above a threshold for a set period of time), then the user's continuing performance above the threshold can return to a dark scene and generate a new geometric shape, e.g., as depicted in FIG. 13D, and expand outward to form anew pattern, e.g., as depicted in FIG. 13E. When the user's score is below the threshold, then shapes do not form. When the user's score remains below the threshold for a preset amount of time, geometric shapes that have already formed and/or a geometric pattern that has formed can fade away, and the user must start again (e.g., with a new pattern forming, as depicted in FIGS. 13D and 13E, once their score is above the threshold again). In some embodiments, the scene can continue until a certain number of patterns have formed. Alternatively, the scene can continue until a predetermined period of time as elapsed (e.g., between about 5 minutes and about 20 minutes, including, for example, 10 minutes). In this latter instance, the scene may not have any checkpoints to complete. The gameplay can then end (e.g., at 930 of the method 900).

Figure 14A:
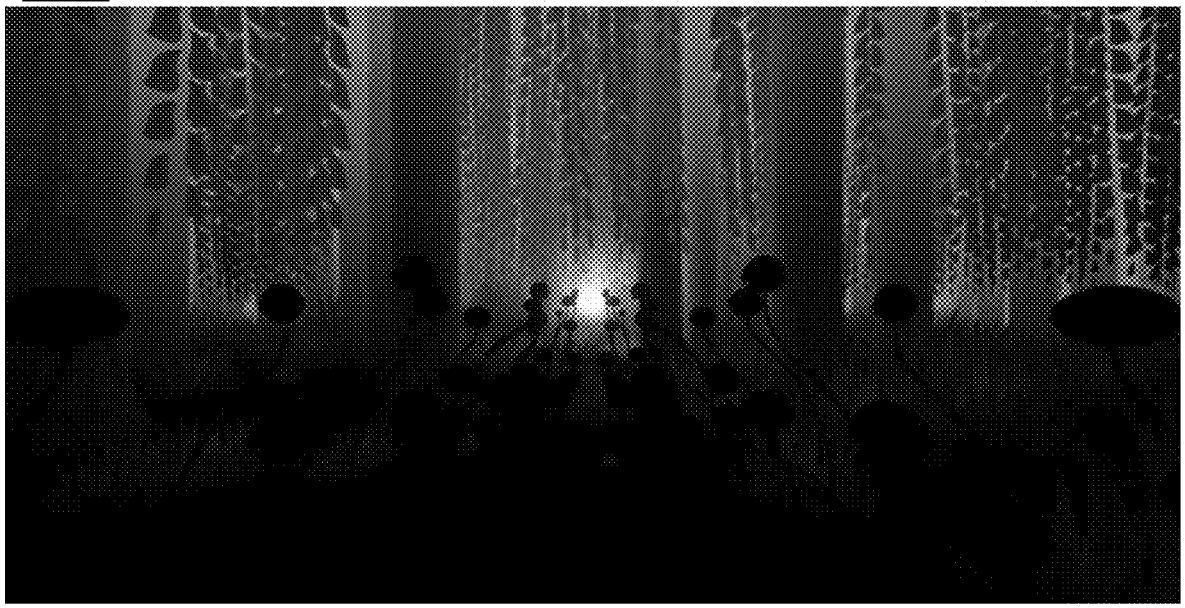
FIGS. 14A-14D depict different stages or points in another example scene used in a feedback-based meditation program, according to embodiments.
Figure 14B:
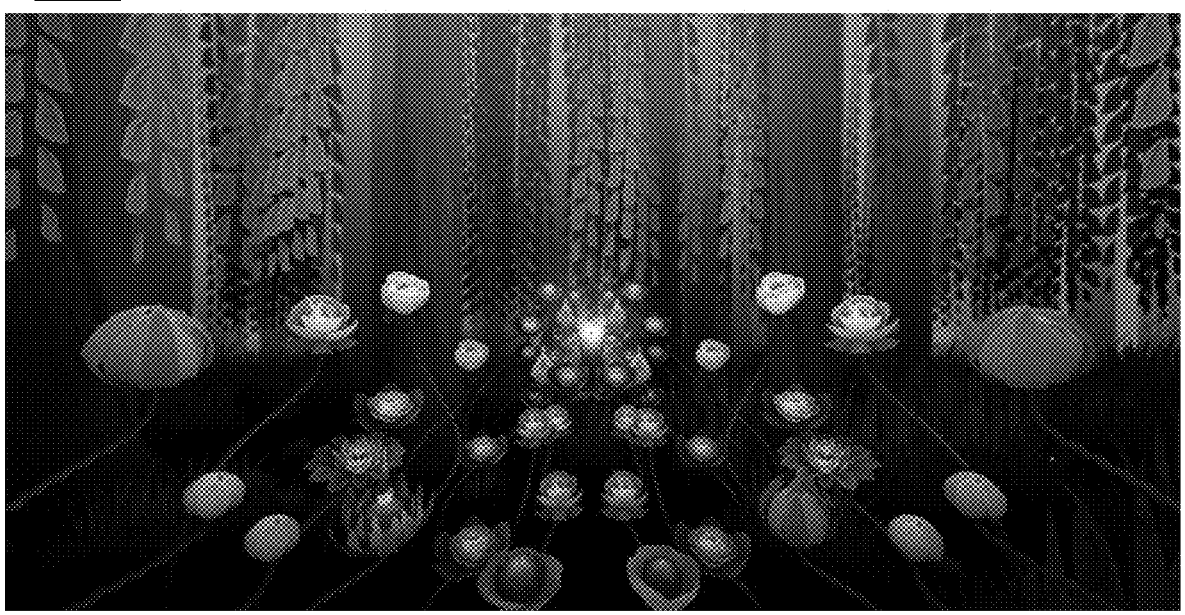
Figure 14C:
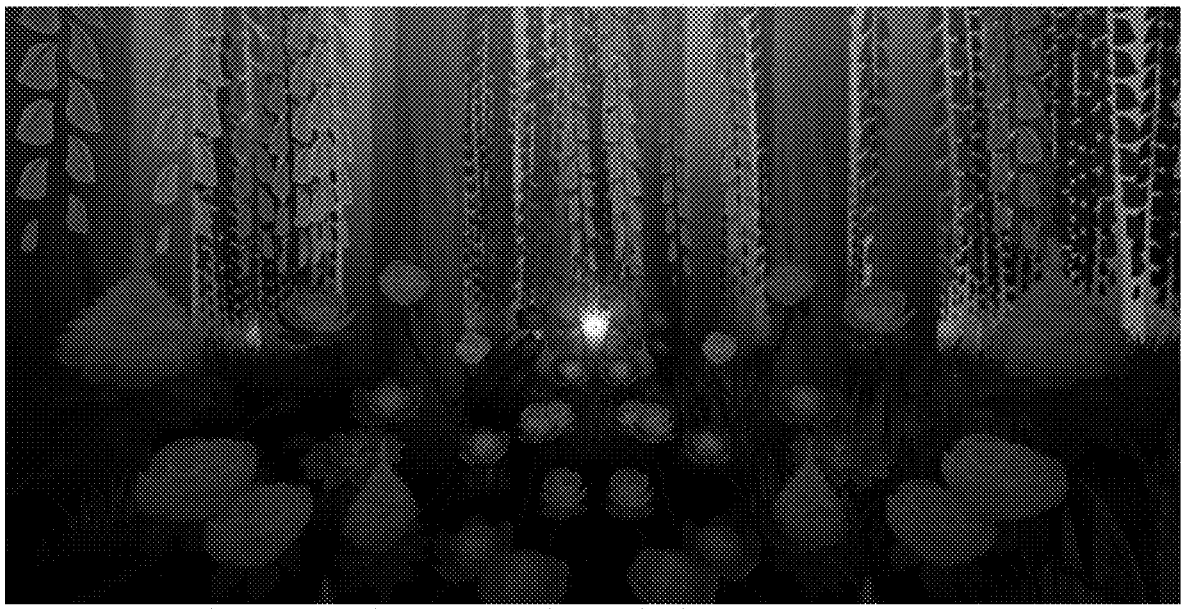
Figure 14D:
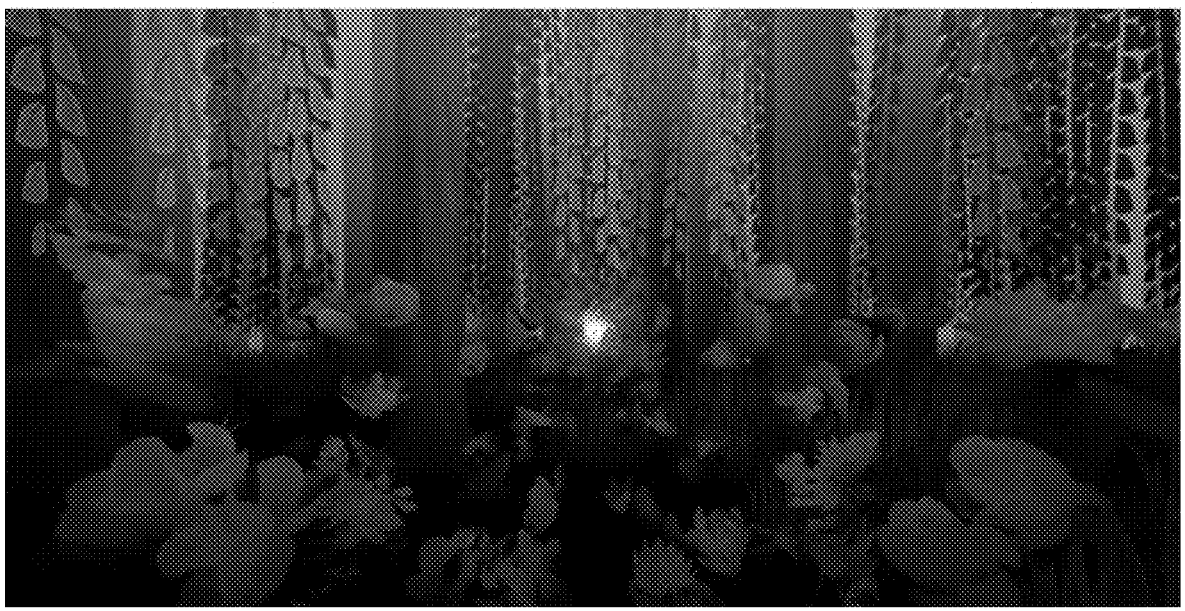

FIGS. 14A-14D depict yet another example of a scene, according to embodiments. FIGS. 14A-14D depict the scene as it starts at 1400 and then progress through to 1402, 1404, and 1406. The scene starts out in a dark forest setting, as depicted in FIG. 14A. The user can be instructed to focus or relax, e.g., to focus on his breathing, his body, or an object. One or more sensors (e.g., a BCI device, EEG device, PPG device, etc.) can be configured to collect user data after the user has been instructed to focus or relax (e.g., at 908 of the method 900). A score indicative of the state of the user (e.g., a measure of focus and/or relaxation) can then be generated using a model that processes the user data (e.g., at 912 of the method 900). When the user's score is above a certain threshold, then flowers (e.g., objects) in the scene can change, e.g., grow and bloom, as shown in FIG. 14B. When the user's score is below the threshold, then the flowers can turn a different color (e.g., purple), as shown in FIG. 14C. When the user's score remains below the threshold for a preset amount of time, the flowers can break into petals and gently float away, as depicted in FIG. 14D, and the user must start again (e.g., with a new set of flowers, once their score is above the threshold again). The scene can continue until a predetermined period of time as elapsed (e.g., between about 5 minutes and about 20 minutes, including, for example, 10 minutes). In this latter instance, the scene may not have any checkpoints to complete. The gameplay can then end (e.g., at 930 of the method 900).

In some embodiments, after a user has completed the feedback-based meditation or other multi-sensory exercise or gameplay, the user can have a set or state that is suitable for receiving a drug treatment. In some embodiments, a healthcare professional can then administer a drug treatment to the user. The drug treatment can be, for example, Psilocybin, Ketamine, Esketamine, R-Ketamine, RL-007 (e.g., for schizophrenia), Ibogaine, Deuterated Etifoxine, N-Acetylcysteine, methylenedioxy-methylamphetamine (MDMA), N-methyl-1-(3,4-methylenedioxyphenyl)propan-2-amine), methylenedioxy-methylamfetamine, 3,4-methyl-enedioxymethamphetamine, 3,4-Methylenedioxyamphetamine (MDA), Salvinorin A, Deuterated Mitragynine, Noribogaine, Dimethyltryptamine (DMT), N,N-DMT, D-Cycloserine, or other drug treatments with acute effects on a central nervous system. In some embodiments, a drug treatment can be administered to a user separate from a feedback-based meditation or other multi-sensory exercise, as described above.

In some embodiments, the healthcare professional can administer the drug treatment based on the user's scores, e.g., during the feedback-based meditation. For example, if the user's score indicates that the user has reached a higher state of relaxation and/or focus, then the healthcare professional may administer a high dose of a drug treatment. In some embodiments, depending on whether the user's scores are low or close to a threshold or significantly higher than a threshold (e.g., a certain percentage or amount above the threshold), then the healthcare professional may administer more or less of a drug. For example, if a user's score indicates that the user is less likely to be in a suitable state for receiving a drug treatment, then the healthcare professional may administer a lower dose the drug, e.g., to have a smaller effect on the user. Alternatively, if the user's score indicates that the user is more likely to be in a suitable state for receiving a drug treatment, then the healthcare professional may administer a higher dose of the drug. In some embodiments, the healthcare professional may also administer a smaller dose of a drug when a user is making reoccurring visits to a treatment site. In other words, if a user is periodically or repeatedly undergoing drug treatment, then smaller doses of the drug treatment may be delivered over time vs. a single larger dose.

Figure 10:
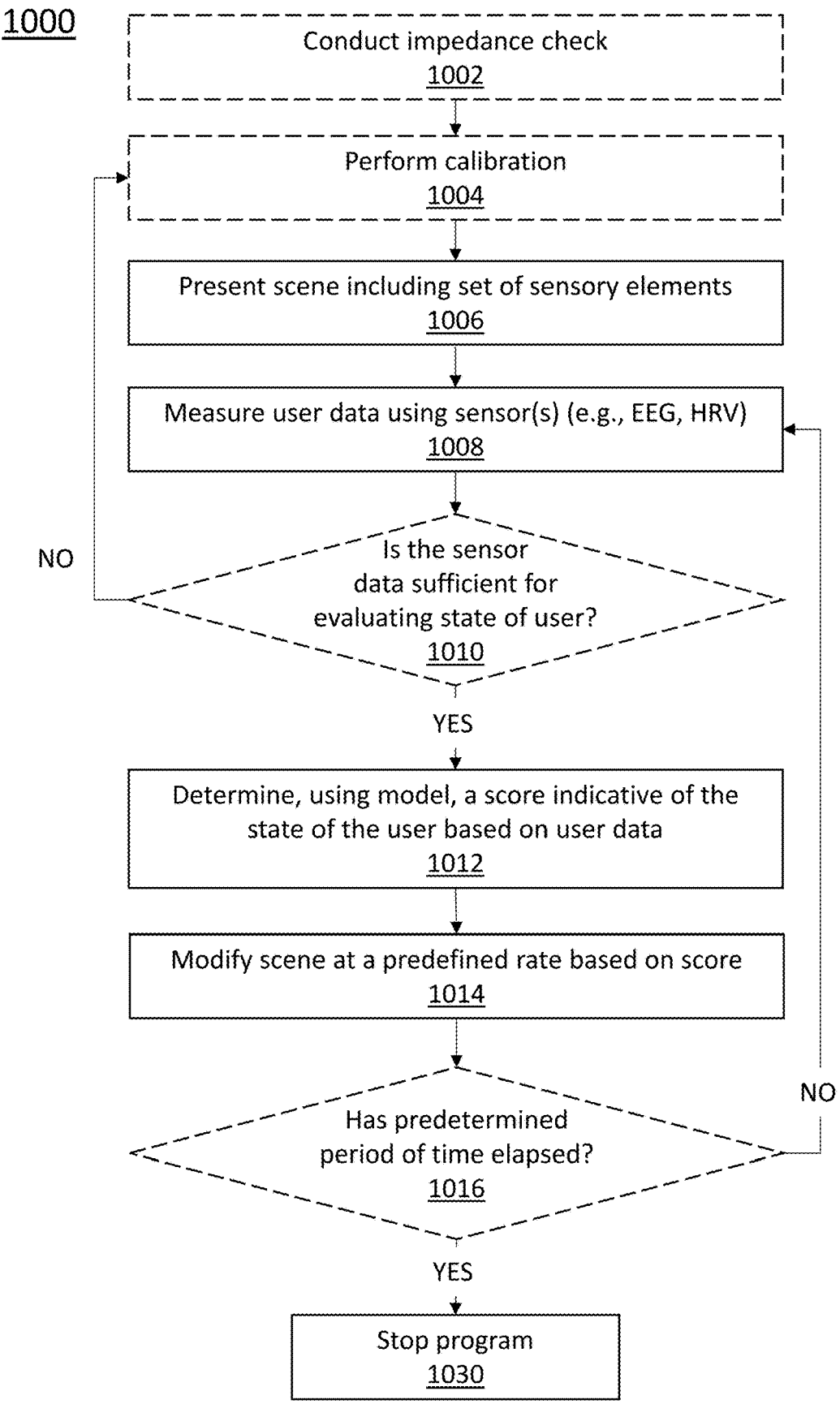
FIG. 10 depicts a method of implementing a feedback-based adaptive settings system, according to embodiments.

In some embodiments, a feedback-based adaptive settings program may be implemented, e.g., after a user has received a drug treatment and is experiencing acute condition associated with the drug treatment. FIG. 10 illustrates a method 1000 of performing a feedback-based adaptive settings process, according to an embodiment. The feedback-based adaptive settings process can be used to inform a therapy system (e.g., therapy system 100) of a user's state while that user is experiencing the effects of a drug treatment. An example of such a feedback-based adaptive settings process 1000, when used when a user is having a psychedelic experience, is described in more detail in the section "Example 1" below. In some embodiments, the method 400 can be performed by a therapy system that is structurally and/or functionally similar to the therapy system 100, as shown and described with respect to FIG. 1, and/or include elements that are similar to those described with respect to FIGS. 2 and 3.

In some embodiments, a user can wear a BCI device, an EEG device, and/or a PPG device, e.g., for measuring user data (e.g., EEG data, HRV data, etc.). The BCI device, EEG device, and/or PPG device can be an example of a sensor 120. At 1002, an impedance check can optionally be performed, e.g., to confirm that the BCI device or EEG device has been properly placed on the user. This can be similar to 902 of method 900, as described with respect to FIG. 9A, and therefore further details of this step are not provided herein again. Optionally, calibration data can also be collected, at 1004. This process can be similar to 904 of method 900, as described with reference to FIG. 9A. For example, calibration data can be collected and labeled via time locking with specific multi-sensory experiences (e.g., audio-video experiences). For example, a multi-sensory experience for use with calibration can be an audio-video experience that includes a series of calming and relaxing audio-visual environments (e.g., presented by headphones, displays, and/or projections), interspersed with periods of no environmental stimulation. This can provide a rough estimate of when the user is relaxed or not, and what the user's data (e.g., EEG data, HRV data, etc.) looked like when he was relaxed or not. The labeled data from the calibration phase can then be used to adapt a global classifier (e.g., global score model 303) to a personalized classifier (e.g., a personalized score model 304).

At 1006, a scene including a set of sensory elements (e.g., audio, visual, haptic, tactile, gustatory elements) can be presented, e.g., using a multi-sensory presentation device. The multi-sensory presentation device can be an example of a therapy device (e.g., therapy device 110). In some embodiments, the multi-sensory presentation device can include one or more projectors, tactile devices (e.g., a tactile vest), sound machines or other audio devices, scent generating devices, etc. In some embodiments, presenting the scene can involve projecting a scene of a tranquil environment (e.g., a beach, a forest, a room). For example, a scene of a tranquil forest, lit by moonlight, can be projected. In some embodiments, the scene can be projected on a specific surface or specific structures, e.g., one or more 3D structures (e.g., foam boxes) that can provide a feeling of depth and immersion to the scene. In some embodiments, a sound machine or headphones can play relaxing sounds, e.g., the sounds of crickets chirping, a stream of water calmly babbling, a sound of wind gently rustling the leaves of a tree, wave sounds, etc. In some embodiments, the sounds can be set into a binaural format that also provides various levels of depth and immersion to feel like the sounds are coming from particular locations in the space (e.g., the rustling of leaves on the trees nearby sound closer, and the babbling of the stream, which appears a distance away, sounds further away). In some embodiments, a tactile device such as a tactile vest can gently rumble across the user's back, e.g., massaging the user into relaxation. In some embodiments, a scent delivery device can delivery smells, e.g., of pine, damp moss, fresh air, ocean air, etc. In some embodiments, a temperature device can generate coolness or heat and/or moving air (e.g., via a fan).

At 1008, user data can be measured using one or more sensor(s). This can be similar to 908 of method 900, described above with respect to FIG. 9A. The user data can be sent from the sensor(s) to a compute device (e.g., compute device 130), and the compute device can process the user data. At 1010, the compute device can determine whether the sensor data is sufficient for evaluating a state of the user, e.g., as described above with respect to FIGS. 6-8.

If the data is not sufficient for evaluating the state of the user, then the process can return to 902. If the data is sufficient for evaluating the state of the user, then at 912, the compute device, e.g., implementing a score generator (e.g., score generator 143), can use a model to determine a score that is indicative of the state of the user based on the user data. In particular, the compute device can input the user data into the model, which can generate an output that is or is indicative of the score of the user. The model, as described with respect to FIG. 3 above, can be a classifier such as, for example, a global score model 303 or a personalized score model 304. The score can be based on or indicative of a measure of a user's relaxation or other state. While the scene 1100 is being presented, the compute device can repeatedly or periodically at intervals (e.g., between about 1 microsecond to about 10 seconds, including all subranges and values therebetween, including, for example, each 1 second), continue to collect user data, at 1008, and determine a score of the user, at 1012, e.g., to monitor the state of the user.

At 1014, the compute device can determine how to modify a scene based on the user's score. In some embodiments, after determining each score, the compute device can determine how the score compares to a threshold. When the user's score is far below a threshold (e.g., below a pre-defined range or deviation from the threshold), then the compute device can change the setting, e.g., abruptly and/or drastically. For example, the compute device can change a substantial majority or all of the elements in the scene (e.g., switching from a woods scene to a beach scene). Additionally, the compute device can change the scene immediately or close to immediately, e.g., within about 1 and about 10 seconds, including all values and sub-ranges therebetween. When the user's score is above or below the threshold by a small amount (e.g., within a certain range or deviation of the threshold), then the compute device can wait a predetermined period of time to see if the score increases, decreases, or remains the same. When the score remains the same or decreases, then the compute device can be configured to change the setting at a slower or less drastic rate. The compute device can also be configured to change less elements in the scene (e.g., switching from a darker woods setting to a lighter woods setting). For example, the nighttime forest that was initially projected can transition into daytime. The sound of the wind and the crickets chirping can subside, while the sound of the water can become clearer. The tactile vest sensation can decrease slightly. The scent delivery device can increase the release of pine scents. When the user's score remains well above the threshold (e.g., above a predefined range or deviation from the threshold), then the compute device can maintain the setting to be the same or substantially the same, e.g., with minor changes occurring as to ensure that the current setting does not become monotonous or superficial.

Once a predetermined period of time has elapsed, at 1016, then the program can stop, at 1030. In some embodiments, the predetermined period of time can be a predetermined period of time after receiving a drug treatment. In some embodiments, the program can continue until the user stops experiences effects from a drug treatment (e.g., until after a psychedelic experience is over). While the experience continues, the process can loop or return to 1008 to iteratively measure the user data, generate scores, and adapt the setting to the user based on his score.

Figure 5:
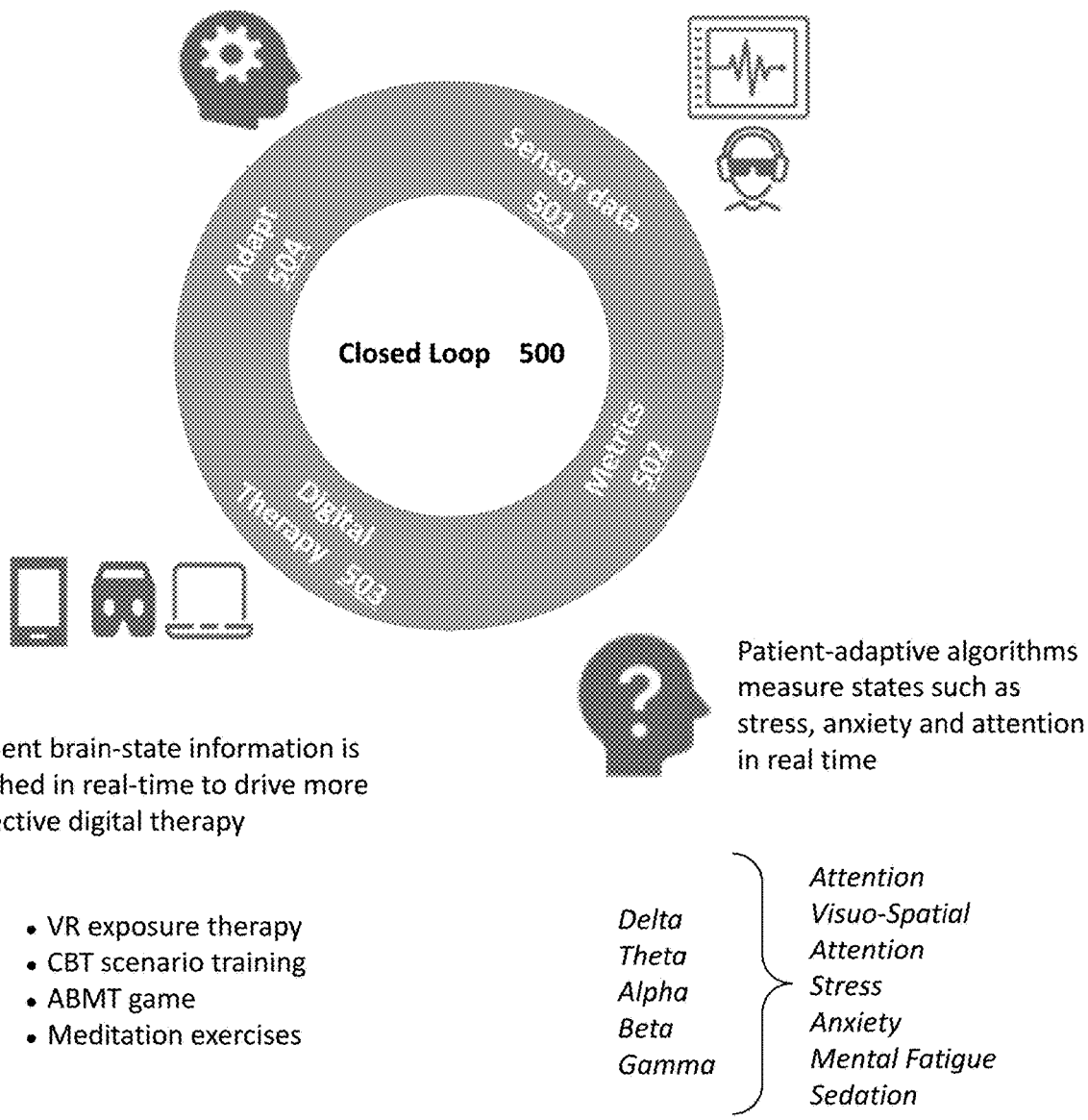
FIG. 5 is a schematic diagram illustrating a closed-loop for a digital therapy, according to an embodiment.

FIG. 5 is a schematic diagram illustrating a closed-loop 500 for a digital therapy (or other multi-sensory experience or exercise), according to an embodiment. The closed-loop 500 can be performed by the therapy system 100 as shown and described with respect to FIG. 1. The closed-loop 500 can involve collecting sensor data 501 (e.g., EEG signals) from a user undergoing a digital therapy. In some instances, the digital therapy can induce a behavioral response in the patient. At that time, a brain-computer interface (BCI) device (e.g., the therapy device 110 as shown and described with respect to FIG. 1) can simultaneously capture neural activity in the brain.

The closed-loop 500 can involve measuring changes in the mental state(s) of the user during the digital therapy using a set of metrics 502. For example, in some instances, a score generator (similar to score generator 143 shown and described with respect to FIG. 1) can include, but is not limited to, patient-adaptive methods that measure states such as stress, anxiety, and attention in substantially real time (10 milliseconds, 100 milliseconds, 1 second, 2 seconds, 10 seconds, or, 20 seconds) extract features from the sensor data that are indicative of attention, visuo-spatial attention, stress, anxiety, mental fatigue, and/or sedation.

The closed-loop 500 can involve operating the digital therapy 503 by using the user's sensor data (e.g., brain-state information) in substantially real-time (e.g., 10 milliseconds, 100 milliseconds, 1 second, 2 seconds, 10 seconds, or 20 seconds) to adjust the digital therapy 503 such that the digital therapy 503 is more effective for the user. The digital therapy 503 can involve, but is not limited to, for example, a virtual reality (VR) exposure therapy, cognitive behavioral therapy (CBT) scenario therapy, an attention-bias modification training (ABMT) game, adaptive settings, and/or meditation exercises.

The closed-loop 500 can further involve adapting 504 the digital therapy 503. Similarly stated, the closed-loop 500 can adaptively change the digital therapy (e.g., adaptively changing a difficulty level of the digital therapy, adaptively progressing a visual within the same difficulty level of the digital therapy, and/or or adaptively changing the system of selection/generation of a setting) in response to a patient's progress. In some instances, the patient's progress can be a measure of mental state response to a digital setting. In some implementations, a machine learning model (e.g., similar to the score generator 143 as shown and described with respect to FIG. 1) can be used to generate a score to estimate a progression (e.g., a completeness) of the digital therapy 503. Thereafter, the closed-loop 500 can adaptively change the digital therapy based on the estimated score.

Example 1—Feedback-Based Multi-Sensory Programs

In some instances, the multi-sensory experience or exercise such as a digital therapy can involve performing a game and/or a congestive task by the user. For example, in some instances, the digital therapy can involve performing an Eriksen flanker task. Because the user of the therapy systems described above with respect to FIGS. 1-5 often has limited movement (e.g., sitting in one position) while conducting the digital therapy, in some instances, the game and/or the congestive task experience can show, for example, a first-person perspective that is from a fixed position. Otherwise, negative senses such as nausea may arise.

In some instances, the game and/or the congestive task can involve generating vibrations through meditation. For example, a therapy device (e.g., therapy device 110) or compute device (e.g., compute device 130) can include one or more output devices, including a vibration generating device (e.g., transducer). The compute device can be configured to determine, e.g., via a score generator (e.g., score generator 143), a score indicative of a meditation state of the user. The compute device and/or therapy device can then generate vibrations based on this score of the user. As stronger vibrations are generated by the user reaching higher meditative states within the game and/or the congestive task, particles (e.g., that are randomly scattered and/or distributed) that occupy various points in the virtual space in the game and/or the congestive task, can come together and form, for example, a three-dimensional (3D) and/or symmetric geometric pattern. In addition, in some instances, the user can be also provided with a binaural sound on which the user can focus. The binaural frequencies can assist inducing particular patterns of brain activity through the mechanism of neural entrainment.

In an example embodiment, a user can visit a clinic for pre-treatment session (e.g., before using a drug treatment). The user can be sat in a comfortable position (e.g., in a chair or on the floor) and in a quiet setting. In the clinic, a clinician (e.g., a nurse, a physician, a specialist, and/or other medically-trained professional) can place a brain-computer interface (BCI) device (e.g., a 2-4 electrode BCI device) and a virtual reality (VR) device on the user's head. The BCI device can include sensors (e.g., sensors 120) implemented as electrodes. The clinician can begin a digital therapy, using the VR device that is operatively coupled to a compute device (e.g., similar to the compute device 130 as shown and described with respect to FIG. 1). The user can be handed a controller(s) that is operatively coupled or connected to the VR device. Upon an indication(s) from the user and/or the clinician, the digital therapy can begin, for example, via an interactive application (e.g., presenter 147) executed by the VR device and/or the compute device.

During the digital therapy, a set of instructions can be displayed at the interactive application. Next, during a calibration phase, a pre-game calibration task can begin, which can enable a brain-computer interface (BCI) process and the VR device to be calibrated or set to the user's brain activities. In some instances, the calibration phase can also be used to collect labeled user data used to train a user-specific machine learning model(s) (e.g., use combined data from the calibration phase with a global machine learning model(s) to develop the user-specific machine learning model(s)). In the calibration phase, an audio-guided induction phase can be presented to put the user into a relaxed state. The user is then introduced to a feedback metaphor that user can learn to control by modulating his/her level of attention and/or other mental states. In one example, the metaphor can involve playing a more chaotic visual(s) and a higher volume noise(s) in response to incorrect behavior, and a more orderly visual(s) and lower volume noise in response to correct behavior. In another example, the metaphor can involve playing a high tone audio in response to a correct behavior and a low tone audio in response to an incorrect behavior. The calibration phase can continue and be repeated before beginning a gameplay. In some instances, the clinician can stand by for a signal from the interactive application indicating that the user is in an appropriate mental state for the gameplay (e.g., based on the user attaining a sustained score, e.g., as calculated based on score generator 143, that meets a predetermined threshold). In response to determining that the user has an appropriate mental state, the calibration phase can be ended, and optionally the clinician can remove the VR device and/or the BCI device. In some instances, completion of the gameplay can indicate that the user is ready for a dosing for the drug treatment.

In some instances, the interactive application can include a therapist mode, in which the therapist can take control of an exercise and modify the exercise to guide the user in a predefined manner. In some instances, the digital therapy system can receive feedback from the user (e.g., by providing a questionnaire after the session or by estimating the user's gameplay performance) to determine whether the user has certain preferences, e.g., a gameplay with binaural sounds or a quiet gameplay.

As the user focuses on the sound, the user score (e.g., generated by the score generator 143 shown and described with respect to FIG. 1) can be measured in real-time and reflected back to the user through visual and auditory feedback. Auditory feedback can be reflected in a volume of the binaural sound, where higher scores can be associated to reducing volume and lower scores can be associated to increasing volume. Visually, this can be shown by a level of "harmony" in the particles in a scene, where higher scores are linked to particles gently vibrating and moving towards pattern-based formations and lower scores are linked to particles not vibrating and moving towards random and messy positioning. In some instances, the user score can be also used for visual and auditory feedforward. In other words, the user's mental state score can be used to control the gameplay and the user can be incentivized to move the game forward/progress via the visual and auditory control mechanisms.

In some embodiments, a user's EEG and HRV bio-signals can be used to inform a therapy system (e.g., similar to the therapy system 100 as shown and described with respect to FIG. 1) of a user's mental state in regard to optimal set (e.g., a suitable state) for a psychedelic experience that is both positive and promotes long-term well-being scores. An optimal set, for this example, can be a state of relaxation, low anxiety, low emotional excitability, positive affect, mental clarity, openness to the experience (e.g., surrendering), and focused attention.

The therapy system can use the EEG and HRV to generate a score for the user's state and accordingly determine whether the score meets a minimum pre-set threshold (a personalized threshold determined, for example, by a specialist). The therapy system can include a therapy device 110 that can include a 3D-projection mapping system, a tactile vest, a binaural audio system, and/or a scent delivery system that can effectively be used to control visual, haptic, auditory and olfactory aspects of a setting, respectively. Each of the 3D-projection mapping system, the tactile vest, the binaural audio system, and/or the scent delivery system can have a library of settings/states. The settings/states can be generated in real-time. The library of settings/states can be determined/developed based on, for example, a broad consensus of what is relaxing, positive, and focus-inducing.

In one example, a user can wear a brain-computer interface (BCI) device with a built-in PPG sensor that measures heart-rate variability. The user can wear a tactile vest with mechanical vibrators sewn into the vest and powered by electrical motors. The user can wear comfortable headphones capable of playing binaural audio. The user can be in a room with 4 integrated projectors, each pointed at 1 of the 4 walls in the room. The room can also include various foam boxes placed strategically around the room that the projectors can project onto in addition to the walls of the room. In addition, the room can also include a scent delivery device positioned inconspicuously near the center of the room.

Next, an impedance check can be performed to ensure that the BCI signal output is sufficiently accurate. The real-time impedance check can appear as a diagram projected on the wall and a BCI device with 4 glowing light emitting diodes (LEDs), each representing an electrode. If the node glows green, then the electrode is making appropriate contact with the skin. If the node glows red, then the user needs to readjust the device. Once all 4 LEDs are green, the next phase begins.

Next, upon dosing with a drug treatment and after passing the impedance check, calibration data can be collected and labeled via time locking with specific audio-visual experiences. Audio-visual experiences used for labeling data can include a series of calming and relaxing audio-visual environments presented by the projectors and headphones, interspersed with periods of no environmental stimulation. This can provide a rough estimate of when an individual was relaxed or not and what the individual's EEG/HRV signals looked like when he/she was relaxed or not relaxed. The labeled data from the calibration phase can then be used in conjunction with an existing machine learning model (e.g., a global in-treatment classifier) to develop a subject-specific machine learning model (e.g., a subject-specific in-treatment classifier) that is more accurate to the user's unique brain signals.

Next, 3D projectors can be used to project a scenery of a tranquil forest, lit by the moonlight. The scenery can include trees. Some of the trees in the scene can be projected onto the foam boxes, giving a feeling of depth and immersion to the scene that otherwise would feel flat. Headphones can play the sounds of crickets chirping, a stream of water calmly babbling, and the wind gently rustling the leaves of the trees. The sounds can be set into a binaural format that also provides various levels of depth and immersion to feel like the sounds are coming from particular locations in the space (e.g. the rustling of leaves on the trees nearby sound closer, and the babbling of the stream, which appears in the distance sounds further away). The tactile vest can gently rumble across the participant's back, almost massaging the person into relaxation. In addition, a scent delivery device can deliver smells of pine, damp moss, and/or fresh air.

Next, sensor data can be collected from the user as described above and a score generator (similar to the score generator 143 as shown and described with respect to FIG.

1) can generate an in-treatment score for the user's state. Based on the user's current in-treatment score, if a user's score is far below a threshold, then the setting can change drastically. For example, a scene of a beach on a warm, sunny day appears through the projectors. The headphones can play the sound of gently crashing waves. The tactile vest can decrease stimulation or changes the location of vibration. The scent delivery device can deliver the smells of salt water and coastal air.

If a user's score is above or below the threshold by a bit, the system can wait a pre-set amount of time and if the score has not improved or is wavering, then the setting can change but less drastically. For example, the night-time forest that was initially projected can transition into daytime. The sound of the wind and the crickets chirping can subside, while the sound of the water can become clearer. The tactile vest sensation can decrease slightly. The scent delivery device can increase the release of pine scents. If a user's score remains well above the threshold then the setting can remain mostly the same with minor changes occurring as to ensure that the current setting does not become monotonous or superficial. The therapy exercise can continue to repeat with a large library of potential settings until the psychedelic experience is over. During the above process, data can be collected on the user's setting preference based on whether the in-treatment score goes up or down in response to a specific setting. The data can then be used to refine a list of appropriate settings that can be used for a particular individual.

In one example, a user can visit a clinic for a psychedelic treatment. The clinic can be fitted with projectors assigned to each wall, foam boxes to enable 3D-projection mapping (i.e., projecting onto multiple surfaces to give a feeling of depth and immersion), and a scent delivery device near the center of the room. The user can sit in a comfortable position on a couch. The user can put on a tactile vest. In the clinic a nurse (or other medically-trained professional) can place a BCI/PPG device on the patient's head along with a pair of headphones. In some instances, the nurse can initiate a real-time impedance check protocol via a computer (e.g., similar to the compute device 130 as shown and described with respect to FIG. 1) in the room. In some instances, the nurse can initiate an impedance check prior to starting a digital therapy session. The impedance check can run automatically throughout the digital therapy session to ensure the signal remains stable during the digital therapy session. Upon completion of the real-time impedance check, the computer can notify the nurse to begin dosing. A calibration experience can begin, which can enable a setting of a therapy device to be optimized to the user's brain activity. Upon completion of the calibration experience, a psychedelic treatment can begin. Upon completion of the psychedelic treatment, the nurse can remove devices from the user.

Example 2—Feedback-Based Meditation Study

In an example study involving healthy individuals, a feedback-based meditation exercise or program was implemented, e.g., according to methods described herein, such as, for example, method 900 described with reference to FIGS. 9A and 9B. The study involved the following:

A pre-session breath counting test and questionnaire
System setup
VR meditation exercise (e.g., a VR-implemented game)
A post-session breath counting test and questionnaire
During the pre-session breath counting test and questionnaire, each user was asked to indicate their level of relaxation and calmness, and then asked to perform a breath counting exercise (e.g., count a certain number of breaths). Specifically during the study, each user was asked to count 9 breaths.

During the system setup, a BCI device including one or more EEG sensors (e.g., sensor(s) 120) is connected to a meditation application (e.g., implemented by a therapy device 110 and/or compute device 130). In the study, a Muse brain sensing headset was used. Each user was instructed to wear the BCI device according to specific protocols, e.g., ensuring headset is securely in place but is comfortable, conducting an impedance check, etc. A VR device can then be connected to the meditation application (e.g., implemented by a therapy device and/or compute device 130). The VR device can then be set up according to standard procedures, e.g., setting of room boundaries, setting of sit and stand positions, etc.). Each user was instructed to then wear the VR device. In particular, each user was instructed to wear the VR device over the BCI device.

During the VR meditation exercise, a scene the same as or substantially the same as the scene 1100 depicted in FIGS. 11A-11E was presented to each user. In particular, each user was asked to form the six rings depicted in FIG. 11E. During the VR meditation exercise, a therapist (e.g., via a therapist application running on the compute device) had control to stop the VR meditation exercise at any time.

After each user completed the VR meditation game, the user performed a post-session breath counting test and questionnaire, similar to the pre-session breath counting test and questionnaire. In particular, the user was again asked to provide their feedback on relaxation and calmness. The user was also asked to provide feedback on the session (e.g., how did you find the overall experiences, did you have any problems with the experience, etc.). The user then performed a breath counting test, e.g., counting breaths to 9.

Data was successfully captured from users in 35 sessions in the study. From the data collected during these sessions from these users, the following was observed:

(74.3%) 26 out of 35 sessions showed improvement in calmness. 17.1% showed no change as those users were already "Very Calm" prior to their VR session. 5.7% (2 sessions) showed decrease in calmness after the VR meditation session (91.4%) 32 out of 35 sessions showed improvement in relaxation. 2.8% showed no change. 5.7% (2 sessions) showed decrease in relaxation after the VR meditation session In 25 out of total 35 sessions (71% of sessions), users were either Very Much Calm or Extremely Calm after the VR meditation session In 21 out of total 35 sessions (60% of sessions), users were either Very Much Relaxed or Extremely Relaxed after the VR meditation session As evidenced by the observations above, the VR meditation exercise was useful in increasing calmness and relaxation in users.

Systems, devices, and methods described herein can be implemented as one or more of the example embodiments below:

Embodiment 1: An apparatus, comprising: a virtual reality (VR) device configured to present at least one of a visual, olfactory, gustatory, auditory, or haptic signal to a user; a set of sensors configured to measure user data, the set of sensors including at least an electroencephalography (EEG) sensor and a photoplethysmography (PPG) sensor; a memory; and a processor operatively coupled to the virtual reality device, the set of sensors, and the memory, the processor configured to: present, using the VR device, a scene including a first set of objects to the user, the first set of objects including visual, olfactory, gustatory, auditory, or haptic elements; instruct a user to engage in an activity for increasing focus or relaxation; after the user has been instructed to engage in the activity, iteratively perform until a score indicative of a state of the user satisfies a metric: measuring, using the set of sensors, the user data including at least EEG data and heart rate variability (HRV) data; determining, using a model trained to measure the state of the user, and based on the user data, the score of the user; and in response to the score of the user being above a threshold, modifying, using the VR device, the presentation of the first set of objects such that the first set of objects form or follow a pattern or presenting, using the VR device, an additional object; and in response to the score of the user satisfying the metric, present, using the VR device, a second set of objects to the user.

Embodiment 2: The apparatus of Embodiment 1, wherein the additional object is an auditory element including a tone, a sound effect, or music.

Embodiment 3: The apparatus of any one of Embodiments 1-2, wherein the processor is configured to instruct the user to engage in the activity for increasing focus or relaxation by: instructing the user to focus on breathing; instructing the user to focus on a visual element or an auditory element; instructing the user to focus on a body of the user; or performing a combination thereof.

Embodiment 4: The apparatus of any one of Embodiments 1-3, wherein the user data further includes at least one of: heart rate data, respiratory data, PPG data, galvanic skin response data, blood glucose data, pupillometry data, eye movement data, electromyography (EMG) data, electrodermal activity (EDA) data, blood pressure data, or body temperature.

Embodiment 5: The apparatus of any one of Embodiment 1-4, wherein the score of the user satisfies the metric when the score of the user remains above the threshold for a set period of time.

Embodiment 6: The apparatus of any one of Embodiments 1-5, wherein the first set of objects includes a first set of visual elements, the processor configured to modify the presentation of the first set of objects by moving one or more visual elements of the first set of visual elements to form a pattern with the first set of visual elements.

Embodiment 7: The apparatus of any one of Embodiments 1-6, wherein the first set of objects includes a first set of audio elements, the processor configured to modify the presentation of the first set of audio elements by reducing an intensity or frequency of one or more audio element of the first set of audio elements.

Embodiment 8: The apparatus of any one of Embodiments 1-7, wherein the processor is configured to present the second set of objects while the first set of objects continue being presented.

Embodiment 9: The apparatus of any one of Embodiments 1-7, wherein the processor is further configured to fade away the first set of objects before presenting the second set of objects.

Embodiment 10: The apparatus of any one of Embodiments 1-9, wherein the processor is configured to present, using the VR device, a plurality of sets of objects to the user, the plurality of sets of objects including the first and second sets of objects, the processor configured to present each subsequent set of objects of the plurality of sets of objects in response to the state of the user satisfying the metric after the set of objects immediately prior to the subsequent set of objects is presented.

Embodiment 11: The apparatus of Embodiment 10, wherein the state of the user satisfies the metric when the score of the user remains above the threshold for a set period of time.

Embodiment 12: The apparatus of Embodiment 11, wherein the processor is further configured to adjust, based on the user data collected during an initial period of time, the threshold to change a difficulty of satisfying the metric.

Embodiment 13: The apparatus of Embodiment 12, wherein the processor is configured to adjust the threshold by: determining, based on the user data collected during the initial period of time, a competency group for the user, the competency group being from a set of competency groups; and setting the threshold based on the competency group determined for the user.

Embodiment 14: The apparatus of Embodiment 12, wherein the processor configured to adjust the threshold by: determining, based on the user data collected during the initial period of time, a rate of progression through the plurality of sets of objects; setting the threshold based on the rate of progression.

Embodiment 15: The apparatus of Embodiment 14, wherein the processor is configured to set the threshold based on the rate of progression by: increasing the threshold when the rate of progression is greater than predetermined rate; and decreasing the threshold when the rate of progression is less than the predetermined rate.

Embodiment 16: The apparatus of Embodiment 10, wherein the processor is further configured to, in response to the state of the user satisfying the metric after the last set of objects of the plurality of sets of objects is presented, send an instructions to administer a drug treatment to the user.

Embodiment 17: The apparatus of any one of Embodiments 1-16, wherein the model is a user-specific model, the processor being further configured to, prior to presenting the scene including the first set of objects: present, during a calibration phase, a set of calming environment stimulations to the user interspersed with periods of no environmental stimulation; measure user data during the calibration phase; and adapt, using the user data measured during the calibration phase, a generic model trained to measure a state of a user to be the user-specific model.

Embodiment 18: The apparatus of any one of Embodiments 1-17, wherein the processor is further configured to, prior to presenting the scene: determine whether an impedance measured by the EEG sensor falls within a predetermined range of impedances; in response to the impedance being within the predetermined range, present an indication that the EEG sensor is properly positioned; in response to the impedance not being within the predetermined range, present an indication that the EEG sensor needs to be readjusted.

Embodiment 19: The apparatus of any one of Embodiments 1-18, wherein in response to the score of the user being below the threshold, modifying, using the VR device, the presentation of the first set of objects such that the first set of objects regress to an earlier state.

Embodiment 20: An apparatus, comprising: a virtual reality (VR) device configured to present at least one of a visual, olfactory, gustatory, auditory, or haptic signal to a user; one or more electroencephalography (EEG) sensors configured to measure EEG data of the user; a memory; and a processor operatively coupled to the virtual reality device, the one or more EEG sensors, and the memory, the processor configured to: present, using the VR device, a scene including a first set of objects to the user, the first set of objects including visual, olfactory, gustatory, auditory, or haptic elements; instruct a user to engage in an activity for increasing focus or relaxation; after the user has been instructed to engage in the activity, iteratively perform until a score indicative of a state of the user satisfies a metric: measuring, using the one or more EEG sensors, the EEG data; determining, using a model trained to measure the state of the user, and based on the EEG data, the score of the user; and in response to the score of the user being above a threshold, modifying, using the VR device, the presentation of the first set of objects such that the first set of objects form or follow a pattern or presenting, using the VR device, an additional object; and in response to the score of the user satisfying the metric, present, using the VR device, a second set of objects to the user.

Embodiment 21: The apparatus of Embodiment 20, wherein the additional object is an auditory element including a tone, a sound effect, or music.

Embodiment 22: The apparatus of any one of Embodiments 20-21, wherein the processor is configured to instruct the user to engage in the activity for increasing focus or relaxation by: instructing the user to focus on breathing; instructing the user to focus on a visual element or an auditory element; instructing the user to focus on a body of the user; or performing a combination thereof.

Embodiment 23: The apparatus of any one of Embodiments 20-22, wherein the score of the user satisfies the metric when the score of the user remains above the threshold for a set period of time.

Embodiment 24: The apparatus of any one of Embodiments 20-23, wherein the first set of objects includes a first set of visual elements, the processor configured to modify the presentation of the first set of objects by moving one or more visual elements of the first set of visual elements to form a pattern with the first set of visual elements.

Embodiment 25: The apparatus of any one of Embodiments 20-24, wherein the first set of objects includes a first set of audio elements, the processor configured to modify the presentation of the first set of audio elements by reducing an intensity or frequency of one or more audio element of the first set of audio elements.

Embodiment 26: The apparatus of any one of Embodiments 20-25, wherein the processor is configured to present, using the VR device, a plurality of sets of objects to the user, the plurality of sets of objects including the first and second sets of objects, the processor configured to present each subsequent set of objects of the plurality of sets of objects in response to the state of the user satisfying the metric after the set of objects immediately prior to the subsequent set of objects is presented.

Embodiment 27: The apparatus of Embodiment 26, wherein the state of the user satisfies the metric when the score of the user remains above the threshold for a set period of time.

Embodiment 28: The apparatus of Embodiment 27, wherein the processor is further configured to adjust, based on the user data collected during an initial period of time, the threshold to change a difficulty of satisfying the metric.

Embodiment 29: The apparatus of Embodiment 27, wherein the processor is further configured to, in response to the state of the user satisfying the metric after the last set of objects of the plurality of sets of objects is presented, send an instructions to administer a drug treatment to the user.

Embodiment 30: The apparatus of any one of Embodiments 20-29, wherein the processor is further configured to, prior to presenting the scene: determine whether an impedance measured by each of the one or more EEG sensors falls within a predetermined range of impedances; in response to the impedance measured by an EEG sensor of the one or more EEG sensors being within the predetermined range, present an indication that that EEG sensor is properly positioned; in response to the impedance measured by an EEG sensor of the one or more EEG sensors not being within the predetermined range, present an indication that that EEG sensor needs to be readjusted.

Embodiment 31: A method, comprising: presenting, using a virtual reality (VR) device, a scene including a first set of objects to the user, the first set of objects including visual, olfactory, gustatory, auditory, or haptic elements; instructing a user to engage in an activity for increasing focus or relaxation; after the user has been instructed to engage in the activity, iteratively performing until a score indicative of a state of the user satisfies a metric: measuring, using a set of sensors including an electroencephalography (EEG) sensor and a photoplethysmography (PPG) sensor, the user data including at least EEG data and heart rate variability (HRV) data; determining, using a model trained to measure the state of the user, and based on the user data, the score of the user; and in response to the score of the user being above a threshold, modifying, using the VR device, the presentation of the first set of objects such that the first set of objects form or follow a pattern or presenting, using the VR device, an additional object; and in response to the score of the user satisfying the metric, presenting, using the VR device, a second set of objects to the user.

Embodiment 32: An apparatus, comprising: a multi-sensory presentation device configured to present at least one of a visual, olfactory, gustatory, auditory, or haptic signal to a user; a set of sensors configured to measure user data, the set of sensors including at least an electroencephalography (EEG) sensor and a photoplethysmography (PPG) sensor; a memory; a processor operatively coupled to the memory, the multi-sensory presentation device, and the set of sensors, the processor configured to: present, using the multi-sensory presentation device and after the user has received a drug treatment, a scene to the user, the scene including a first set of visual, olfactory, gustatory, auditory, or haptic elements; while the scene is being presented, iteratively perform: measuring, using the set of sensors, user data including at least EEG data and heart rate variability (HRV) data; determining, using a model trained to measure a state of the user, and based on the user data, a score of the user indicative of a state of the user; in response to the score being lower than a threshold, modifying, based on the score of the user, the scene to include a second set of visual, olfactory, gustatory, auditory, or haptic elements different from the first set of visual, olfactory, gustatory, auditory, or haptic elements; and in response to the score being greater than the threshold for a set period of time, modifying the scene to include a third set of visual, olfactory, gustatory, auditory, or haptic elements different from the first and second sets of visual, olfactory, gustatory, auditory, or haptic elements; and continue to present the scene to the user until a predetermined period of time has elapsed from the user receiving the drug treatment.

Embodiment 33: The apparatus of Embodiment 32, wherein the multi-sensory device is configured to present at least two of visual, olfactory, gustatory, auditory, or haptic signals.

Embodiment 34: The apparatus of any one of Embodiments 32-33, wherein the multi-sensory device includes a virtual reality (VR) device, a projector, smart glasses, or a parallax screen configured to generate a visual environment.

Embodiment 35: The apparatus of Embodiment 34, wherein modifying the scene to include the second set of visual, olfactory, gustatory, auditory, or haptic elements includes changing from a first visual environment to a second visual environment, and modifying the scene to include the third set of visual, olfactory, gustatory, auditory, or haptic elements includes changing a subset of the first set of visual, olfactory, gustatory, auditory, or haptic elements in the first visual environment.

Embodiment 36: The apparatus of any one of Embodiments 32-35, wherein the multi-sensory device includes a haptic vest configured to generate a vibration.

Embodiment 37: The apparatus of Embodiment 36, wherein modifying the scene to include the second or third sets of visual, olfactory, gustatory, auditory, or haptic elements includes changing the vibration generated by the haptic vest or moving a location of the vibration generated by the haptic vest.

Embodiment 38: The apparatus of any one of Embodiments 32-37, wherein the user data further includes at least one of: heart rate data, respiratory data, PPG data, galvanic skin response data, blood glucose data, pupillometry data, eye movement data, electromyography (EMG) data, electrodermal activity (EDA) data, blood pressure data, or body temperature.

Embodiment 39: The apparatus of any one of Embodiments 32-37, wherein the processor is configured to modify the scene to include the second set of visual, olfactory, gustatory, auditory, or haptic elements at a first rate, and the processor is configured to modify the scene to include the third set of visual, olfactory, gustatory, auditory, or haptic elements at a second rate, the second rate being slower than the first rate.

Embodiment 40: The apparatus of any one of Embodiments 32-37, wherein the processor is configured to modify the scene to include the second set of visual, olfactory, gustatory, auditory, or haptic elements by abruptly removing the first set of visual, olfactory, gustatory, auditory, or haptic elements and presenting the second set of visual, olfactory, gustatory, auditory, or haptic elements, and the processor is configured to modify the scene to include the third set of visual, olfactory, gustatory, auditory, or haptic elements by gradually fading away the first set of visual, olfactory, gustatory, auditory, or haptic elements and presenting the third set of visual, olfactory, gustatory, auditory, or haptic elements.

Embodiment 41: The apparatus of any one of Embodiments 32-40, wherein a degree of difference between the second set of visual, olfactory, gustatory, auditory, or haptic elements and the first set of visual, olfactory, gustatory, auditory, or haptic elements is greater than that between the third set of visual, olfactory, gustatory, auditory, or haptic elements and the first set of visual, olfactory, gustatory, auditory, or haptic elements.

Embodiment 42: The apparatus of any one of Embodiments 32-41, wherein the processor is further configured to, prior to presenting the scene: determine whether an impedance measured by the EEG sensor falls within a predetermined range of impedances; in response to the impedance being within the predetermined range, present an indication that the EEG sensor is properly positioned; in response to the impedance not being within the predetermined range, present an indication that the EEG sensor needs to be readjusted.

Embodiment 43: An apparatus, comprising: a multi-sensory presentation device configured to present at least one of a visual, olfactory, gustatory, auditory, or haptic signal to a user; one or more electroencephalography (EEG) sensors configured to measure EEG data of the user; a memory; a processor operatively coupled to the memory, the multi-sensory presentation device, and the one or more EEG sensors, the processor configured to: present, using the multi-sensory presentation device and after the user has received a drug treatment, a scene to the user, the scene including a first set of visual, olfactory, gustatory, auditory, or haptic elements; while the scene is being presented, iteratively perform: measuring, using the one or more EEG sensors, the EEG data; determining, using a model trained to measure a state of the user, and based on the EEG data, a score of the user indicative of a state of the user; in response to the score being lower than a threshold, modifying, based on the score of the user, the scene to include a second set of visual, olfactory, gustatory, auditory, or haptic elements different from the first set of visual, olfactory, gustatory, auditory, or haptic elements; and in response to the score being greater than the threshold for a set period of time, modifying the scene to include a third set of visual, olfactory, gustatory, auditory, or haptic elements different from the first and second sets of visual, olfactory, gustatory, auditory, or haptic elements; and continue to present the scene to the user until a predetermined period of time has elapsed from the user receiving the drug treatment.

Embodiment 44: The apparatus of Embodiment 43, wherein the multi-sensory device is configured to present at least two of visual, olfactory, gustatory, auditory, or haptic signals.

Embodiment 45: The apparatus of any one of Embodiments 43-44, wherein the multi-sensory device includes a virtual reality (VR) device, a projector, smart glasses, or a parallax screen configured to generate a visual environment.

Embodiment 46: The apparatus of Embodiment 45, wherein modifying the scene to include the second set of visual, olfactory, gustatory, auditory, or haptic elements includes changing from a first visual environment to a second visual environment, and modifying the scene to include the third set of visual, olfactory, gustatory, auditory, or haptic elements includes changing a subset of the first set of visual, olfactory, gustatory, auditory, or haptic elements in the first visual environment.

Embodiment 47: The apparatus of any one of Embodiments 43-46, wherein the multi-sensory device includes a haptic vest configured to generate a vibration.

Embodiment 48: The apparatus of Embodiment 47, wherein modifying the scene to include the second or third sets of visual, olfactory, gustatory, auditory, or haptic elements includes changing the vibration generated by the haptic vest or moving a location of the vibration generated by the haptic vest.

Embodiment 49: The apparatus of any one of Embodiments 43-48, wherein the processor is configured to modify the scene to include the second set of visual, olfactory, gustatory, auditory, or haptic elements at a first rate, and the processor is configured to modify the scene to include the third set of visual, olfactory, gustatory, auditory, or haptic elements at a second rate, the second rate being slower than the first rate.

Embodiment 50: The apparatus of any one of Embodiments 43-48, wherein the processor is configured to modify the scene to include the second set of visual, olfactory, gustatory, auditory, or haptic elements by abruptly removing the first set of visual, olfactory, gustatory, auditory, or haptic elements and presenting the second set of visual, olfactory, gustatory, auditory, or haptic elements, and the processor is configured to modify the scene to include the third set of visual, olfactory, gustatory, auditory, or haptic elements by gradually fading away the first set of visual, olfactory, gustatory, auditory, or haptic elements and presenting the third set of visual, olfactory, gustatory, auditory, or haptic elements.

Embodiment 51: The apparatus of any one of Embodiments 43-48, wherein a degree of difference between the second set of visual, olfactory, gustatory, auditory, or haptic elements and the first set of visual, olfactory, gustatory, auditory, or haptic elements is greater than that between the third set of visual, olfactory, gustatory, auditory, or haptic elements and the first set of visual, olfactory, gustatory, auditory, or haptic elements.

Embodiment 52: A method, comprising: presenting, using a multi-sensory presentation device and after the user has received a drug treatment, a scene to the user, the scene including a first set of visual, olfactory, gustatory, auditory, or haptic elements; while the scene is being presented, iteratively performing: measuring, using a set of sensors including an electroencephalography (EEG) sensor and a photoplethysmography (PPG) sensor, user data including at least EEG data and heart rate variability (HRV) data; determining, using a model trained to measure a state of the user, and based on the user data, a score of the user indicative of a state of the user; in response to the score being lower than a threshold, modifying, based on the score of the user, the scene to include a second set of visual, olfactory, gustatory, auditory, or haptic elements different from the first set of visual, olfactory, gustatory, auditory, or haptic elements; and in response to the score being greater than the threshold for a set period of time, modifying the scene to include a third set of visual, olfactory, gustatory, auditory, or haptic elements different from the first and second sets of visual, olfactory, gustatory, auditory, or haptic elements; and continuing to present the scene to the user until a predetermined period of time has elapsed from the user receiving the drug treatment.

It should be understood that the disclosed embodiments are not representative of all claimed innovations. As such, certain aspects of the disclosure have not been discussed herein. That alternate embodiments may not have been presented for a specific portion of the innovations or that further undescribed alternate embodiments may be available for a portion is not to be considered a disclaimer of those alternate embodiments. Thus, it is to be understood that other embodiments can be utilized, and functional, logical, operational, organizational, structural and/or topological modifications may be made without departing from the scope of the disclosure. As such, all examples and/or embodiments are deemed to be non-limiting throughout this disclosure Some embodiments described herein relate to methods. It should be understood that such methods can be computer implemented methods (e.g., instructions stored in memory and executed on processors). Where methods described above indicate certain events occurring in certain order, the ordering of certain events can be modified. Additionally, certain of the events can be performed repeatedly, concurrently in a parallel process when possible, as well as performed sequentially as described above. Furthermore, certain embodiments can omit one or more described events.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using Python, Java, JavaScript, C++, and/or other programming languages and software development tools. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

In order to address various issues and advance the art, the entirety of this application (including the Cover Page, Title, Headings, Background, Summary, Brief Description of the Drawings, Detailed Description, Claims, Abstract, Figures, Appendices, and otherwise) shows, by way of illustration, various embodiments in which the claimed innovations can be practiced. The advantages and features of the application are of a representative sample of embodiments only and are not exhaustive and/or exclusive. They are presented to assist in understanding and teach the claimed principles.

The drawings primarily are for illustrative purposes and are not intended to limit the scope of the subject matter described herein. The drawings are not necessarily to scale; in some instances, various aspects of the subject matter disclosed herein can be shown exaggerated or enlarged in the drawings to facilitate an understanding of different features.

The acts performed as part of a disclosed method(s) can be ordered in any suitable way. Accordingly, embodiments can be constructed in which processes or steps are executed in an order different than illustrated, which can include performing some steps or processes simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of," or "exactly one of" "Consisting essentially of," when used in the embodiments, shall have its ordinary meaning as used in the field of patent law.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

What is claimed is:

1. An apparatus, comprising:
    a virtual reality (VR) device configured to present at least one of a visual, olfactory, gustatory, auditory, or haptic signal to a user;
    a set of sensors configured to measure user data, the set of sensors including at least an electroencephalography (EEG) sensor and a photoplethysmography (PPG) sensor;
    a memory; and
    a processor operatively coupled to the virtual reality device, the set of sensors, and the memory, the processor configured to:
        present, using the VR device, a plurality of sets of objects to the user according to a sequence by:
            presenting, using the VR device, a first set of objects of the plurality of sets of objects to the user, the first set of objects including visual, olfactory, gustatory, auditory, or haptic elements;
            instructing the user to engage in an activity for increasing focus or relaxation for the user;
            after the user has been instructed to engage in the activity, iteratively performing until a score indicative of a state of the user satisfies a metric:
                measuring, using the set of sensors, the user data including at least EEG data and heart rate variability (HRV) data;
                determining, using a model trained to measure the state of the user, and based on the user data, the score of the user; and
                in response to the score of the user being above a threshold, modifying, using the VR device, the presentation of the first set of objects such that the first set of objects form or follow a pattern or presenting, using the VR device, an additional object;
            in response to the score of the user satisfying the metric, presenting, using the VR device, a second set of objects of the plurality of sets of objects to the user; and
            presenting each set of objects of the plurality of sets of objects subsequent to the first and second sets of objects in the sequence in response to the score of the user satisfying the metric after a set of objects of the plurality of sets of objects immediately preceding each set of objects of the plurality of set of objects in the sequence is presented.

2. The apparatus of claim 1, wherein the additional object is an auditory element including a tone, a sound effect, or music.

3. The apparatus of claim 1, wherein the processor is configured to instruct the user to engage in the activity for increasing focus or relaxation for the user by:
    instructing the user to focus on breathing;
    instructing the user to focus on a visual element or an auditory element included in the first set of objects;
    instructing the user to focus on a body of the user; or
    performing a combination thereof.

4. The apparatus of claim 1, wherein the user data further includes at least one of:
    heart rate data, respiratory data, PPG data, galvanic skin response data, blood glucose data, pupillometry data, eye movement data, electromyography (EMG) data, electrodermal activity (EDA) data, blood pressure data, or body temperature.

5. The apparatus of claim 1, wherein the score of the user satisfies the metric when the score of the user remains above the threshold for a set period of time.

6. The apparatus of claim 1, wherein the first set of objects includes a first set of visual elements including the visual elements, the processor configured to modify the presentation of the first set of objects by moving one or more visual elements of the first set of visual elements to form a pattern with the first set of visual elements.

7. The apparatus of claim 1, wherein the first set of objects includes a first set of audio elements including the auditory elements, the processor configured to modify the presentation of the first set of audio elements by changing an intensity or frequency of one or more audio elements of the first set of audio elements.

8. The apparatus of claim 1, wherein the processor is configured to present the second set of objects while the first set of objects continue being presented.

9. The apparatus of claim 1, wherein the processor is further configured to fade away the first set of objects before presenting the second set of objects.

10. The apparatus of claim 1, wherein the user data is measured at least during an initial period of time,
the processor further configured to adjust, based on the user data measured during the initial period of time, the threshold to change a difficulty of satisfying the metric.

11. The apparatus of claim 10, wherein the processor is configured to adjust the threshold by:
determining, based on the user data measured during the initial period of time, a competency group for the user, the competency group being from a set of competency groups; and
setting the threshold based on the competency group determined for the user.

12. The apparatus of claim 10, wherein the processor configured to adjust the threshold by:
determining, based on the user data measured during the initial period of time, a rate of progression through the plurality of sets of objects; and
setting the threshold based on the rate of progression.

13. The apparatus of claim 12, wherein the processor is configured to set the threshold based on the rate of progression by:
increasing the threshold when the rate of progression is greater than a predetermined rate; and
decreasing the threshold when the rate of progression is less than the predetermined rate.

14. The apparatus of claim 1, wherein the processor is further configured to, in response to the state of the user satisfying the metric after the set of objects of the plurality of sets of objects last in the sequence is presented, send instructions to administer a drug treatment to the user.

15. The apparatus of claim 1, wherein the model is a user-specific model, the processor being further configured to, prior to presenting the plurality of sets of objects:
present, during a calibration phase, a set of environmental stimulations considered to be calming to the user interspersed with periods of no environmental stimulation;
measure separate user data during the calibration phase; and
adapt, using the separate user data measured during the calibration phase, a generic model trained using data other than the separate user data to measure states of users to be the user-specific model for measuring the state of the user.

16. The apparatus of claim 1, wherein the processor is further configured to, prior to presenting the plurality of sets of objects:
determine whether an impedance measured by the EEG sensor falls within a predetermined range of impedances;
in response to the impedance being within the predetermined range, present an indication that the EEG sensor is properly positioned; and
in response to the impedance not being within the predetermined range, present an indication that the EEG sensor needs to be readjusted.

17. The apparatus of claim 1, wherein in response to the score of the user being below the threshold, modifying, using the VR device, the presentation of the first set of objects such that the first set of objects regress to an earlier state.

18. An apparatus, comprising:
a virtual reality (VR) device configured to present at least one of a visual, olfactory, gustatory, auditory, or haptic signal to a user;
one or more electroencephalography (EEG) sensors configured to measure EEG data of the user;
a memory; and
a processor operatively coupled to the virtual reality device, the one or more EEG sensors, and the memory, the processor configured to:
present, using the VR device, a plurality of sets of objects to the user according to a sequence by:
presenting, using the VR device, a first set of objects of the plurality of sets of objects to the user, the first set of objects including visual, olfactory, gustatory, auditory, or haptic elements;
instructing the user to engage in an activity for increasing focus or relaxation for the user;
after the user has been instructed to engage in the activity, iteratively performing until a score indicative of a state of the user satisfies a metric:
measuring, using the one or more EEG sensors, the EEG data;
determining, using a model trained to measure the state of the user, and based on the EEG data, the score of the user; and
in response to the score of the user being above a threshold, modifying, using the VR device, the presentation of the first set of objects such that the first set of objects form or follow a pattern or presenting, using the VR device, an additional object;
in response to the score of the user satisfying the metric, presenting, using the VR device, a second set of objects of the plurality of sets of objects to the user; and
presenting each set of objects of the plurality of sets of objects subsequent to the first and second sets of objects in the sequence in response to the score of the user satisfying the metric after a set of objects of the plurality of sets of objects immediately preceding each set of objects of the plurality of set of objects in the sequence is presented.

19. The apparatus of claim 18, wherein the additional object is an auditory element including a tone, a sound effect, or music.

20. The apparatus of claim 18, wherein the score of the user satisfies the metric when the score of the user remains above the threshold for a set period of time.

21. The apparatus of claim 18, wherein the first set of objects includes a first set of visual elements including the visual elements, the processor configured to modify the presentation of the first set of objects by moving one or more visual elements of the first set of visual elements to form a pattern with the first set of visual elements.

22. The apparatus of claim 18, wherein the first set of objects includes a first set of audio elements including the auditory elements, the processor configured to modify the presentation of the first set of audio elements by changing an intensity or frequency of one or more audio elements of the first set of audio elements.

23. An apparatus, comprising:
a virtual reality (VR) device configured to present at least one of a visual, olfactory, gustatory, auditory, or haptic signal to a user;
a set of sensors configured to measure user data, the set of sensors including at least an electroencephalography (EEG) sensor and a photoplethysmography (PPG) sensor;
a memory; and
a processor operatively coupled to the virtual reality device, the set of sensors, and the memory, the processor configured to:
present, during a calibration phase, a set of environmental stimulations considered to be calming to the user interspersed with periods of no environmental stimulation;
measure first user data during the calibration phase;
adapt, using the first user data measured during the calibration phase, a generic model trained using data other than the first user data to measure states of users to be a user-specific model for measuring a state of the user;
present, after the calibration phase, and using the VR device, a scene including a first set of objects to the user, the first set of objects including visual, olfactory, gustatory, auditory, or haptic elements;
instruct the user to engage in an activity for increasing focus or relaxation for the user;
after the user has been instructed to engage in the activity, iteratively perform until a score indicative of a state of the user satisfies a metric:
measuring, using the set of sensors, second user data of the user, the second user data including at least EEG data and heart rate variability (HRV) data;
determining, using the user-specific model, and based on the second user data, the score of the user; and
in response to the score of the user being above a threshold, modifying, using the VR device, the presentation of the first set of objects such that the first set of objects form or follow a pattern or presenting, using the VR device, an additional object; and
in response to the score of the user satisfying the metric, present, using the VR device, a second set of objects to the user.

24. The apparatus of claim 23, wherein the score of the user satisfies the metric when the score of the user remains above the threshold for a set period of time.

25. The apparatus of claim 23, wherein the first set of objects includes a first set of visual elements including the visual elements, the processor configured to modify the presentation of the first set of objects by moving one or more visual elements of the first set of visual elements to form a pattern with the first set of visual elements.

26. The apparatus of claim 23, wherein the first set of objects includes a first set of auditory elements including the audio elements, the processor configured to modify the presentation of the first set of audio elements by changing an intensity or frequency of one or more audio elements of the first set of audio elements.

27. An apparatus, comprising:
a virtual reality (VR) device configured to present at least one of a visual, olfactory, gustatory, auditory, or haptic signal to a user;
one or more electroencephalography (EEG) sensors configured to measure EEG data of the user;
a memory; and
a processor operatively coupled to the virtual reality device, the one or more EEG sensors, and the memory, the processor configured to:
present, during a calibration phase, a set of environmental stimulations considered to be calming to the user interspersed with periods of no environmental stimulation;
measure first EEG data during the calibration phase;
adapt, using the first EEG data measured during the calibration phase, a generic model trained using data other than the first EEG data to measure states of users to be a user-specific model for measuring a state of the user;
present, after the calibration phase, and using the VR device, a scene including a first set of objects to the user, the first set of objects including visual, olfactory, gustatory, auditory, or haptic elements;
instruct the user to engage in an activity for increasing focus or relaxation for the user;
after the user has been instructed to engage in the activity, iteratively perform until a score indicative of a state of the user satisfies a metric:
measuring, using the one or more EEG sensors, second EEG data;
determining, using the user-specific model, and based on the second EEG data, the score of the user; and
in response to the score of the user being above a threshold, modifying, using the VR device, the presentation of the first set of objects such that the first set of objects form or follow a pattern or presenting, using the VR device, an additional object; and
in response to the score of the user satisfying the metric, present, using the VR device, a second set of objects to the user.

28. The apparatus of claim 27, wherein the score of the user satisfies the metric when the score of the user remains above the threshold for a set period of time.

29. The apparatus of claim 27, wherein the first set of objects includes a first set of visual elements including the visual elements, the processor configured to modify the presentation of the first set of objects by moving one or more visual elements of the first set of visual elements to form a pattern with the first set of visual elements.

30. The apparatus of claim 27, wherein the first set of objects includes a first set of audio elements including the auditory elements, the processor configured to modify the presentation of the first set of audio elements by changing an intensity or frequency of one or more audio elements of the first set of audio elements.

* * * * *

UNITED STATES PATENT AND TRADEMARK OFFICE
CERTIFICATE OF CORRECTION

PATENT NO. : 11,660,419 B2
APPLICATION NO. : 17/866430
DATED : May 30, 2023
INVENTOR(S) : Prahlad Krishnan It is certified that error appears in the above-identified patent and that said Letters Patent is hereby corrected as shown below:

In the Claims

Column 55, Claim 26, Line 57:
"objects includes a first set of auditory elements including the"

Should read:
-- objects includes a first set of audio elements including the --

Column 55, Claim 26, Line 58:
"audio elements, the processor configured to modify the"

Should read:
-- auditory elements, the processor configured to modify the --

Signed and Sealed this
Twenty-ninth Day of August, 2023

Katherine Kelly Vidal
*Director of the United States Patent and Trademark Office*